US010369022B2

(12) United States Patent
van der Merwe et al.

(10) Patent No.: US 10,369,022 B2
(45) Date of Patent: *Aug. 6, 2019

(54) SYSTEM FOR CONTROL OF A PROSTHETIC DEVICE

(71) Applicant: DEKA Products Limited Partnership, Manchester, NH (US)

(72) Inventors: Dirk Albertus van der Merwe, Canterbury, NH (US); Gregory R. Lanier, Manchester, NH (US); John M. Kerwin, Manchester, NH (US); Gerald M. Guay, Greenville, NH (US); N. Christopher Perry, Manchester, NH (US); Susan D. Dastous, Litchfield, NH (US)

(73) Assignee: DEKA PRODUCTS LIMITED PARTNERSHIP, Manchester, NH (US)

( * ) Notice: Subject to any disclaimer, the term of this patent is extended or adjusted under 35 U.S.C. 154(b) by 320 days.

This patent is subject to a terminal disclaimer.

(21) Appl. No.: 14/833,781

(22) Filed: Aug. 24, 2015

(65) Prior Publication Data

US 2015/0351939 A1    Dec. 10, 2015

Related U.S. Application Data

(63) Continuation of application No. 13/088,085, filed on Apr. 15, 2011, now Pat. No. 9,114,030, which is a (Continued)

(51) Int. Cl.
*A61F 2/54* (2006.01)
*A61F 2/70* (2006.01)
(Continued)

(52) U.S. Cl.
CPC .................. *A61F 2/68* (2013.01); *A61F 2/54* (2013.01); *A61F 2/582* (2013.01); *A61F 2/585* (2013.01);
(Continued)

(58) Field of Classification Search
CPC .... A61F 2/68; A61F 2/54; A61F 2/582; A61F 2/583; A61F 2/585; A61F 2/586; A61F 2/72
See application file for complete search history.

(56) References Cited

U.S. PATENT DOCUMENTS 4,841,773 A    6/1989  Stewart
5,252,102 A   10/1993  Singer et al.
(Continued)

FOREIGN PATENT DOCUMENTS

WO    02/00158 A2    1/2002
WO  2009/155595 A2   12/2009

OTHER PUBLICATIONS

Lee et al., "A Composite Discrete/Continuous Control of Robot Manipulators", Apr. 1991, Carnegie Mellon University: The Robotics Institute, Pittsburg, PA, pp. 1-21.*
(Continued)

*Primary Examiner* — Marcia L Watkins
(74) *Attorney, Agent, or Firm* — McCormick, Paulding & Huber LLP

(57) ABSTRACT

A control system for control of a prosthetic device having a plurality of actuators receives an orientation signal indicative of a desired movement. The control system evaluates whether the prosthetic device may move as desired with a current angle of rotation and commands at least one actuator to move the prosthetic device as desired by maintaining the current angle of rotation or by adjusting the angle of rotation if the prosthetic device cannot move as desired with the current angle. The control system may alternate between commanding a first subset of actuators and a second subset of actuators each time the orientation signal is indicative of a neutral position. The control system may include a position sensor and a compliance sensor and may command at least one actuator based on a combination of positional control using the position sensor and force control using the compliance sensor.

9 Claims, 36 Drawing Sheets

Related U.S. Application Data continuation-in-part of application No. 12/706,575, filed on Feb. 16, 2010, now Pat. No. 8,864,845, which is a continuation-in-part of application No. 12/027,116, filed on Feb. 6, 2008, now Pat. No. 8,821,587.

(60) Provisional application No. 60/899,834, filed on Feb. 6, 2007, provisional application No. 60/963,638, filed on Aug. 6, 2007, provisional application No. 61/168,832, filed on Apr. 13, 2009, provisional application No. 61/221,858, filed on Jun. 30, 2009.

(51) Int. Cl.
*A61F 2/58* (2006.01)
*A61F 2/68* (2006.01)
*A61F 2/72* (2006.01)
*A61F 2/76* (2006.01)
*A61F 2/50* (2006.01)
*A61B 5/0488* (2006.01)
*A61B 5/103* (2006.01)
*A61B 5/00* (2006.01)

(52) U.S. Cl.
CPC ............ *A61F 2/586* (2013.01); *A61B 5/0488* (2013.01); *A61B 5/1036* (2013.01); *A61B 5/4528* (2013.01); *A61F 2/583* (2013.01); *A61F 2/72* (2013.01); *A61F 2002/5018* (2013.01); *A61F 2002/5021* (2013.01); *A61F 2002/543* (2013.01); *A61F 2002/546* (2013.01); *A61F 2002/587* (2013.01); *A61F 2002/6827* (2013.01); *A61F 2002/701* (2013.01); *A61F 2002/704* (2013.01); *A61F 2002/705* (2013.01); *A61F 2002/707* (2013.01); *A61F 2002/762* (2013.01); *A61F 2002/764* (2013.01); *A61F 2002/7625* (2013.01); *A61F 2002/7635* (2013.01); *A61F 2002/7645* (2013.01); *A61F 2002/7685* (2013.01)

(56) References Cited

U.S. PATENT DOCUMENTS

| | | |
|---|---|---|
| 5,617,595 A | 4/1997 | Landi et al. |
| 5,748,845 A | 5/1998 | Labun et al. |
| 5,881,609 A | 3/1999 | Palmer |
| 6,685,661 B2 | 2/2004 | Peled |
| 8,430,578 B1 | 4/2013 | Theriault |
| 9,114,028 B2 | 8/2015 | Langenfeld et al. |
| 10,092,423 B2 * | 10/2018 | Goldfarb ................... A61F 2/58 |
| 2003/0018388 A1 | 1/2003 | Comer |
| 2004/0088057 A1 * | 5/2004 | Bedard ...................... A61F 2/68 623/25 |
| 2004/0267379 A1 | 12/2004 | Pasolini |
| 2005/0177952 A1 | 8/2005 | Wilkinson et al. |
| 2005/0256507 A1 | 11/2005 | Long et al. |
| 2006/0135883 A1 | 6/2006 | Jonsson et al. |
| 2008/0078033 A1 | 4/2008 | Wyatt et al. |

OTHER PUBLICATIONS

Invitation to Pay Additional Fees and, Where Applicable, Protest Fee including Partial Search Report from corresponding International Appln. No. PCT/US2016/043864 dated Nov. 11, 2016 (7 pages).

* cited by examiner

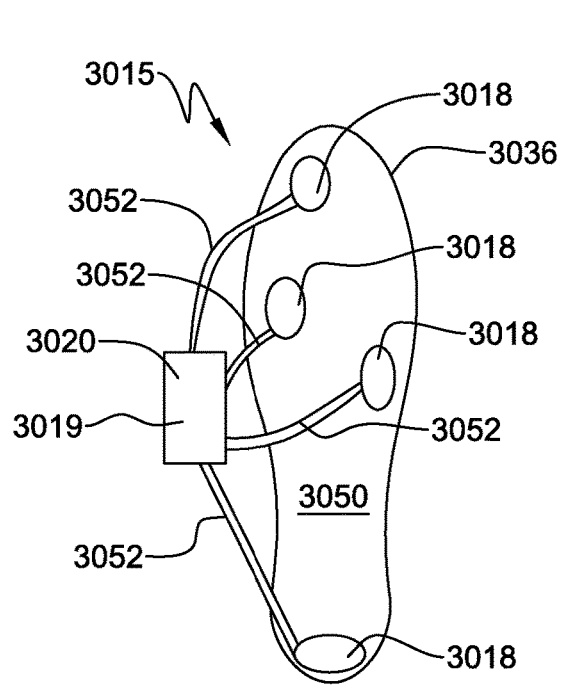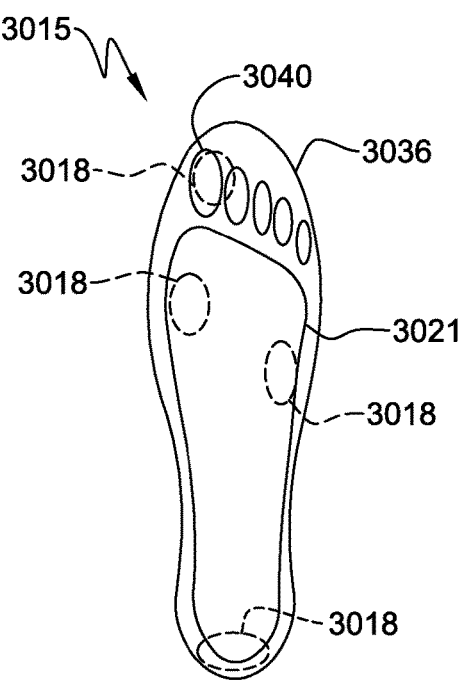
FIG. 8A  FIG. 8B
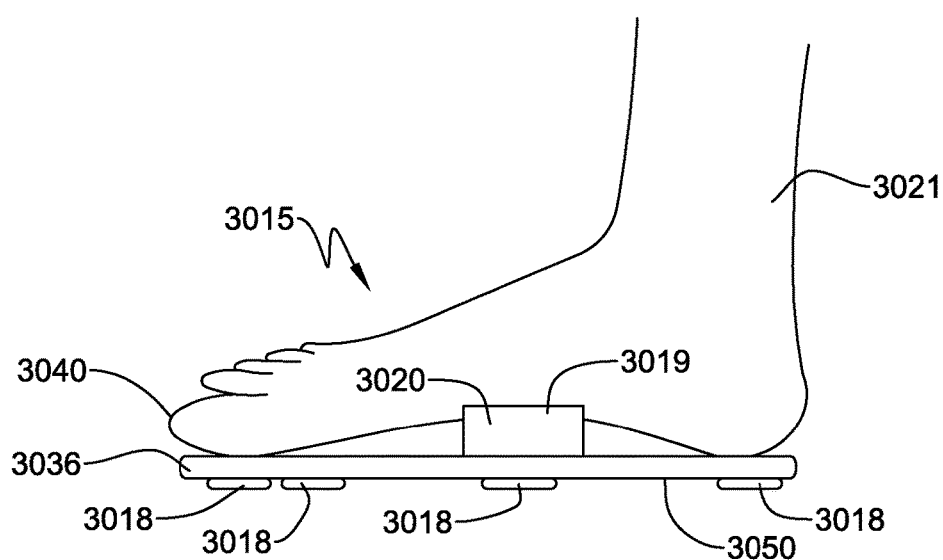
FIG. 9

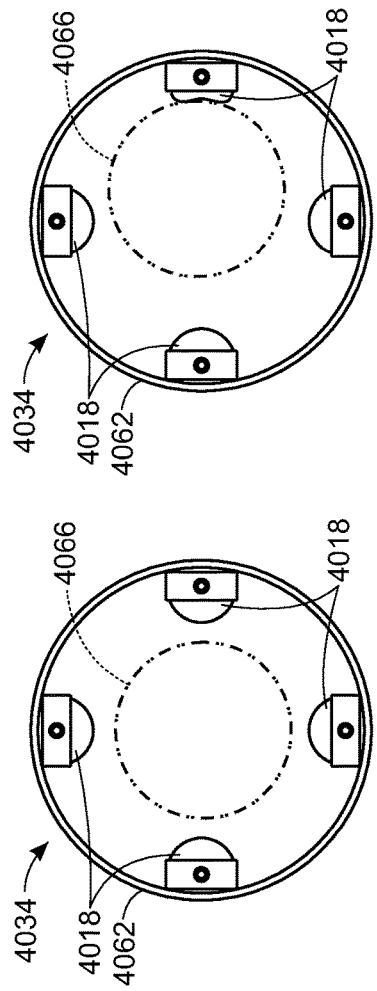
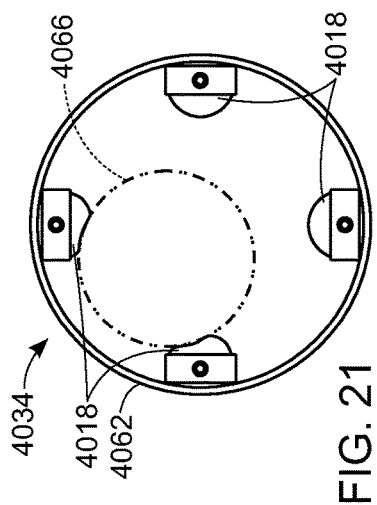
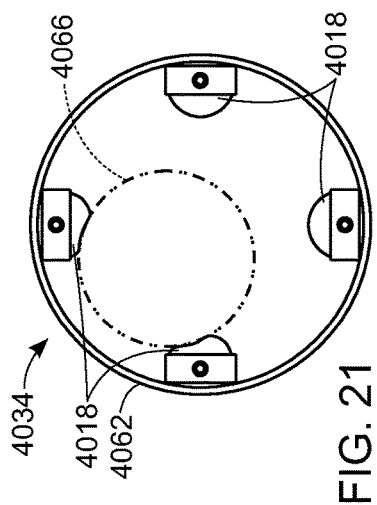
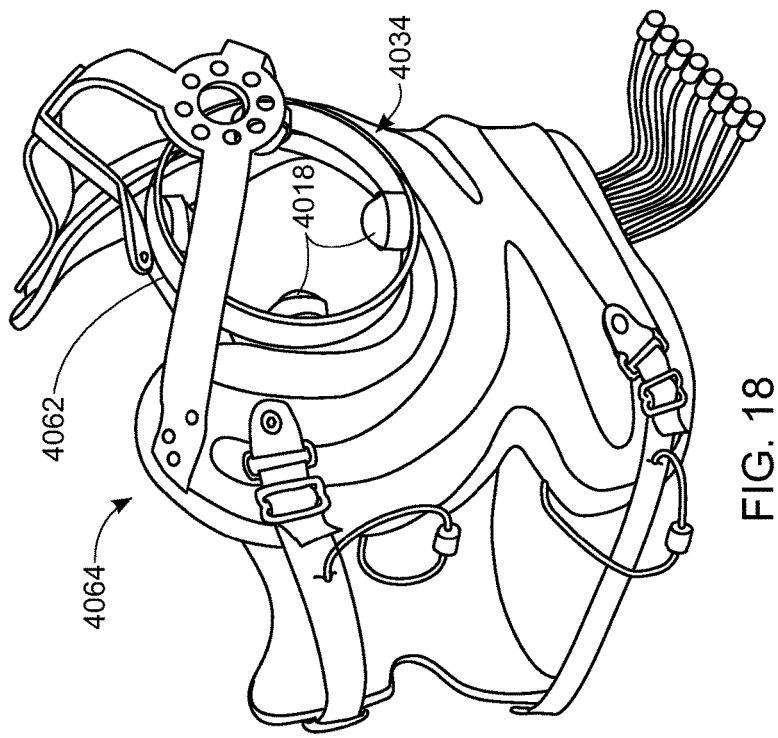

SYSTEM FOR CONTROL OF A PROSTHETIC DEVICE

CROSS-REFERENCE TO RELATED APPLICATIONS

This application is a continuation of U.S. patent application Ser. No. 13/088,085, filed Apr. 15, 2011, now U.S. Pat. No. 9,114,030, issued Aug. 25, 2015, which is a continuation-in-part of U.S. patent application Ser. No. 12/706,575, filed Feb. 16, 2010, now U.S. Pat. No. 8,864,845, issued Oct. 21, 2014, which is a continuation-in-part of U.S. patent application Ser. No. 12/027,116, filed Feb. 6, 2008, now U.S. Pat. No. 8,821,587, issued Sep. 2, 2014, which claims priority from U.S. Provisional Patent Application Ser. No. 60/899,834, filed Feb. 6, 2007, and U.S. Provisional Patent Application Ser. No. 60/963,638, filed Aug. 6, 2007, each of which applications is hereby incorporated by reference in its entirety. U.S. application Ser. No. 12/706,575 also claims priority to U.S. Provisional Patent Application Ser. No. 61/168,832, filed Apr. 13, 2009, and U.S. Provisional Patent Application Ser. No. 61/221,858, filed Jun. 30, 2009, each of which is also hereby incorporated by reference in its entirety.

STATEMENT OF GOVERNMENT INTEREST

This invention was made with Government support under Contract Number W911NF-09-C-0035 awarded by the U.S. Army RDECOM ACQ CTR. The Government has certain rights in the invention.

TECHNICAL FIELD

The present invention relates to control of a prosthetic device and more particularly, to an apparatus and method for control of a prosthetic device.

BACKGROUND INFORMATION

Many remote controls have been designed to manipulate robotic devices, mechanical devices, and virtual devices. There is a desire for a control system that may process user signals quickly and accurately while providing smooth directional and proportional control of associated objects.

SUMMARY

In accordance with one aspect of the present invention, a control system for a prosthetic device is disclosed. The prosthetic device includes a plurality of actuators and a control module for commanding at least one actuator of the plurality of actuators. The control system includes at least one sensor module adapted to detect orientation changes that is in communication with the control module. The control module is configured to receive at least one orientation signal from the sensor module. The orientation signal may be indicative of a commanded direction of movement of the prosthetic device. The control module is further configured to evaluate whether the prosthetic device may move in the commanded direction with a current angle of rotation and to command at least one actuator to move the prosthetic device in the commanded direction.

According to some embodiments, the control module maintains the current angle of rotation of the prosthetic device when commanding the at least one actuator to move the prosthetic device in the commanded direction. In some embodiments, the control module is further configured to adjust the angle of rotation of the prosthetic device if the prosthetic device cannot move in the commanded direction with the current angle of rotation. The control module may adjust the angle of rotation of the prosthetic device in accordance with joint limits for at least one actuator. The control module may also adjust the angle of rotation of the prosthetic device in accordance with at least one position limiting boundary of the prosthetic device.

In accordance with another aspect of the present invention, a control system for a prosthetic device includes at least one sensor module adapted to detect orientation changes, at least one device module in communication with the at least one sensor module and at least one actuator configured to receive commands from the device module. The device module may control movement of the actuator based on a combination of positional control and force control. In some embodiments, the device module determines the combination of positional control and force control by calculating a measured impedance using at least one position sensor and at least one compliance sensor. The compliance sensor may detect compliance of a variety of structures of the prosthetic device including a thumb structure and/or an index structure and, in some embodiments, may maintain a force measured one compliance sensor to be substantially equal to a force measured by another compliance sensor.

In accordance with another aspect of the present invention a control system for a prosthetic device includes at least one sensor module adapted to detect orientation changes, the at least one sensor module having a neutral position at a first orientation. The control system also includes at least one device module in communication with the at least one sensor module and a plurality of actuators configured to receive commands from the device module. The plurality of actuators may include a first subset of actuators and a second subset of actuators and the device module may alternate between commanding the first subset of actuators and the second subset of actuators each time the at least one sensor module is returned to the neutral position at the first orientation.

In some embodiments, the first subset of actuators includes at least one actuator for at least one finger structure of the prosthetic device. The at least one finger structure may be a thumb structure, an index structure, a middle structure, a ring structure and a pinky structure. The second subset of actuators may also include at least one actuator for at least one finger structure of the prosthetic device and may be a thumb structure, an index structure, a middle structure, a ring structure and/or a pinky structure.

In accordance with some aspects of the present invention, the first subset of actuators includes at least one actuator for a middle structure, a ring structure and a pinky structure. In some embodiments, the first subset of actuators includes at least one actuator for an index structure and at least one actuator for a middle structure, a ring structure and a pinky structure. In some embodiments, the first subset of actuators includes at least one actuator for a thumb structure and at least one actuator for a middle structure, a ring structure and a pinky structure.

In accordance with some aspects of the present invention, the second subset of actuators includes at least one actuator for a thumb structure and/or at least one actuator for an index structure.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 8A is a top plan view of a one embodiment of a foot sensor module of FIG. 1A;

FIG. 8B is a top plan view of the foot sensor module of FIG. 8A, showing where the sensors are placed in relation to a user's foot;

FIG. 9 is a side elevation view of the foot sensor module of FIG. 8A;

FIG. 18 is a perspective view of the residuum controller of FIG. 16 incorporated into a prosthetic support apparatus;

FIG. 19 is a side view of the residuum controller of FIG. 16 in use;

FIG. 20 is a side view of the residuum controller of FIG. 16 in use;

FIG. 21 is a side view of the residuum controller of FIG. 16 in use;

DETAILED DESCRIPTION OF THE PREFERRED EMBODIMENTS

Figure 1A:
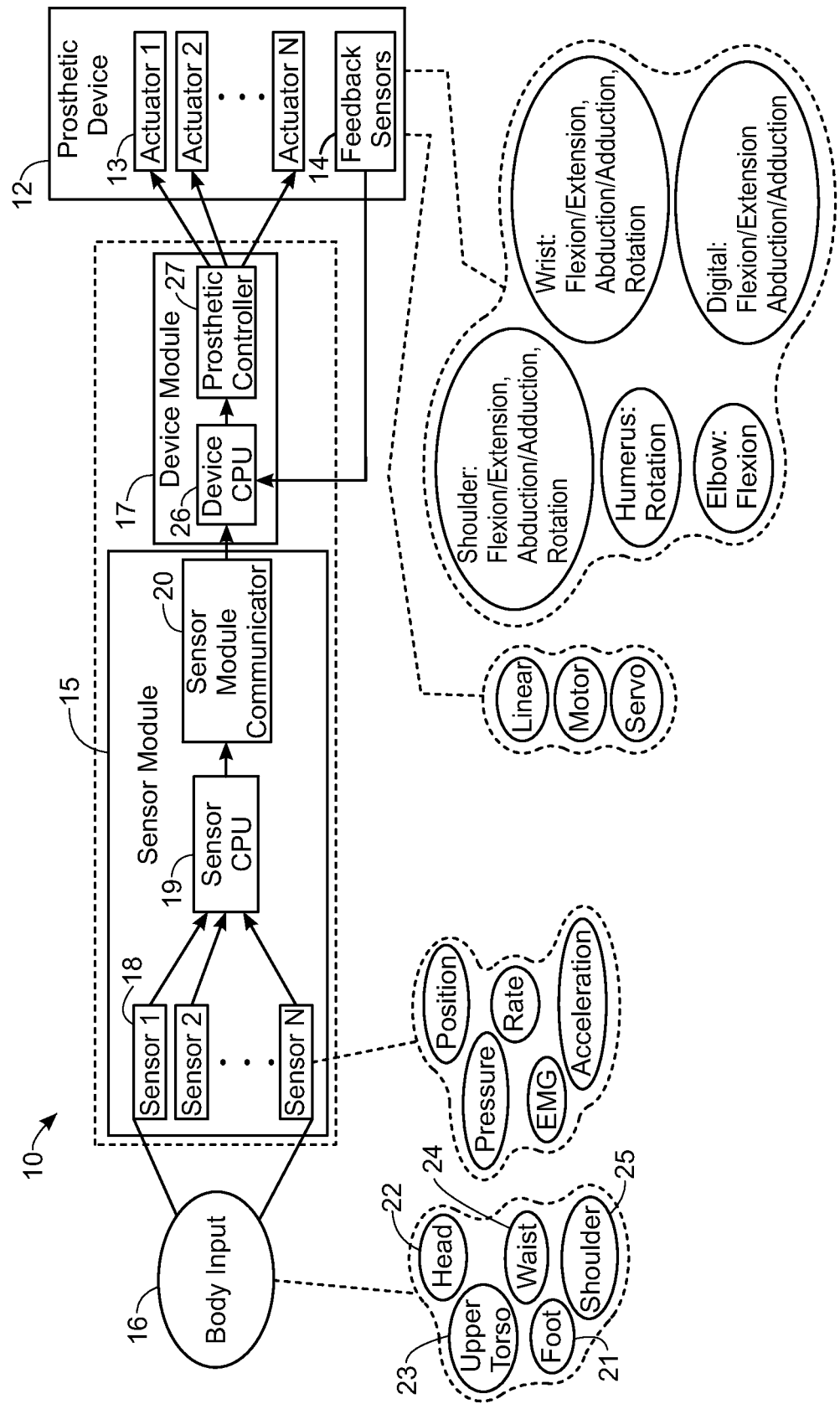
FIG. 1A is a schematic diagram of a prosthetic control apparatus and function thereof according to an embodiment of the present invention.

Referring to FIG. 1A, a schematic view of a control apparatus 10 for a prosthetic device 12 is shown. The prosthetic device 12 includes a plurality of actuators 13 that control movement of the prosthetic device 12 and one or more feedback sensors 14 for detecting the status of the prosthetic device 12 and/or support (not shown) for the prosthetic device 12. The control apparatus 10 comprises a sensor module 15 for detecting body input 16 and a device module 17 for commanding the prosthetic device 12. The control apparatus 10 may be used to control a variety of prosthetic devices, such as those disclosed in U.S. Pat. No. 9,114,028, issued Aug. 25, 2015, U.S. Pat. No. 8,449,624, issued May 28, 2013, and the U.S. Pat. No. 8,979,943, issued Mar. 17, 2015, each of which is hereby incorporated by reference in its entirety.

The sensor module 15 includes one or more sensors 18 connected to a sensor central processing unit (sensor CPU) 19 that is connected to a sensor module communicator 20. The one or more sensors 18 may be disposed at various locations on a user to sense the body input 16 from the user. For example, the sensor 18 may be located to provide pressure information supplied by a foot 21 of the user. Similarly, sensors 18 may be positioned to measure body input 16 from other body parts of the user such as a head 22, an upper torso 23, a waist 24 or a shoulder 25. In various embodiments, sensors 18 may measure, but are not limited to, one or more of the following: orientation, pressure, force, rate, or acceleration. Alternatively, in some embodiments, the sensors 18 may be EMG electrodes. In some embodiments, EMG electrode signals may be used in various controls, for example, but not limited to, turn on shoulder control, grip change control or movement control. The sensor CPU 19 inputs data from the one or more sensors 18 and filters and/or converts the data to generate user input signals. The user input signals are then sent to the device module 17 by the sensor module communicator 20. The sensor module communicator 20 may be hard wired to the device module 17 or may transmit the user input signals wirelessly, for example, but not limited to, through a radio transmitter, Bluetooth® or the like.

In some embodiments, the device module 17 includes a device CPU 26 connected to a prosthetic controller 27. The device CPU 26 receives the user input signals from the sensor module communicator 20 and prosthetic device status signals from the feedback sensors 14. Based on the signals from the sensor module communicator 20 and the feedback sensor 14, the device CPU 26 calculates prosthetic device actuator commands that are sent to the prosthetic actuators 13 by the prosthetic controller 27 to command movement of the prosthetic device 12.

Figure 1B:
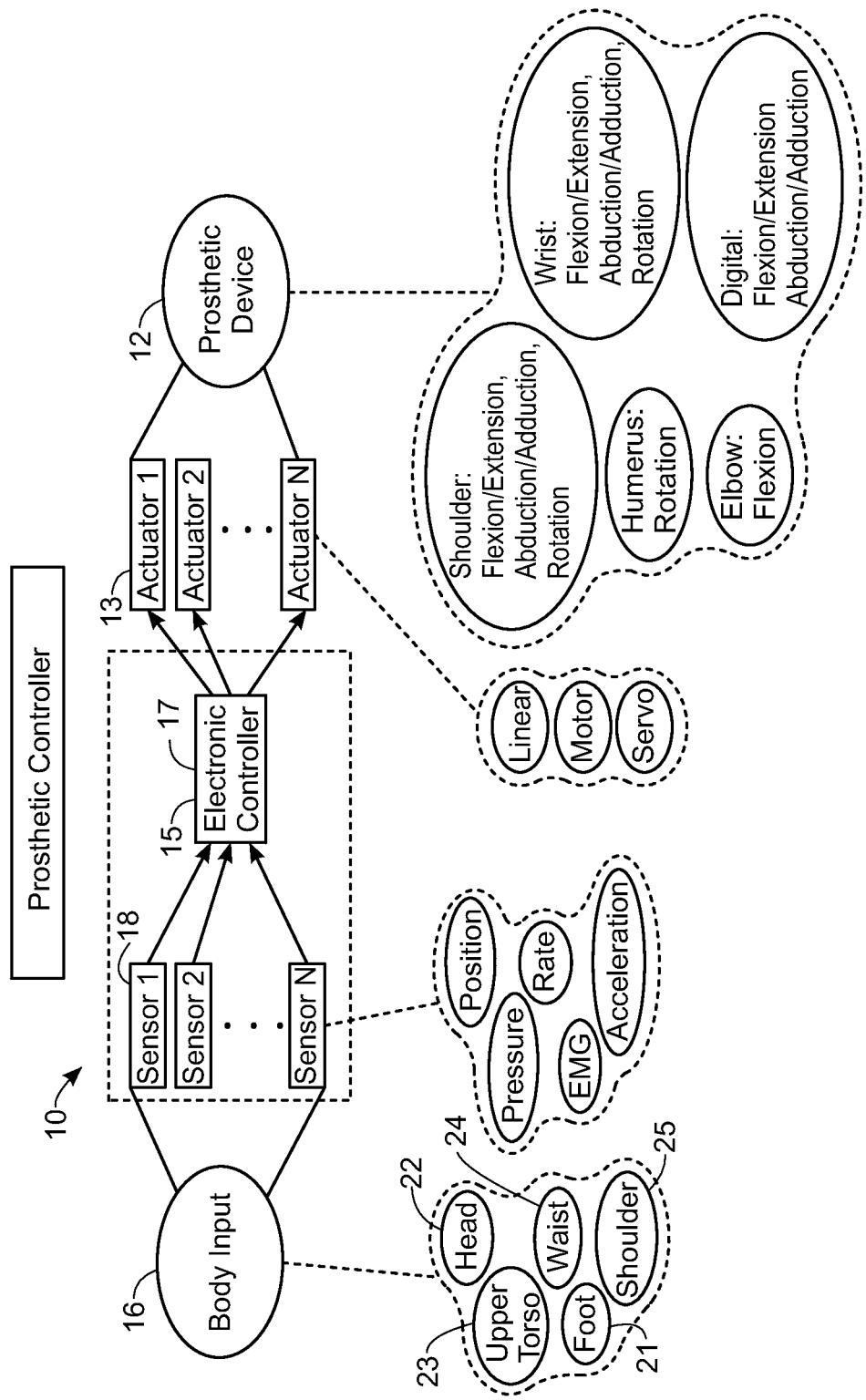
FIG. 1B, is a schematic diagram of another embodiment of the prosthetic control apparatus and function thereof of FIG. 1.

Although shown as having a separate sensor module 15 and device module 17, referring to FIG. 1B, in various embodiments, the control apparatus 10 may be comprised of a single unit having an electronic controller 28 that collects data from the sensors 18, completes algorithms to translate the data into a desired movement commands, and sets and runs the plurality of prosthetic actuators 13 to achieve the desired movement of the prosthetic device 12.

Figure 2:
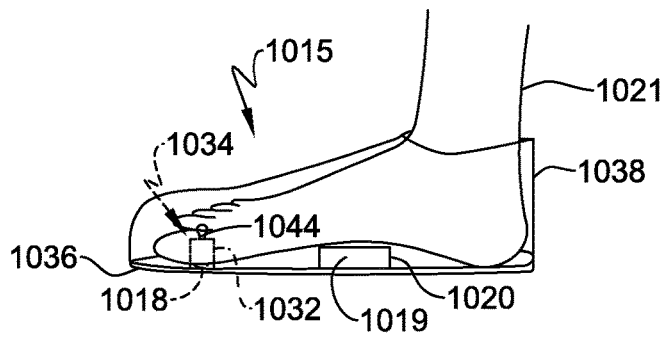
FIG. 2 is a side elevation view of one embodiment of a foot sensor module of the control apparatus of FIG. 1 placed inside a shoe.

Referring to FIG. 2, wherein like numerals represent like elements, one embodiment of the control apparatus 10 includes a foot sensor module 1015. In some embodiments, the foot sensor module 1015 comprises one or more inner sole sensors 1018, the sensor CPU 1019 and the sensor communicator 1020. In this embodiment, at least one inner sole sensor 1018 is positioned in a housing 1032 of a joystick 1034 and senses motion of the joystick 1034, which has at least two degrees of freedom. The joystick 1034 is placed on a sole 1036 of footwear 1038, and connected to the sensor CPU 1019.

Figure 3:
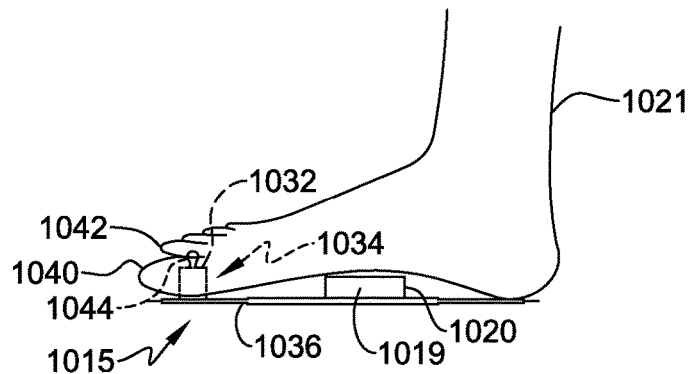
FIG. 3 is a side elevation of the foot sensor module of FIG. 2.
Figure 4:
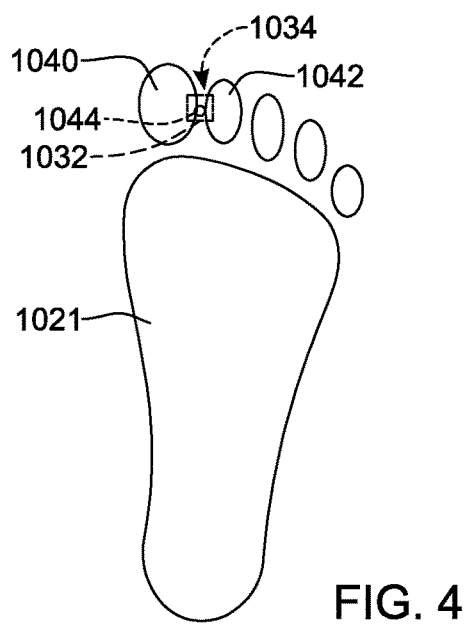
FIG. 4 is a top plan view of one embodiment of a foot sensor module.
Figures 5A, 5B:
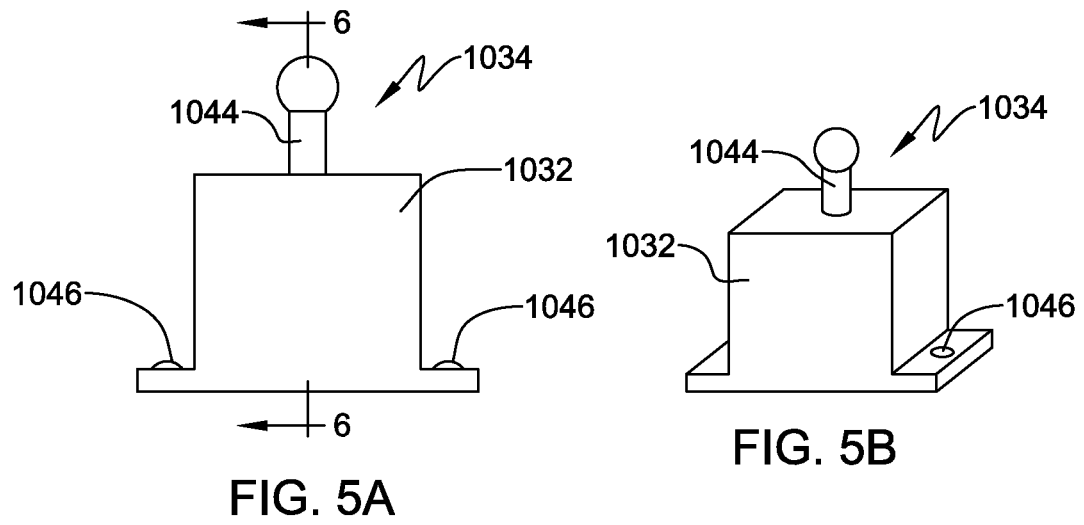
FIG. 5A is a side plan view of a joystick according to one embodiment of a motion reader for the foot sensor module of FIG. 2.
FIG. 5B is a side elevation view the joystick of FIG. 5A.
Figure 6:
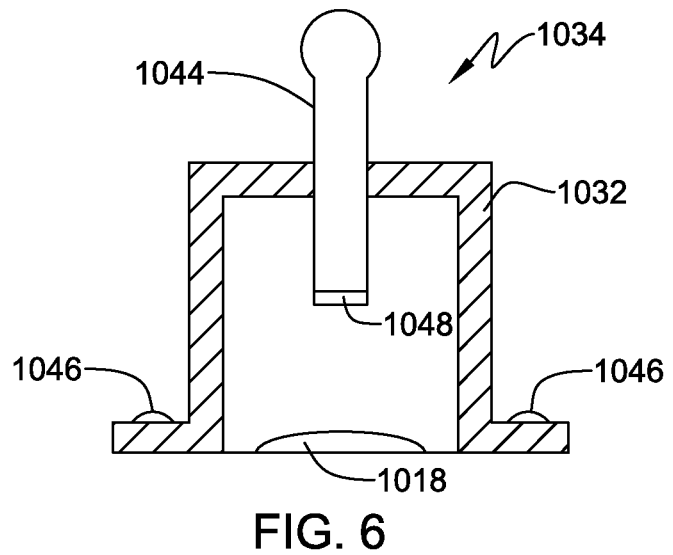
FIG. 6 is a cross-sectional view of the joystick of FIG. 5A.

Referring to FIGS. 3 and 4, in some embodiments, the joystick 1034 is positioned between a big toe 1040 and an index toe 1042 of the foot 1021. Referring to FIGS. 5-6, the joystick 1034 has a rod 1044 centered through and operatively connected to the housing 1032 such that rod 1044 has two degrees of freedom. The sensor 1018, as shown in FIG. 6, is positioned inside the housing 1032 and below rod 1044. While the dimensions of housing 1032 may vary, in the exemplary embodiment, it has dimensions small enough to fit comfortably between the user's big toe 1040 and index toe 1042 and small enough to fit inside footwear 1038. Housing 1032 may also include and/or have mounts 1046 so that joystick 1034 may be attached to the sole 1036 of footwear 1038. The dimensions of rod 1044 may vary, but in the exemplary embodiment, the rod 1044 may be long enough for the user to grasp it between the big toe 1040 and index toe 1042. In the exemplary embodiment, the joystick 1034 may be thick enough that when the user presses against it, the joystick 1034 will not break. Rod 1044 may be made of stainless steel or other durable material. A magnet 1048 may be placed at the end of rod 1044 disposed inside the housing 1032. The sensor 1018 may be connected to the sensor CPU 1019, shown in FIG. 2, which generates user input signals from the sensor data 1018. The sensor module communicator 1020 of the foot sensor module 1015 then transmits the user input signals to the device module 17, shown in FIG. 1A, through wired connections or wirelessly, for example, but not limited to, through Bluetooth®, RF communication, or other similar wireless connections. Sensor 1018 detects the position of rod 1044 and relays that information to the sensor CPU 1019, shown in FIG. 2. Sensor 1018 may be a cross-axial sensor or other similar sensor. The foot sensor module 1015 may impart wireless control to the prosthetic device 12, shown in FIG. 1A.

In the embodiment shown in FIGS. 2-6, the user grips rod 1044 with the big toe 1040 and index toe 1042 and presses against the rod 1044 to control a direction of movement of the prosthetic device 12, shown in FIG. 1A, or another associated device, such as movement of a mouse on a computer screen, movement of a car, or movement of other similar remote-controlled devices. The user may also move rod 1044 by placing the big toe 1040 on top of rod 1044 and pressing the rod 1044 in the desired direction. As the user moves rod 1044, sensor 1018 detects displacement of the magnet 1048 at the end of rod 1044, and thus detects the direction the user is moving rod 1044. That displacement information is then relayed to the sensor CPU 1019, which translates the movement of rod 1044 into a desired movement of the associated device. The sensor module communicator 1020 then communicates the displacement information to the device module 20, shown in FIG. 1A, which commands movement of the associated device. The foot sensor module 1015 has control of two degrees of freedom such as left and right, up and down, or forward and backward. The foot sensor module 1015 may also be used as a discrete switch, such as an on/off switch control a mode of the associated device, as will be discussed in greater detail below.

Figures 7A, 7B:
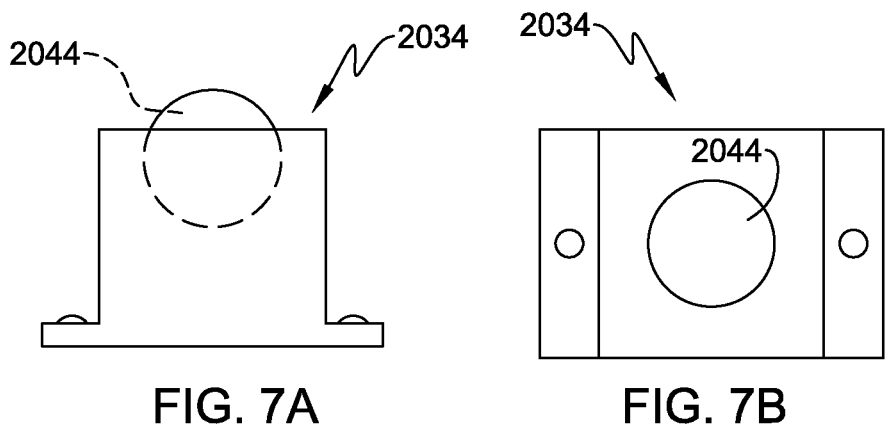
FIG. 7A is a side plan view of a rollerball joystick according to another embodiment of a motion reader for a foot sensor module of FIG. 1A.
FIG. 7B is a top plan view of the rollerball joystick of FIG. 7A.

Referring to FIG. 7, another embodiment of the foot sensor module 2025 may include a ball joystick 2034. The ball joystick 2034 includes a roller ball 2044 instead of the rod 1044. In this embodiment, the user may control the prosthetic device 12, shown in FIG. 1A, by moving the big toe 1040 across the roller ball 2044. For example, if the ball joystick 2034 is programmed to control left and right movement of a prosthetic arm, when the user presses the left side of roller ball 2044, the prosthetic arm will move to the left. Similarly, when the user presses the right side of roller ball 2044, the prosthetic arm will move to the right.

Referring to FIGS. 8A, 8B and 9, another embodiment of the foot sensor module 3015 is shown. In this embodiment, foot sensor module 3015 includes an inner sole 3036 having sole sensors 3018, positioned at various points on the inner sole 3036. The sole sensors 3018 may be of the type such as pressure sensors, force sensors, or the like. The sensors 3018 are affixed to an underside 3050 of the inner sole 3036. The device module 17, shown in FIG. 1A, may be programmed to control various functions of the prosthetic device 12, shown in FIG. 1A, based on the input from each sole sensor 3018. Although shown with multiple sole sensors 3018, as few as one sole sensor 3018 may be used, in which case the lone sole sensor 3018 may function as a discrete on/off switch (and in some embodiments where multiple sensors are used, one or more sensors 3018 may function as on/off switches). Those skilled in the art will appreciate that by adding more sole sensors 3018 to inner sole 3036, the difficulty in independently controlling the movement of and pressure applied to each sensor 3018 must be taken into consideration. Using two sole sensors 3018, the control apparatus 10, shown in FIG. 1A, will have two degrees of freedom, either up and down, left and right, forward and backward, open and close or other similar discrete function. Using four sole sensors 3018, the control apparatus 10, shown in FIG. 1A, will have four degrees of freedom with the ability to move forward, backward, left, and right or up, down, left, and right. Using six sole sensors 3018, the control apparatus 10, shown in FIG. 1A, will have 6 degrees of freedom with the ability to move up, down, left, right, forward, and backward. In various embodiments, one or more of these sensors 3018 may also function as discrete switches, for example, to allow the user to select various hand grips, as will be discussed in greater detail below.

In the exemplary embodiment shown in FIGS. 8A, 8B and 9, foot sensor module 3015 has four sole sensors 3018 placed on the underside 3050 of the inner sole 3036. FIG. 8B shows where the sole sensors 3018 are in relation to a user's foot 3021: one under the big toe 3040, one under the left side of the foot 3021, one under the right side of the foot 3021, and one under the heel of the foot 3021. The sole sensor 3018 under the big toe 3040 may control movement of the arm forward, the sole sensor 3018 under the left side of the foot 3021 may control movement of the arm to the left, the sole sensor 3018 on the right side of the foot 3021 may control movement of the arm to the right, and the sole sensor 3018 under the heel may control movement of the arm backward.

Figure 10A:
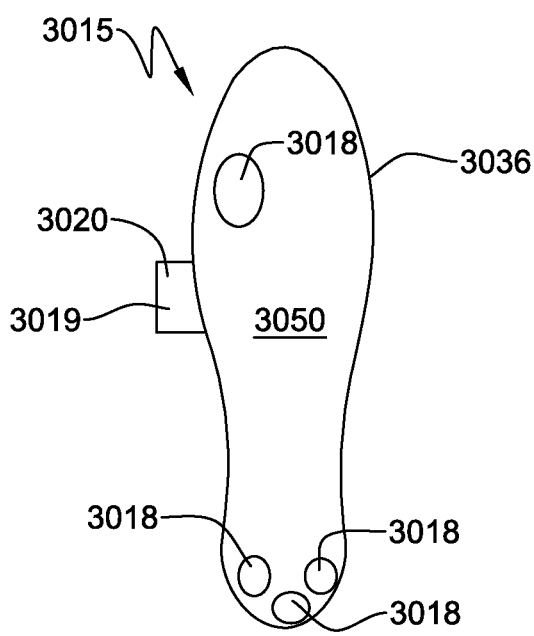
FIG. 10A is a top plan view of another embodiment of a foot sensor module.
Figure 10B:
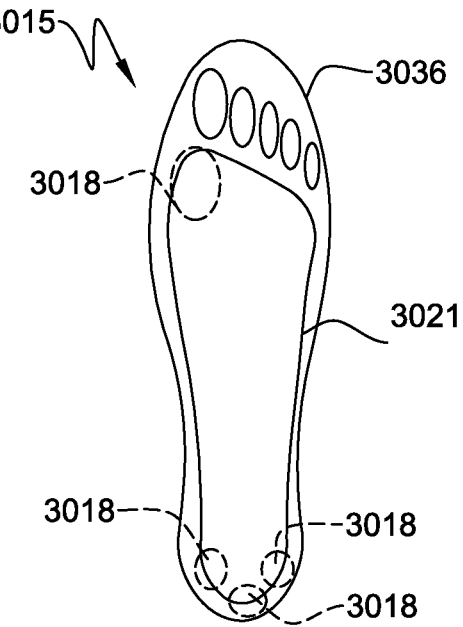
FIG. 10B is a top plan view the foot sensor module of FIG. 10A, showing where the sensors are placed in relation to the user's foot.
Figure 11A:
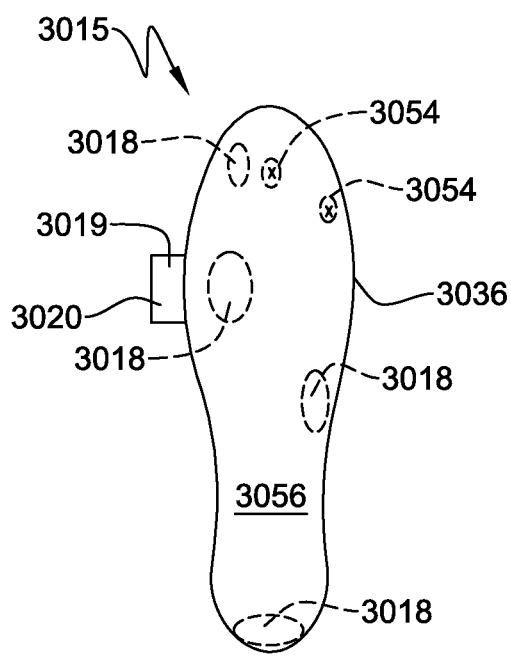
FIG. 11A is a top plan view of yet another embodiment of a foot sensor module.
Figure 11B:
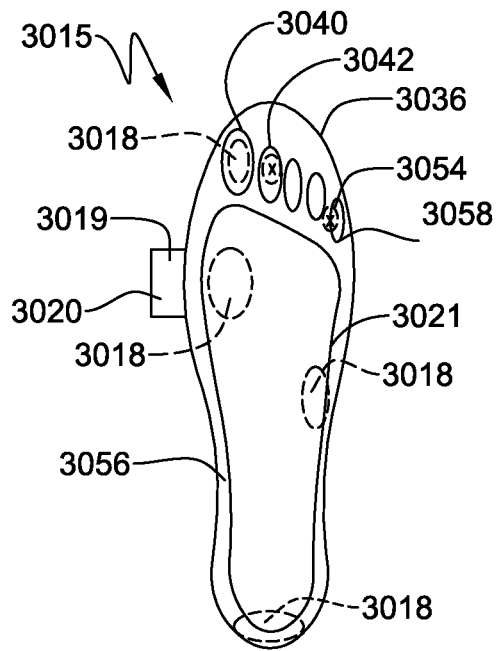
FIG. 11B is a top plan view of the foot sensor module of FIG. 11A, showing where the sensors are placed in relation to the user's foot.
Figure 12:
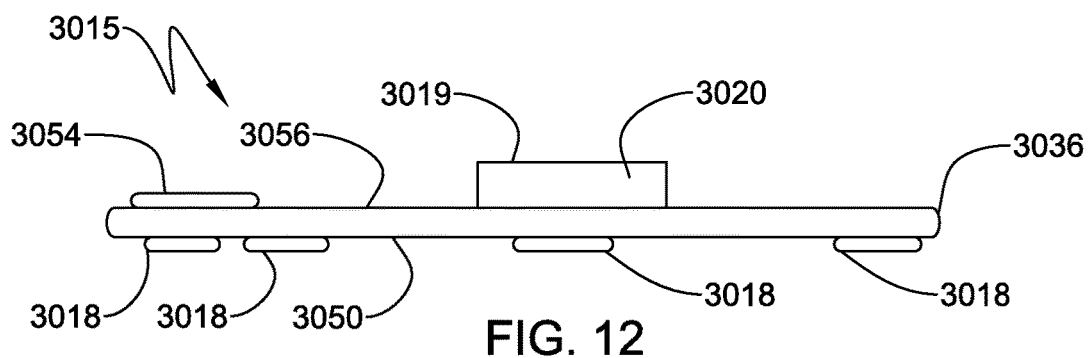
FIG. 12 is a side elevation view of the foot sensor module of FIG. 11A.
Figure 13:
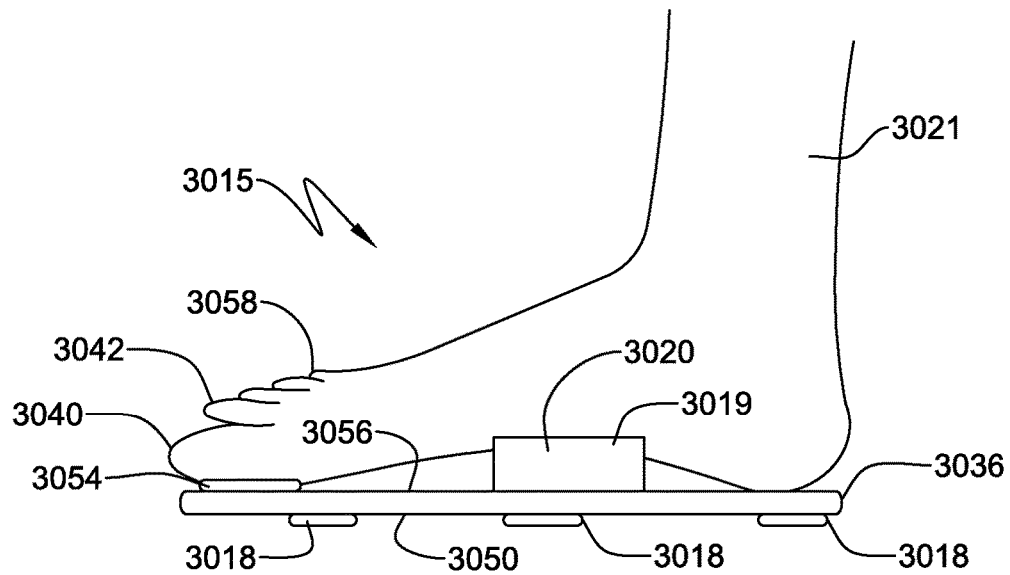
FIG. 13 is a side elevation view of the sensor module of FIG. 11B, showing where the sensors are in relation to the user's foot.

In alternative embodiments, the sole sensors 3018 could be placed under other parts of the foot 3021. For example, referring to FIGS. 10A and 10B, the underside 3050 of the inner sole 3036 might have one sole sensor 3018 under the ball of the foot 3021 and three sole sensors 3018 under the heel of the foot 3021.

Regardless of the sensor placement, in operation, the embodiments shown in FIGS. 8A-10 operate in a similar fashion. The sensor CPU 3019 receives input data from the sole sensors 3018 and filters and/or converts the data to generate user input signals. The user input signals are transmitted to the device module 17, shown in FIG. 1A, by the sensor module communicator 3020. The device CPU 26, shown in FIG. 1A, then calculates prosthetic device actuator commands based, at least in part, on the user input signals from the sensor module 3015 and commands the prosthetic controller 27, shown in FIG. 1A, to control the associated device, such as a mouse on a computer screen, a robot, or a prosthetic limb in accordance with the device actuator commands. Wires 3052, shown in FIG. 8A, may connect the sensors 3018 to the sensor CPU 3019, which may be attached to the shoe. The sensor module 3015 may be connected to the device module 17, shown in FIG. 1, by wires or wirelessly, for example, through a blue tooth device or other wireless communication system.

In operation, as the user presses down on the sole sensors 3018, a pressure or force pattern of the foot 3021 is created, depending on the sole sensor placement. The sensor module 3015 measures the change in pressure applied by the user, and relays the pattern to the device module 17, shown in FIG. 1. The device module 17, shown in FIG. 1A, translates the pattern into the prosthetic actuator command. For example, the device module 17, shown in FIG. 1A, may command movement of the associated device in the form of a velocity change or a position change using an equation, such as $\Delta P = \vec{V}_{to\ be\ changed}$ for velocity change or $\Delta P = X_{to\ be\ changed}$ for position. For example, with the foot sensor module 3015 of the embodiment of FIGS. 8A and 8B, if the user desires to move the prosthetic arm up, he might press down on the sole sensor 3018 that is below the big toe 3040. This creates a pressure pattern that is then relayed to the device module 17, shown in FIG. 1A, and translated into an upward movement of the prosthetic arm. If the user desires to move the prosthetic arm down, he might press down on the sole sensor 3018 under the heel, which creates a different pressure pattern that is relayed to the device module 17, shown in FIG. 1A, and translated into a downward movement of the prosthetic arm.

Although described for exemplary purposes as providing directional control, sole sensors 3018 may also provide proportional control. For example, with sole sensors 3018 that are pressure sensors or force sensors, the amount of pressure or force exerted on them may be translated into a speed at which the controlled device moves. Referring to FIGS. 8A, 8B and 9, for the foot sensor module 3015, if the user desires to move the prosthetic arm quickly across the body from left to right, he might heavily press sole sensor 3018 on the right side of inner sole 3036. Alternatively, if the user desires to move the prosthetic arm slowly across the body from left to right, he might lightly press sole sensor 3018 on the right side of inner sole 3036. Accordingly, the device actuator commands generated by the device module 17, shown in FIG. 1A, may vary depending on the magnitude of the pressure or force applied by the user to the sole sensors 3018, which is dissimilar to sensors that act only as switches, i.e., where no matter how hard the sensor is pressed, the output movement does not change.

With pressure sensors or force sensors, the user has better kinematic control of the prosthesis for smoother, less jerky, movements. The user is not limited to two movements of strictly up and down or left and right, but is rather able to control both the speed and direction of the movement. Additionally, the user may engage multiple sole sensors 3018 simultaneously to give a combined motion (e.g. up and left). For example, in the embodiment shown in FIGS. 10A and 10B, the foot sensor module 3015 has three sole sensors 3018 under the heel that control the left, right, and backward movement of the prosthetic device 12, shown in FIG. 1A. As the user rolls the heel across the sole sensors 3018 from right to left, the prosthetic device 12, shown in FIG. 1A, will move smoothly in a similar sweeping backward movement. Without these sole sensors 3018, the prosthetic device 12, shown in FIG. 1A, would first have to move from left to right, stop, and then move backward, resulting in a choppy motion.

Referring to FIGS. 11A-13, in an alternative embodiment of the foot sensor module 3015, the foot sensor module 3015 may additionally have top sensors 3054 placed on a topside 3056 of the sole 3036. This embodiment may have sole sensors 3018 on the underside 3050 of inner sole 3036 as well as the top sensors 3054 on the topside 3056 of inner sole 3036. In such an embodiment, top sensors 3054 may act as discrete or proportional switches and may be placed under toes or other parts of the foot 3021 that will not significantly affect the pressure or force readings of sensors 3018 on the underside 3050 of inner sole 3036. For example and still referring to FIGS. 11A and 11B, when used to control a prosthetic arm, top sensors 3054 act as mode switches, located on the topside 3056 of inner sole 3036 under the index toe 3042 and little toe 3058. The top sensor 3054 under the index toe 3042 may be pressed to signal the device module 17, shown in FIG. 1A, that the foot sensor module 3015 is in an arm mode or a bulk mode and will be moving certain actuators of the prosthetic arm, such as shoulder, humerus and/or elbow actuators, while locking other actuators in position such as finger and wrist actuators. The top sensor 3054 under the little toe 3058 may then be pressed to switch to a hand grasping mode, which signals the device module 17, shown in FIG. 1A, that the foot sensor module 3015 is being used to change the type of hand grasp by controlling finger and/or wrist actuators, while locking one or more of the bulk movement actuators in position. In other applications, such as using the foot sensor module 3015 to drive a cursor on a computer screen, these top sensors 3054 might be used to signal as left and right mouse buttons.

Figure 14:
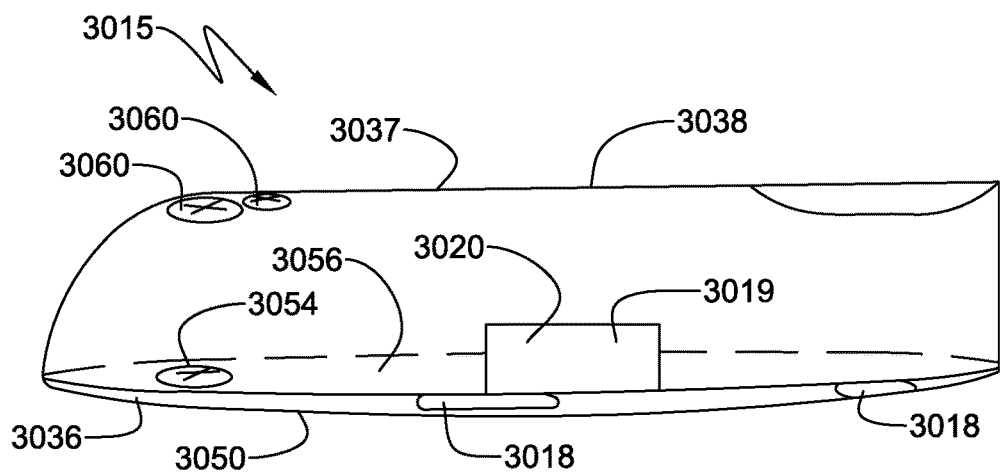
FIG. 14 is a side elevation view of yet another embodiment of a foot sensor module as it is placed inside a user's shoe.
Figure 15:
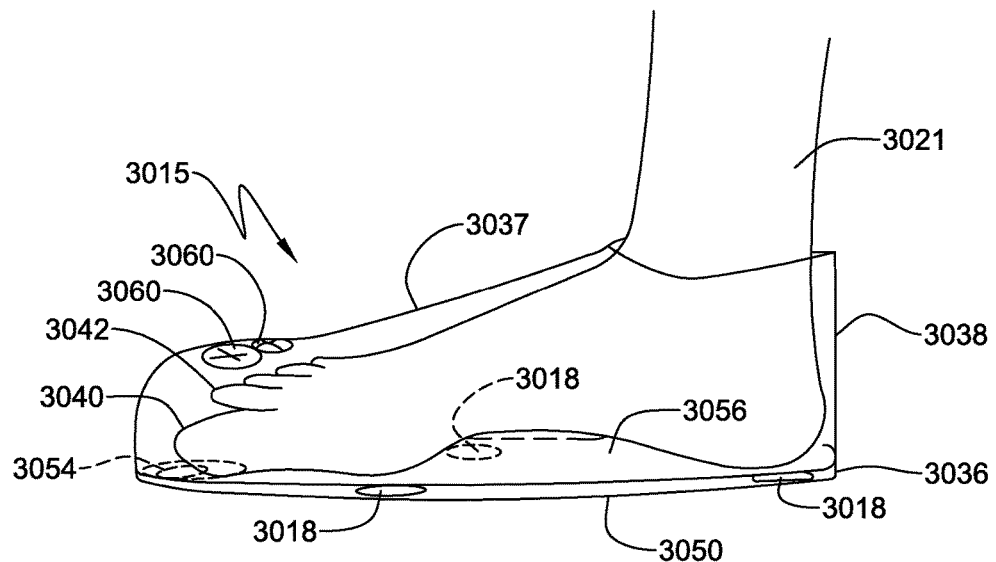
FIG. 15 is a side elevation view of yet another embodiment of a foot sensor module as it is placed inside a user's shoe, showing where the sensors are in relation to a user's foot.

Referring to FIGS. 14 and 15, another alternative embodiment of the foot sensor module 3015 utilizing sole sensors 3018 may additionally use shoe sensors 3060, which may be placed above the toes on an inner portion of a roof 3037 of footwear 3038. In such an embodiment, shoe sensors 3060 may act as discrete switches. For example, in addition to sole sensors 3018 on the underside 3050 of sole 3036, the foot sensor module 3015 may have the top sensor 3054 on the top surface of sole 3036 below the big toe 3040 and shoe sensors 3060 on the inner surface of the roof of the shoe 3038 above the big toe 3040 and index toe 3042. The top sensor 3054 and shoe sensors 3060 may be programmed to switch modes. For example, pressing the big toe 3040 up against the shoe sensor 3060 may set the device module 17, shown in FIG. 1A, to arm bulk mode or gross mode, wherein the foot sensor module 3015 may be used to control the bulk movement of the prosthetic arm as will be discussed in greater detail below. Alternatively, pressing the big toe 3040 down against the top sensor 3054 may set the device module 17, shown in FIG. 1A, to a wrist mode to control only the wrist of the prosthetic arm or to a finesse mode in which only the wrist and hand actuators are controlled. Once in the desired mode, the sole sensors 3018 could then be used to control desired movements of the prosthetic device 12, shown in FIG. 1A. The shoe sensors 3060 may also be used to control other features of a prosthetic, such as opening/closing a hand or acting as an on/off switch. Thus, a body input signal transmitted from a particular sensor of the foot sensor module 3015 could be used by the device module 17, shown in FIG. 1A, to command a variety of movements of the prosthetic device 12, shown in FIG. 1A, depending upon the selected mode.

Although the foot sensor module 3015 has been shown and described with respect to the detailed embodiments thereof, it will be understood by those skilled in the art that various changes in form and detail thereof may be made without departing from the spirit and scope of the invention. For example, the sensors may be attached to the inner lining of a sock or may be directly attached to a shoe.

Figures 16, 17:
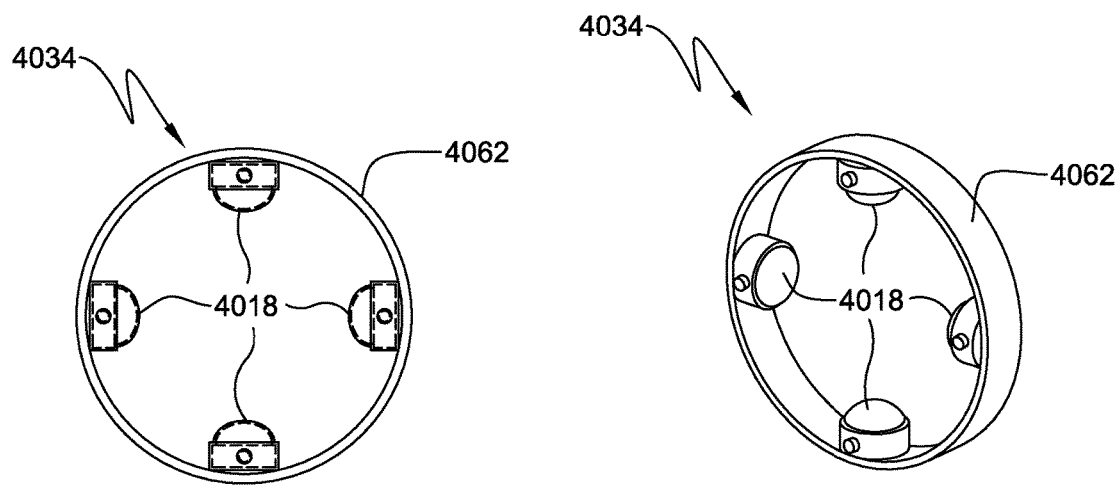
FIG. 16 is a side view of one embodiment of a residuum controller.
FIG. 17 is a perspective view of the residuum controller of FIG. 16.

Referring to FIGS. 16 and 17, in another embodiment, the sensor module 15 of the control apparatus 10 may include a residuum joystick 4034, having a frame 4062 and residuum sensors 4018. Referring to FIG. 18, in this embodiment, the residuum joystick 4034 may be attached to a prosthetic support 4064 so that a user's residuum (not shown) may extend into the residuum joystick 4034. The user may then control the prosthetic device 12, shown in FIG. 1A, by moving the residuum (not shown) to activate the residuum sensors 4018.

In this embodiment, as shown with four residuum sensors 4018 (although in various other embodiments, greater than four or less than four sensors may be used), the user may control the movement of the prosthetic device 12, shown in FIG. 1A, in two degrees of freedom, such as vertical movement and horizontal movement. Referring to FIG. 19, a residuum 4066 extends into the residuum joystick 4034 having residuum sensors 4018. As shown, the residuum 4066 is not in contact with the residuum sensors 4018, so the prosthetic device 12, shown in FIG. 1A, will remain stationary. As shown in FIG. 20, the user may generate body input signals transmitted from the sensor module 15, shown in FIG. 1A, to the device module 17, shown in FIG. 1A, by, for example, moving the residuum 4066 to engage the right residuum sensor 4018. The signal generated by engaging the right residuum sensor 4018 may be used by the device module 17, shown in FIG. 1A, to command the prosthetic device 12, shown in FIG. 1A, for example, the device module 17 may command the prosthetic device 12 to move to the right. Similarly, as shown in FIG. 21, the user may move the residuum 4066 forward and to the left, engaging two residuum sensors 4018 to signal the device module 17, shown in FIG. 1A, to move the prosthetic device 12, shown in FIG. 1A, up and to the left.

The residuum sensors 4018 may alternatively be used as discrete switches. For example, one residuum sensor may be used to switch between a bulk mode in which bulk movement of the prosthetic arm is controlled and a finesse mode in which only hand and wrist actuation of the prosthetic arm is controlled.

The residuum input may provide physical feedback to a user. Thus, adding to spatial and other types of feedback a user may experience. Thus, the residuum input may enhance the control by the user. The residuum input may also be used for proportional and/or position control.

Another embodiment of the control apparatus 10, shown in FIG. 1A, uses kinematic mapping, sensing head and body movement, to control the prosthetic device 12. The user moves the head and body in coordination to select a point in space where they desire the prosthetic device 12 to move. Head movement is slow, intentional and decoupled from a major function, which makes it ideal for prosthetic control. This kinematic mapping control may be a mode that may be selected by the user by, for example, but not limited to, a double click of a switch.

Figure 22:
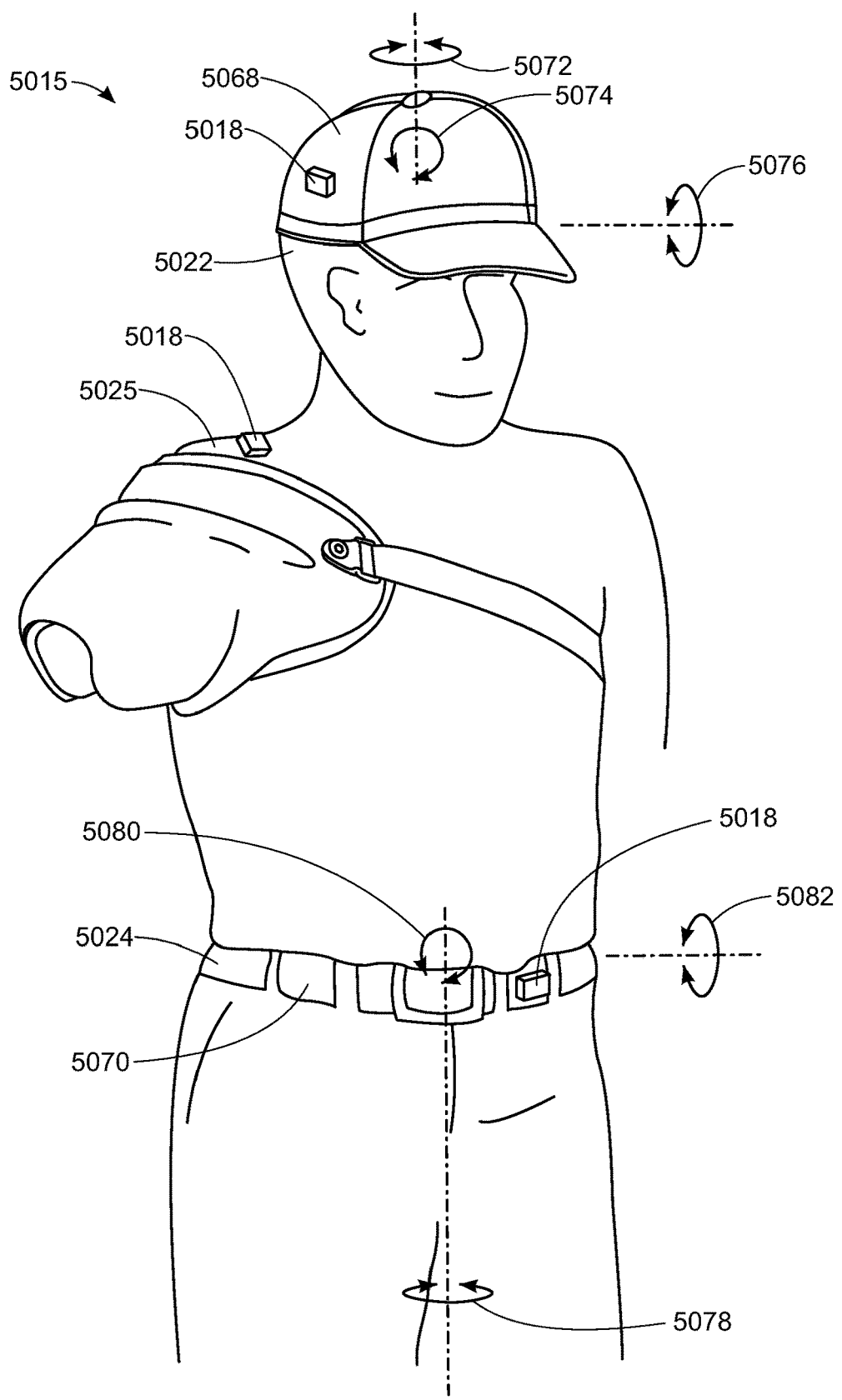
FIG. 22 is a front view of a kinematic mapping embodiment of the control apparatus.

Referring to FIG. 22, a kinematic mapping sensor module 5015 features three body sensors 5018 in three locations, the shoulder 5025, the head 5022, and the waist 5024. In this way, two body sensors 5018 are on the body of the user and the other body sensor 5018 is on the head 5022. For example, a hat 5068 may hold one body sensor 5018 or, alternatively, the head body sensor 5018 may be mounted above an ear as a separate wireless unit. One body sensor 55018 may be incorporated into a belt 5070 or a pack (not shown) strapped onto the midsection of the user and another body sensor 5018 may be included on a prosthetic support 5071 mounted to the user's shoulder 5025.

This embodiment uses inertial sensors as body sensors 5018. These three body sensors 5018 may be used to detect up to six multiple degrees of freedom. Specifically, the body sensors 5018 may detect head yaw 5072, head roll 5074, head pitch 5076, torso yaw 5078, torso roll 5080 and torso pitch 5082. Additionally, theses body sensors may detect x, y, and z plane positioning. These sensors may also act as velocity acceleration gyros, accelerometers, angular velocity and magnetometers. Although shown as inertial sensors, the body sensors 5018 may also be shape sensors that may detect body flex.

Still referring to FIG. 22, in this embodiment of the sensor module 5015, the control apparatus 10, shown in FIG. 1A, assumes a fixed point of rotation at the middle of the prosthetic hand and creates a reference sphere around the fixed point. User preference determines the location of the fixed point by allowing the user to zero out the system with specific body input sensed by body sensors 5018, such as looking around. Then the user looks at a point, about which the sphere is created. By choosing where the fixed point of rotation is, the user customizes and orients the movement path. To select the fixed point and sphere, head 5022 rotation specifies an angle and body lean or shoulder 5025 rotation specifies radius.

Although the various embodiments of sensor modules 15 have been described separately herein for simplicity, it should be understood by those skilled in the art that the various embodiments may be used in combination to achieve the desired prosthetic control. For example, the foot sensor module 3015, shown in FIG. 9, may be used in conjunction with another sensor module (and/or control system), such as an inertial sensor module (and/or control system), a shoulder joystick, and/or an EMG sensor module (and/or control system).

Referring back to FIG. 1A, as discussed above, the device module 17 may use the body input signals from the sensor module 15 to control the prosthetic device 12 in a variety of different control modes, selectable by the user, to achieve different functionalities from the prosthetic device 12. For example, a control method of the prosthetic device 12 may include a bulk mode and a finesse mode. Bulk mode includes movement of the prosthetic device 12 into the general vicinity desired by the user, for example, by moving the palm of the prosthetic hand to a desired point in space. Thus, for example, bulk mode for a prosthetic arm may include actuation of the shoulder, humerus and/or elbow actuators and/or wrist. The terms bulk movement, gross movement and gross mode as used herein are synonymous with the term bulk mode.

Finesse mode in this embodiment relates to the ability to manipulate an object (not shown) and specifically relates to operating a prosthetic hand and a prosthetic wrist. Finesse mode may be used to achieve wrist rotation, inflection, deviation and hand gripping. Thus, the finesse mode allows the prosthetic hand to grasp or grip the object. A grasp or grip refers to an orientation of the prosthetic hand's overall hand pattern, as will be discussed in greater detail below. The grip may be activated by the user to hold and manipulate the object. The terms finesse movement, fine movement and fine mode as used herein are synonymous with the term finesse mode.

The current method uses bulk movement to allow the user to position the prosthetic arm at a specific point in a three-dimensional space (x, y, and z components). Once the prosthetic arm has reached the desired location, i.e. the specific point, finesse movement allows the user to manipulate the prosthetic hand and grip the object.

Both bulk and finesse movements are determined using the various control apparatuses described herein. The user determines a point that they want the prosthetic arm to reach and relative to a control input, the prosthetic arm moves to that point in space. This type of bulk movement results in simultaneous degree of freedom movement.

For example, in an embodiment with head control, the head moves and controls one joint of the prosthetic arm, resulting in one action. The input is head movement; the output is movement of the prosthetic arm. Similarly, referring back to FIG. 15, in an embodiment having the foot sensor module 3015, the user may apply pressure with different parts of the foot 3021 to sensors 3018, to control the bulk movement of the prosthetic arm. The user may then engage the shoe sensor 3060 to switch from bulk movement to finesse movement, and then use sensors 3018 to control the finesse movement of the prosthetic arm. This method allows the user to alternate between bulk movement and finesse movement.

In one embodiment, the device module 17 commands shoulder deflection and extension, elbow flexion and extension, and humerus rotation of the prosthetic arm in bulk mode. Additionally, depending on the severity of the amputation, shoulder abduction and adduction may also be controlled in bulk mode. In finesse mode, the device module 17 may command wrist rotation flexion, deviation and extension, and hand manipulation, including thumb and finger movement. In finesse mode, pressure and force sensors measure the distribution of weight and may be used to detect input specific to the grasp. The distribution of weight on the foot sensors may deliver specific input allowing the device module 17 to select the desired grip. Alternatively, in another embodiment, head position may be used to select the grip.

Although described with regard to a shoulder disarticulation amputee, it should be understood by those skilled in the art that the control systems and methods described herein may be adapted to be used for any prosthetic strapped onto the body. For example, for an elbow joint disarticulation amputee (direct control of just elbow joint) finesse control may be used for wrist and hand manipulation.

In some embodiments, the control apparatus 10 may include other modes, such as: an off mode, a home mode, and a hold mode. Any of the various sensors described herein may be programmed for mode selection.

In the home mode, the prosthetic device 12 is in a preset location, such as by the side of the user and the device module 17 is not sending any commands to the prosthetic device 12. Thus, the prosthetic device 12 is not moving. In the hold mode, the prosthetic device 12 maintains a fixed position. The term standby mode has also been used herein and is synonymous with hold mode. In one embodiment, the hold position appears as though it is not receiving any input, but rather, the last position data is continuously sent to the prosthetic device 12 to actively maintain the position.

In an alternative embodiment of the hold mode, a hold command may be sent that engages various brakes within the prosthetic device 12, rather than continually sending the same coordinates, freeing the system to do other functions instead of continuously calculating the last position. This improves the control apparatus 10 by conserving power. In some embodiments, the hold command may be executed on a degree-of-freedom/degree-of-freedom basis, allowing specific breaks for specific joints within the prosthetic device 12 to be engaged, while other joints remain free to move. This may, for example, in some embodiments, advantageously allow the user to grab something with the hand of the prosthetic device 12 by first engaging an elbow brake and then opening and closing the hand with the elbow remaining stationary. As another exemplary embodiment, the user may similarly engage the elbow brake and then move the shoulder while not disengaging the elbow. Thus, in some embodiments, various degrees of freedom may be enabled and/or shut-off depending on user preference/user command.

Figure 23:
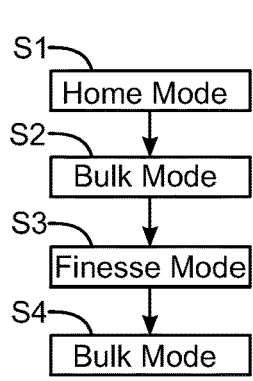
FIG. 23, is one method of control of a prosthetic device.

Referring to FIG. 23, one embodiment of the control method of the control apparatus 10 includes operating the prosthetic device 12 in home mode S1, then in bulk mode S2, then in finesse mode S3, and then in bulk mode S4. This allows the user to enter bulk mode and move the prosthetic arm to the desired location, then enter finesse mode to move the prosthetic hand and wrist to manipulate the object as desired, and then return the arm to home mode.

Figure 24:
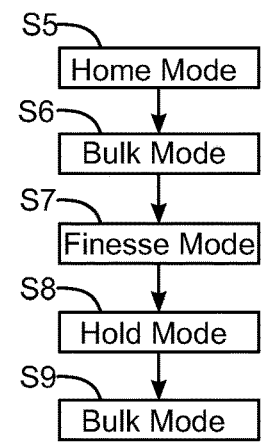
FIG. 24 is the method of control of the prosthetic device according to FIG. 23 with an additional holding step.

Referring to FIG. 24, an additional embodiment may include operating the control apparatus 10 in home mode S5, then in bulk mode S6, then in finesse mode S7, then in hold mode S8, and then in bulk mode S9. This allows a user to move the prosthetic arm to the desired location and manipulate the object, then the user is able to hold the object in the desired position before the prosthetic arm is returned to home mode.

Figure 25:
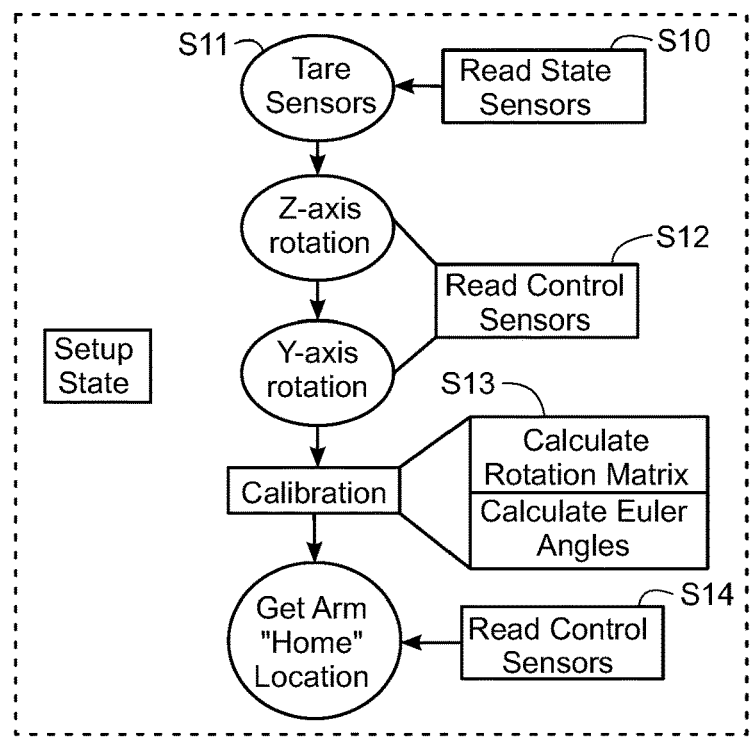
FIG. 25 is a schematic diagram of a control method during a setup state.

Referring to FIG. 25, in these embodiments having sensors 18, a person using the control apparatus puts the prosthetic arm on and simple setup state procedure is executed to quickly calibrate the prosthetic arm. For instance, orientation sensors in the prosthetic arm may provide position information to the device module 17 to identify the starting position of the prosthetic arm S10. The device module 17 then tares the sensors 18 to zero them out, so that their rotations are in respect to their tarred position S11. The body sensors are then read to get the user's perceived Z and Y axis S12. A calibration step is then run where the Z axis is projected on the normal plane with the Y axis to get the X axis S13. The body sensors are then read again to identify the coordinates for the home mode S14. Then the control apparatus 10 is ready to be operated.

Figure 26:
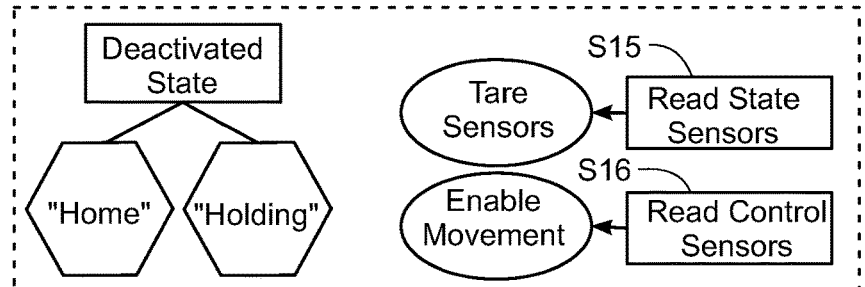
FIG. 26 is a schematic diagram of a control method during a deactivated state.

Referring to FIG. 26, when the control apparatus 10 is in a deactivated state such as in home mode or hold mode, prior to enabling movement, the device module 17 may use transformation sensors in the prosthetic arm to tare the body sensors to zero them out, so that their rotations are in respect to their tarred position S15. The body sensors are then read to get the user's perceived Z and Y axis, and the Z axis is projected on the normal plane with the Y axis to get the X axis S16. Once the perceived axes are known, the sensors 18 are activated and may be used in bulk mode and/or finesse mode. The transformation sensors use the fixed point of the cylindrical mapping system and the lengths of each prosthetic arm component to determine when the arm has achieved the desired point in space. In various other embodiments, a spherical mapping system and/or a Cartesian coordinate system may also be used.

Figure 27:
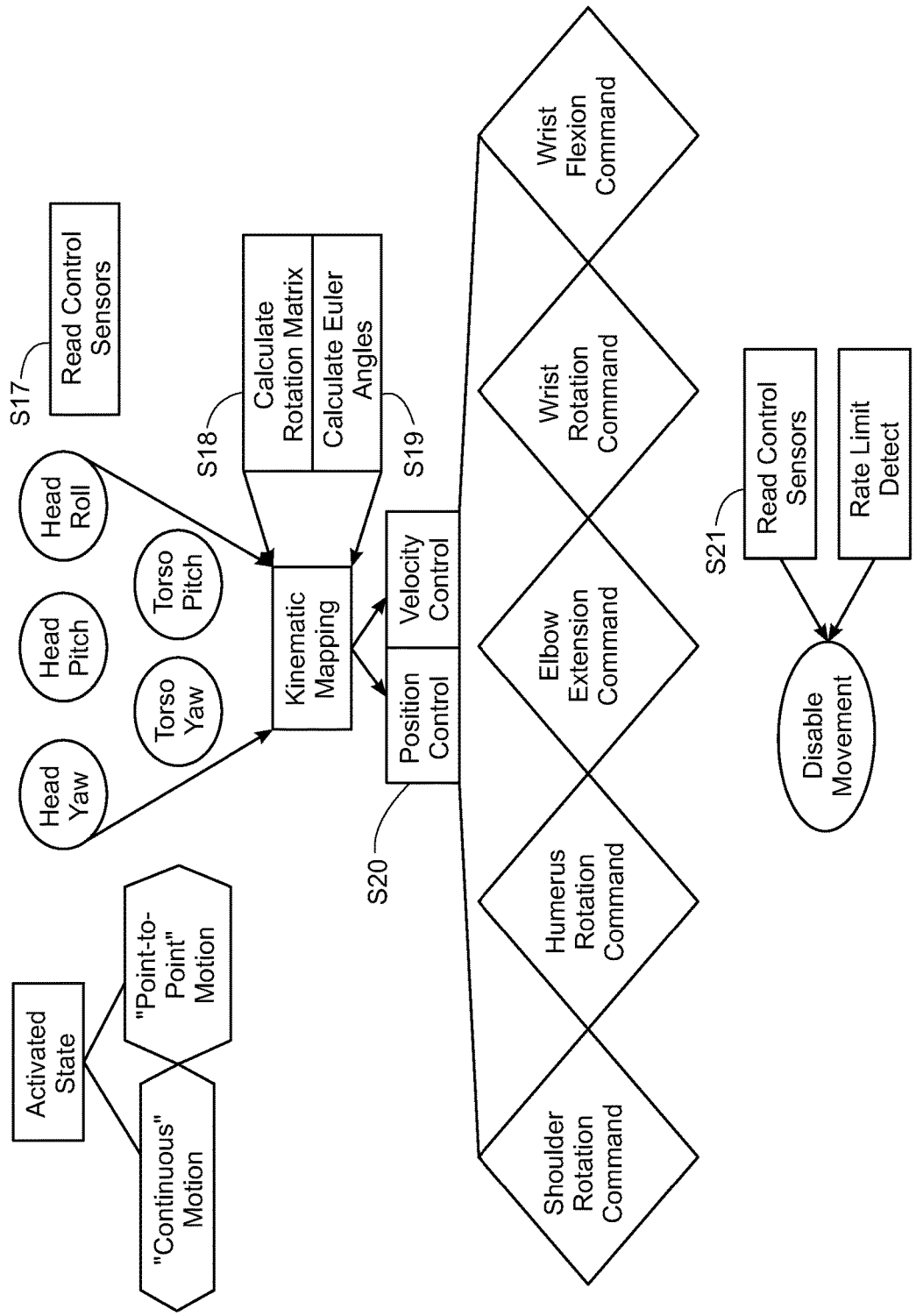
FIG. 27 is a schematic diagram of a control method during an activated state.

Referring to FIG. 27, a control method for embodiments using kinematic mapping, such as that shown in FIG. 22, is shown. When the sensors have been activated, the sensors identify the desired coordinates for the prosthetic arm to move to S17. Once the fixed point is specified, the device module 17 goes through equation calculations (which in some embodiments, may include quadratic equation calculations) to calculate the best velocity and direction vector for getting the target sphere and/or coordinate and/or point in three-dimensional space to line up correctly S18. The device module 17 then goes through dot products to determine the necessary angles for the shoulder, elbow and humeral prosthetic movement S19. Based on those calculated angles, the arm is moved to reach the target sphere S20. Once the sensors determine that the target sphere has been reached, the arm movement is stopped S21.

In an alternative embodiment utilizing kinematic mapping, there is a click and go mode. Thus, in the click and go mode, if the user wants to move the prosthetic device 12 to an object, they may look at a point in space where they want the prosthetic device 12 to go, and then engage a sensor, such as residuum sensor 4018 shown in FIG. 19, that activates the click and go mode. Once activated, the body sensors determine where the head was looking and where the body leaned, and coordinates are sent directing the prosthetic device 12 to go to that location. Click and go mode may use the same sensor set for controlling bulk movement as finesse movement. For instance, once the bulk movement begins, the head sensor 5018 may then control the finesse movement.

In another embodiment, by using accelerometers and body sensors 5018, the control apparatus 10, shown in FIG. 1A, is able to identify the center of gravity in relation to the body sensor 5018 on the shoulder. From that, the device module 17, shown in FIG. 1A, sending angle commands to the prosthetic arm knows where the end of prosthetic arm is and knows where the gravity vector with respect to the end of the arm is. Therefore, the device module 17, shown in FIG. 1A, may rotate the wrist with respect to the gravity vector to maintain an object (not shown) within the prosthetic hand in an upright position. In some embodiments, the control apparatus 10, shown in FIG. 1A, may use this information to move the prosthetic hand based on shoulder position. In some embodiments, this control may be independent of gravity, e.g. the prosthetic hand may be moved based solely on shoulder position, while in other embodiments, the control apparatus 10, shown in FIG. 1A, may move the prosthetic hand both perpendicular to gravity and according to shoulder position.

In an alternate embodiment using body sensors, the user could put the sensor on only their head, using the sensor to three-dimensionally map the desired movements. This would decrease the number of sensors required to control the prosthetic.

The control apparatus 10 may control sensitivity of movement in that the device module 17 may vary the degree that sensor input is translated to movement output. Additionally, The sensor input may be required to meet a threshold value before movement output is sent to the prosthetic.

In some embodiments, there may also be an arm swing mode, allowing the prosthetic arm to move in harmony with the body while walking. When the user is going to use the arm, it is in the home/off position, and swing mode may be activated by engaging a sensor 18 or by detecting a specific motion or orientation with the body sensor 5018. In some embodiments, swing mode may also be activated by a manual switch and/or lever disengaging mechanical engagement of a portion of the prosthetic device 12.

Switching modes or selecting commands may be accomplished by engaging sensors 18 acting as discrete switches, by specific body motion such as ticks or head movement, by standard EMG signals using EMG electrodes, by shoulder or back movements, or by any other similar switching mechanism that may be programmed into the control apparatus 10 including, but not limited to, macros and/or other commands beyond direct kinematic movement or mode.

The sensors 18 may be disposed in various locations for detecting body input 16 to control the movement of the prosthetic device 12, such as in footwear. The control apparatus 10 may utilize wireless communication between the sensors 18, the sensor module 15, the device module 17 and the prosthetic device 12, simplifying the control apparatus 10 for the user. The sensors 18 may act as discrete switches to control operational modes of the prosthetic device and/or the control apparatus 10 may move the prosthetic device 12 proportionally to the body input 16 sensed by the sensors 18. The sensors 18 may also be disposed in a prosthetic support apparatus 4064, allowing user to provide body input 16 to the sensors 18 with the residuum 4066.

Each sensor 18 may sense a variety of body inputs 16 such as pressure and rate of pressure change. Therefore, body input 16 from one sensor 18 may be translated by the device module 17 into multiple forms of movement information, such as direction and speed of movement.

Figure 28:
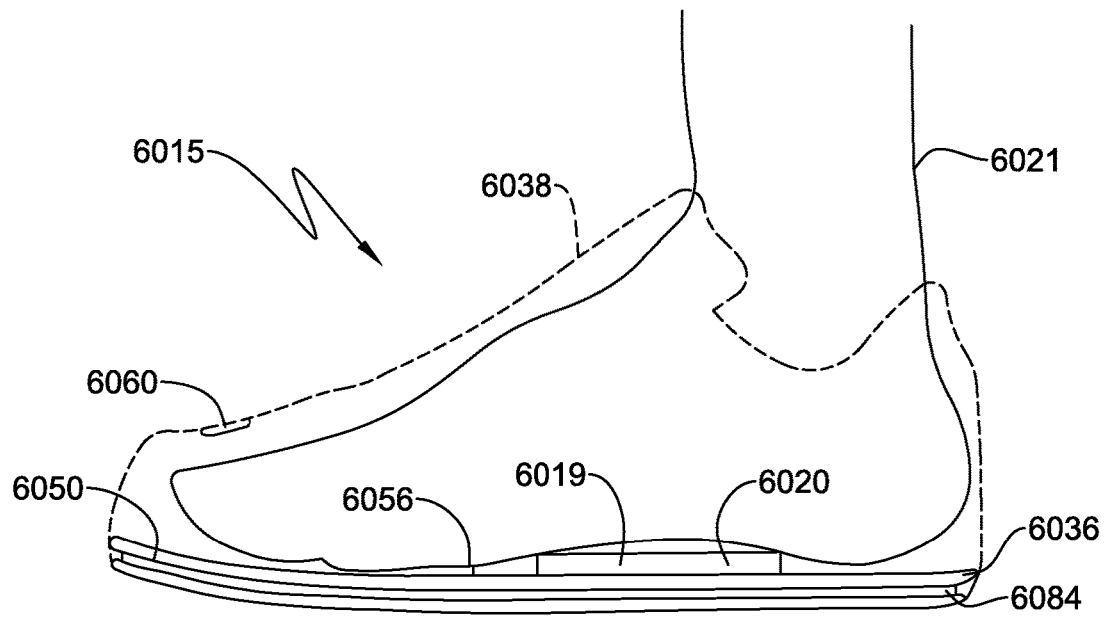
FIG. 28 is a side view of a foot sensor module according to yet another embodiment of the present invention.

Referring to FIG. 28, in various embodiments, rather than a series of discrete sensors 3018 as shown in FIGS. 8A-15, a sensor grid 6084 may be included in footwear 6038 to generate a pressure profile for the user's foot 6021. The sensed pressure profile may be sent by the sensor CPU 6019 to the device module 17, shown in FIG. 1A, and used by the device module 17, shown in FIG. 1A, to command the prosthetic device 12, shown in FIG. 1A. Thus, by changing the pressure profile of the foot 6021, the user may be able to command different functions from the prosthetic device 12, shown in FIG. 1A. Although shown on the underside 6050 of the inner sole 6036, the sensor grid 6084 could also be include on the topside 6056 of the inner sole 6036 or could be integral with the inner sole 6036.

Figures 29, 30:
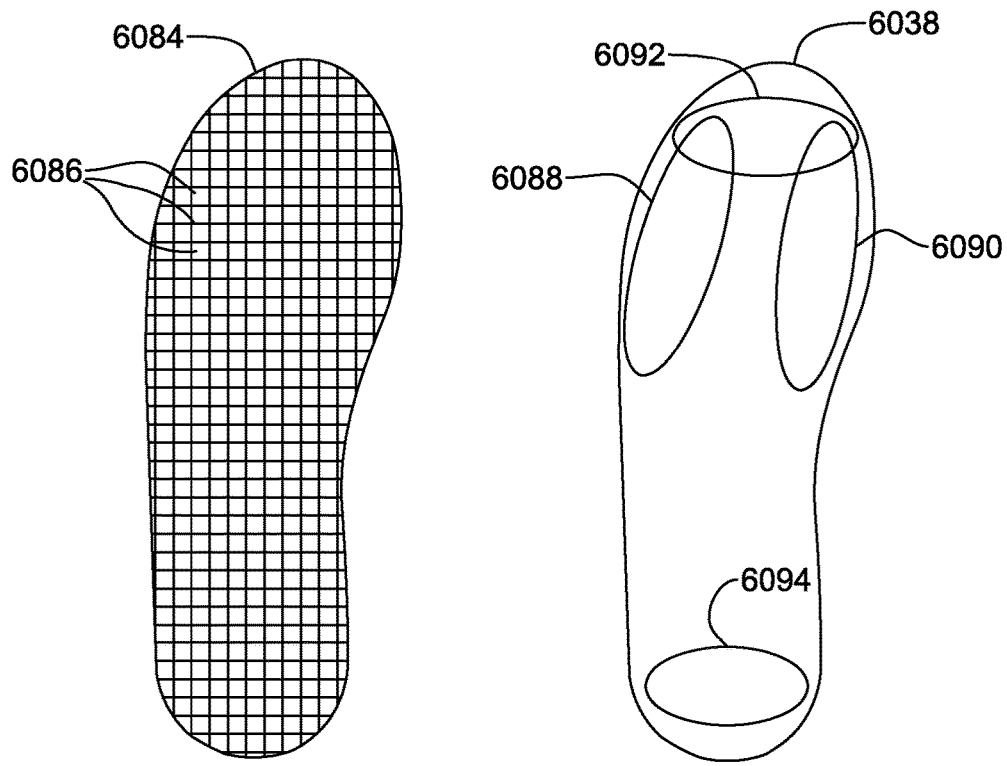
FIG. 29 is a top view of a sensor grid of the foot sensor module of FIG. 28.
FIG. 30 is a top view of a pressure profile generated by the sensor grid of FIG. 29.

Referring to FIG. 29, the sensor grid 6084 includes a plurality of zones 6086 in which pressure may be detected, to generate the pressure profile for the user's foot 6021, shown in FIG. 28. For example, force sensing resistors may be used to form the plurality of zones 6086, thereby allowing the pressure on each zone to be detected separately. In addition to force sensing resistors, in other embodiments, other pressure or force sensors may be used to form the plurality of zones 6086, for example, strain gauges, air bladders and any other similar force sensors.

Referring to FIG. 30, the pressure profile may show that region 6088, on one side of the user's footwear 6038, has higher pressure relative to that of region 6090, on the opposite side of the user's footwear 6038. This pressure profile may be used to command a particular motion from the prosthetic device 12, shown in FIG. 1A, for example, the pressure profile may move the prosthetic device 12, shown in FIG. 1A, to the right. Similarly, a pressure profile with a higher relative pressure in region 6090 to that of region 6088 may be used to command a different motion from the prosthetic device 12, shown in FIG. 1A, for example, movement of the prosthetic device 12, shown in FIG. 1A, to the left. The pressure profile may also show that region 6092, at the front of the user's footwear 6038, is greater or lower than the pressure of region 6094, at the rear of the user's footwear 6038. Thus, the pressure profile of the front relative to the rear of the user's footwear 6038 may be used by the device module 17, shown in FIG. 1A, to provide the prosthetic device 12, shown in FIG. 1A, with two additional degrees of freedom, such as forward and rearward motion. Various pressure profiles detected by the sensor grid 6084 may also be used as switches; for example, a pressure profile with a high pressure in region 6090 relative to region 6088 may be used to change between modes, such as bulk mode and finesse mode. Similarly, different pressure profiles may be used to select hand grips or to scroll through a list as will be discussed in greater detail below.

Thus, referring back to FIG. 28, the sensor grid 6084 provides the controller apparatus 10, shown in FIG. 1A, with the ability to control movement of the prosthetic device 12, shown in FIG. 1A, in at least two degrees of freedom, to control multiple switches or to control some combination of movement and switching. This embodiment may be more desirable than the embodiments with multiple sensors 3018, shown in FIGS. 8A-15, since in the multi-sensor approach the user's foot 6021 may move around in the footwear 3038, shown in FIG. 15, making it more difficult for the user to locate and activate the sensors 3018. The sensor grid 6084 overcomes the issue of sensor location and activation, by using variations in the pressure pattern formed by the user's foot 6021 to command the prosthetic device 12, shown in FIG. 1A. Thus, the user must only shift weight in a desired direction to change the pressure profile, rather than locating discrete sensors within the footwear 6038. Additionally, using pressure pattern recognition, the device module 17, shown in FIG. 1A, may determine the direction the user's weight is being shifted, thereby allowing small movements to be detected so that the user is not required to exaggerate their movements; rather, the sensor grid 6084 will sense small or micro movements and command the prosthetic device 12, shown in FIG. 1A, accordingly. Additionally, in various embodiments, the sensor grid 6084 may be implemented along with shoe sensors 6060 for the use as discrete switches as discussed above.

Figure 31A:
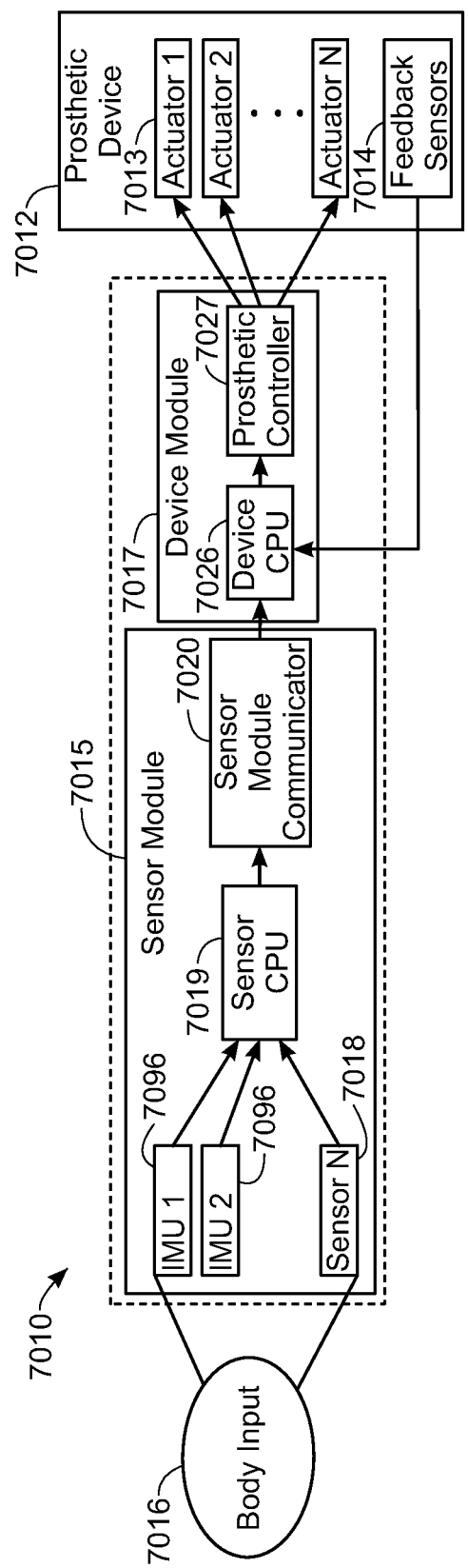
FIG. 31A is a schematic diagram of a prosthetic control apparatus according to another embodiment of the present invention.
Figure 31B:
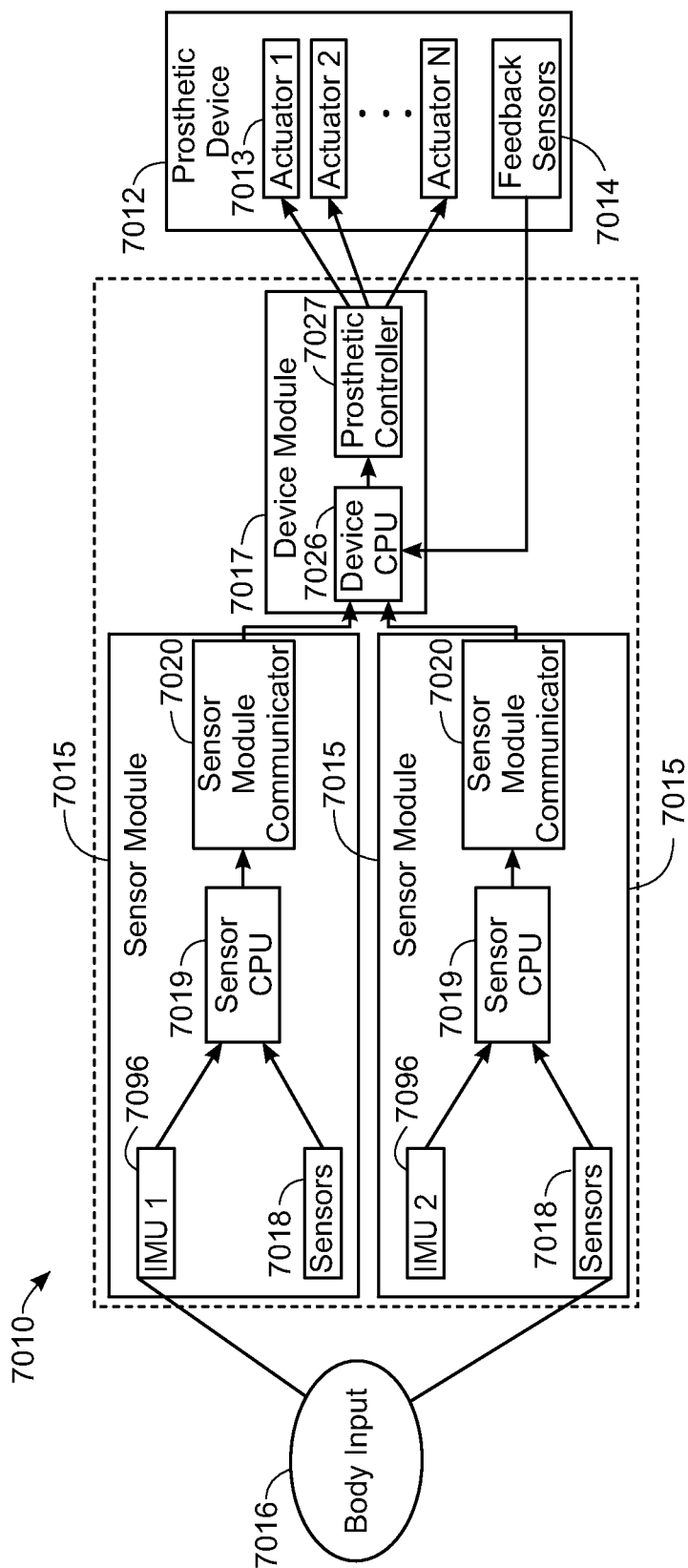
FIG. 31B is another embodiment of the prosthetic control apparatus of FIG. 31A.

Referring to FIG. 31A, the sensor module 7015 of the control system 7010 may include one or more Inertial Measurement Units (IMUs) 7096 in place of, or in addition to, the one or more sensors 7018. The one or more IMUs 7096 detect orientation, as will be discussed in greater detail below, which may be transmitted to device module 7017 for commanding the associated prosthetic device 7012. Thus, by altering the orientation of the IMU 7096, the user may control the prosthetic device 7012 in a desired manner. Referring to FIG. 31B, in some embodiments where multiple IMUs 7096 are attached to different body parts, it may be desirable to provide separate sensor modules 7015 for each IMU 7096 to decouple to IMUs 7096 from each other. In these embodiments, each sensor module 7015 may communicate with the device module 7017 and the device module 7017 uses the body input signals provided from each sensor module 7015 to command the associated prosthetic device 7012.

Figure 32:
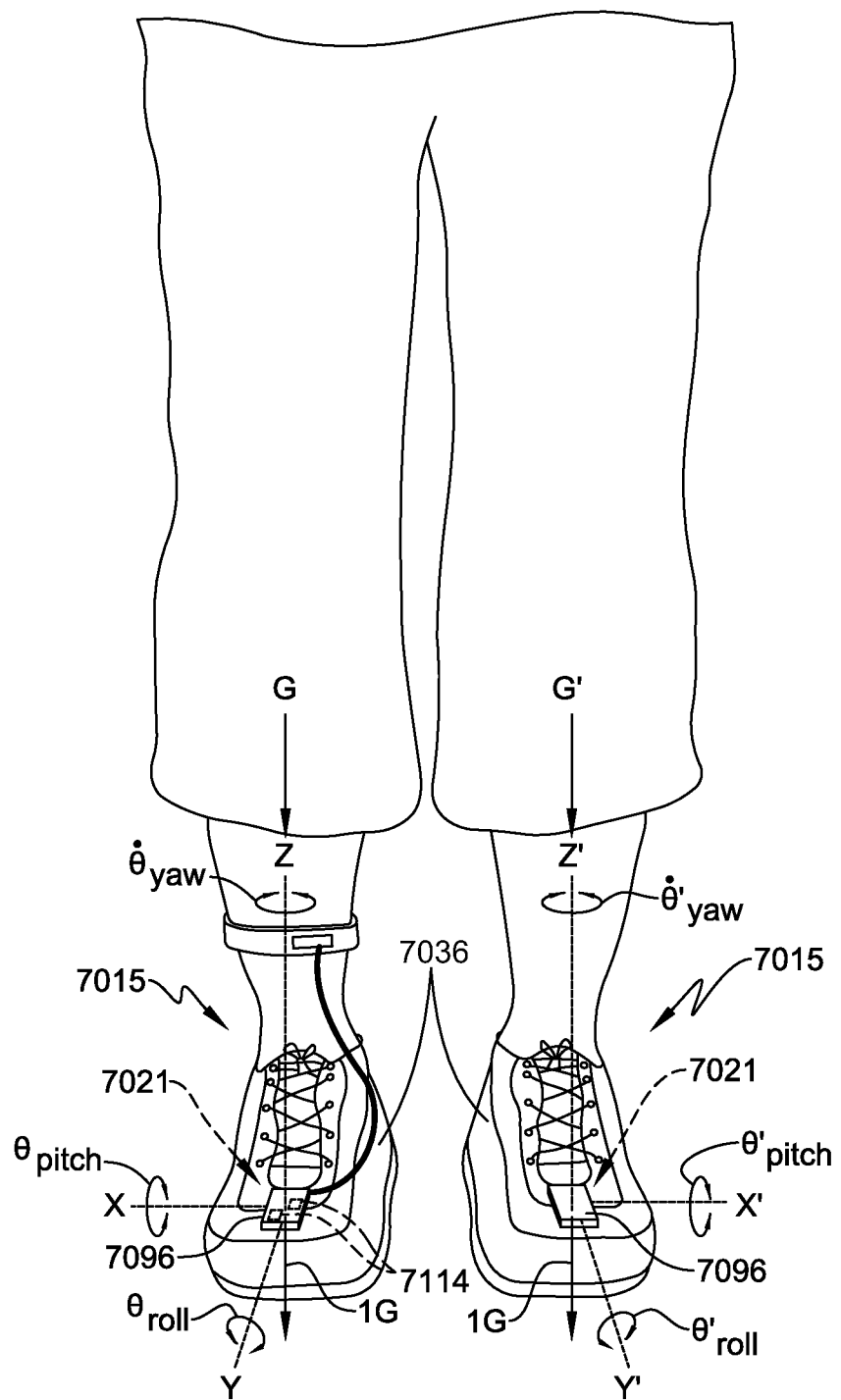
FIG. 32 is a front perspective view of two sensor modules of FIG. 31B being used by a user.

Referring to FIG. 32, in some embodiments, the IMU 7096 may determine the orientation of the user's foot 7021. In some embodiments, particularly where an increased number of control inputs is desired, one IMU 7096 may be used on each foot 7021 of the user (the term "feet" or "foot" is a general description, in some embodiments, the IMU 7096 may be placed on a user's ankle or ankles or on the user's leg or legs. In some embodiments, the IMU(s) 7096 may be placed on any part of a user indicative of the movement of the foot/feet, including, but not limited to, affixed to the user's clothing or footwear 7036). In some embodiments, IMUs 7096 may be placed at other locations on the user including but not limited to the user's arm, head, or the like. Each IMU 7096 is a device capable of sensing motion using a combination of sensors as will be discussed in greater detail below.

Figure 33:
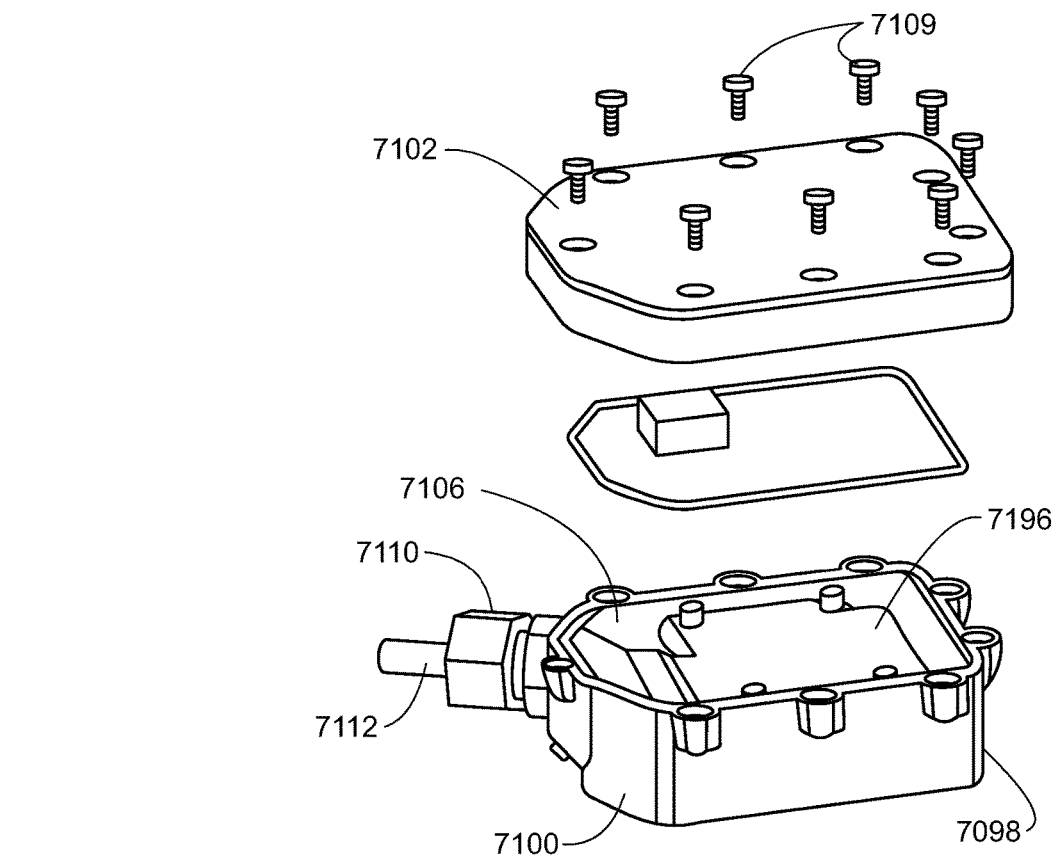
FIG. 33 is a exploded perspective view of a housing for an inertial measurement unit according to an embodiment of the present invention.

Referring to FIG. 33, in some embodiments, the IMUs 7096 may be a commercially available unit such as a MICROSTRAIN® 3DM-GX1® by Microstrain, Inc., Williston, VT. In some embodiments, a variety of other inertial measurement units may be implemented, such as those described in U.S. Pat. No. 8,453,340, issued Jun. 4, 2013, which is hereby incorporated by reference in its entirety. In these embodiments, the IMU 7096 may be accommodated in a housing 7098 having a base 7100 and a cover 7102, which interface to enclose the IMU 7096 within a housing cavity 7106. The cover 7102 may be connectable to the base 7100 by a plurality of screws 7109 or other known fastening means, such as a snap fit, one or more latches, or the like. In the exemplary embodiment the housing 7098 may measure approximately 0.61 in.×0.65 in.×0.22 in. The base 7100 of the housing 7098 may include an electronics orifice 7110, through which the IMU 7096 within the housing 7098 may be connected to the sensor CPU 7019 and the sensor module communicator 7020, shown in FIGS. 31A and 31B, for example, through one or more wires 7112. The one or more wires 7112 may also connect the IMU 7096 to a battery (not shown) for powering the IMU 7096. In some embodiments, the IMU 7096 may include a receiver (not shown) electrically coupled to the battery (not shown) to facilitate wireless charging of the battery (not shown) using a wireless charging mat (not shown) or the like. In such embodiments, the IMU 7096 preferably includes a light emitting diode (LED) (not shown) or similar indicator for notifying the user that the battery (not shown) is fully charged and/or to indicate to the user the battery charge state. In some embodiments, the LED (not shown) may be located within the housing 7098 and at least a portion of the housing 7098 may be translucent to allow the LED (not shown) to shine therethrough. Additionally, although exemplary embodiments of the IMU 7096 have been described above for providing indications regarding battery charge state and/or whether the batter is fully charged, in other exemplary embodiments, the IMU 7096 may provide other information to the user such as a charge rate, a date of last charge, a charge ratio and/or other similar information on the condition of the battery.

Figure 34:
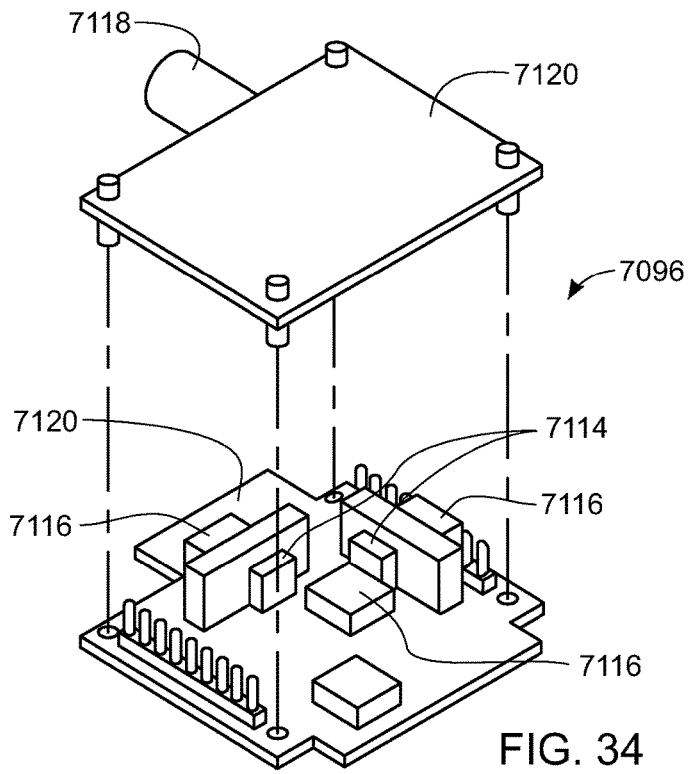
FIG. 34 is a partially exploded view of an inertial measurement unit according to an embodiment of the present invention.

Referring to FIG. 34, the IMU 7096 may include one or more accelerometers 7114 and/or one or more gyroscopes 7116, to measure orientation of the IMU 7096 relative to a gravitational direction G, shown in FIG. 32, including, but not limited to, sensing type, rate, and direction of the orientation change of the IMU 7096. The IMU 7096 has an output 7118 to facilitate connection of the IMU 7096 to the sensor CPU 7019, sensor module communicator 7020 and battery (not shown) through the electronics orifice 7110, shown in FIG. 33. The one or more accelerometers 7114 and the one or more gyroscopes 7116 may be electrically connected to the output 7118 by one or more circuit boards 7120. As discussed above, the sensor module communicator 7020 may include a radio or Bluetooth® transmitter for wirelessly transmitting signals to the device module 7017, shown in FIGS. 31A and 31B, or the sensor module communicator 7020 may be hardwired to the device module 7017, shown in FIGS. 31A and 31B.

Referring back to FIG. 32, the data collected from the at least one IMU 7096 may be used by the device module 7017, shown in FIGS. 31A and 31B, in an algorithm to translate orientation of the foot 7021 and/or changes in orientation to a commanded movement of the prosthetic device 7012, shown in FIGS. 31A and 31B. In some embodiments, IMU 7096 may include at least two accelerometers 7114 detecting acceleration about two axes and at least one gyroscope 7116 for detecting orientation changes about a third axis. Thus, the IMU 7096, in some embodiments, may detect orientation changes about at least three axes, thereby allowing the user to control the prosthetic device 7012, shown in FIGS. 31A and 31B, in at least three degrees of freedom.

The accelerometers 7114 of each of the IMUs 7096 may be arranged to detect pitch $\theta_{Pitch}$ about the X axis relative to the gravitational direction G and roll $\theta_{Roll}$ about the Y axis relative to the gravitational direction G. The gyroscope 7116, shown in FIG. 34, of each of the IMUs 7096 is, in some embodiments, arranged to detect yaw $\dot{\theta}_{Yaw}$ about the Z axis. Thus, by using two IMUs 7096, one IMU 7096 on each foot 7021, the user is able to control the prosthetic device 7012, shown in FIGS. 31A and 31B, in at least six degrees of freedom.

Each IMU 7096 is arranged with one accelerometer 7114 in the Y direction and the other accelerometer 7114 in the X direction. When the IMU 7096 is flat, i.e. the Z axis is coincident with the gravitational direction G, gravity, which is an acceleration of 1G in the gravitational direction G, only includes a component projected on the Z axis. As the IMU 7096 tilts, a component of gravity is projected onto the X axis and/or Y axis. This tilt is detectable by the accelerometer 7114 arranged on the axis upon which the component of gravity is projected. Since 1G is a known value, the arcsin of the value detected by each accelerometer 7114 of the IMU 7096 is a proportion of 1G and representative of the pitch $\theta_{Pitch}$ and/or roll $\theta_{Roll}$.

Figure 35:
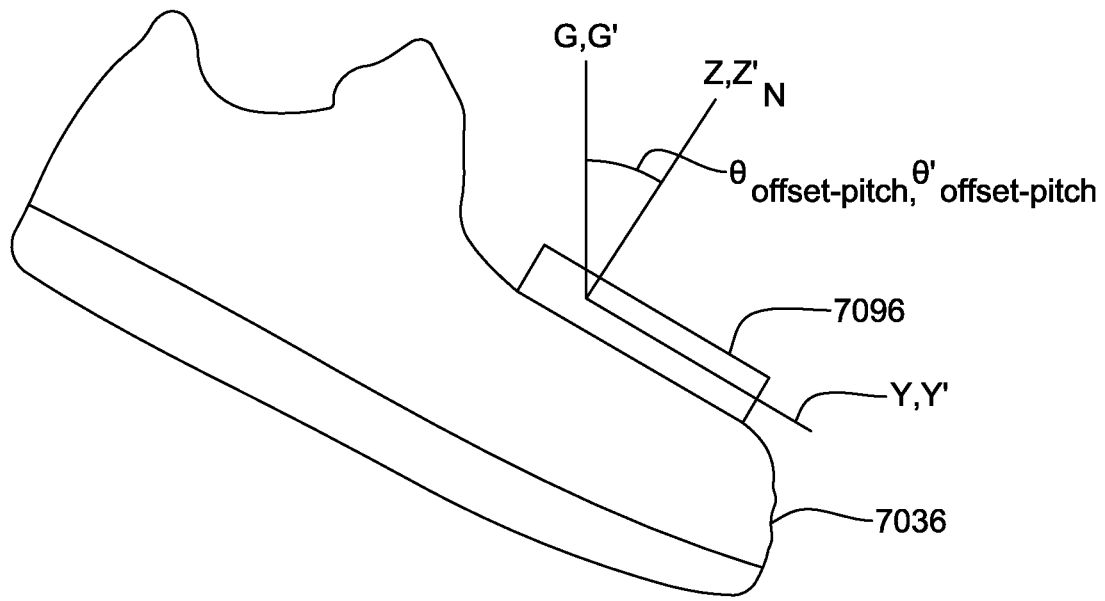
FIG. 35 is a side view of an inertial measurement unit of FIG. 32 tilted forward.
Figure 36:
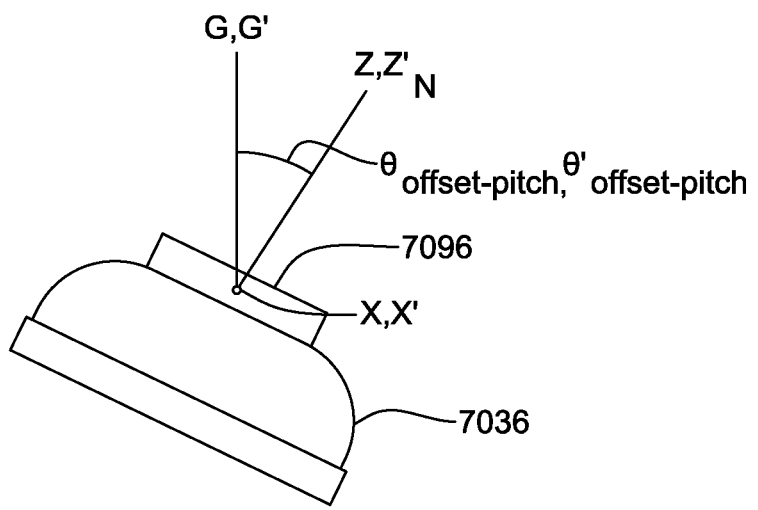
FIG. 36 is a front view of an inertial measurement unit of FIG. 32 tilted sideways.

Although shown in FIG. 32 with the Z axis being coincident with the gravitational direction G, as seen in FIGS. 35 and 36, the Z axis of each of the IMUs 7096 may be offset from the gravitational direction G; for example, if the IMU 7096 is not initially situated flatly on the users foot 7021, if the IMU 7096 shifts during use, or if the user is standing on an incline, decline or the like. Therefore, the sensor module 7015 of the present invention may zero the IMUs 7096, as will be discussed in greater detail below, by setting a pitch offset, $\theta_{Offset\_Pitch}$, and a roll offset, $\theta_{Offset\_Roll}$, when initialized or reinitialized during use.

Figure 37:
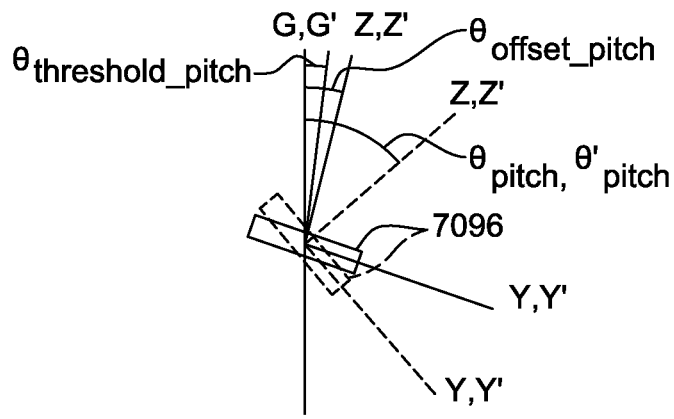
FIG. 37 is side view of the inertial measurement unit of FIG. 35.

Referring to FIG. 37, the pitch $\theta_{Pitch}$ detected by the IMU 7096 may be configured to command the prosthetic device 7012, shown in FIGS. 31A and 31B. For example, the device module 7017, shown in FIGS. 31A and 31B, may command the prosthetic device when:

$$|\theta_{Pitch} - \theta_{Offset\_Pitch}| \geq \theta_{Threshold\_Pitch}$$

where, $\theta_{Pitch}$ is the pitch detected by the IMU 7096 relative to the gravitational direction G;

$\theta_{Offset\_Pitch}$ is the preset value calibrating the IMU 7096 discussed above; and $\theta_{Threshold\_Pitch}$ is a present minimum pitch angle that must be exceeded to ensure that the detected pitch $\theta_{Pitch}$ is a desired command and not due to unintentional movement of the user's foot 7021, shown in FIG. 32.

In one embodiment, the command generated by the device module 7017, shown in FIGS. 31A and 31B, from the pitch $\theta_{Pitch}$ may be a switch that alternates between an "on state" and an "off state" each time $|\theta_{Pitch} - \theta_{Offset\_Pitch}| \geq \theta_{Threshold\_Pitch}$. In another embodiment, pitch $\theta_{Pitch}$ may command the controller to toggle through a list of operational control modes, which will be discussed in greater detail below. For example, each instance that $\theta_{Threshold\_Pitch}$ is exceeded, the controller may toggle forward through the list if $(\theta_{Pitch} - \theta_{Offset\_Pitch})$ is a positive value and may toggle backward, i.e. in reverse, through the list if $(\theta_{Pitch} - \theta_{Offset\_Pitch})$ is a negative value.

In one embodiment, the command generated by the device module 7017, shown in FIGS. 31A and 31B, may correspond to a movement, $M_{Pitch}$, of the prosthetic device 7012, shown in FIGS. 31A and 31B, if $|\theta_{Pitch} - \theta_{Offset\_Pitch}| \geq \theta_{Threshold\_Pitch}$. For example, when $|\theta_{Pitch} - \theta_{Offset\_Pitch}| \geq \theta_{Threshold\_Pitch}$ the device module 7017, shown in FIGS. 31A and 31B, may command movement at a preset velocity in a preset direction, e.g. the device module 7017 may command upward movement at the preset velocity if $(\theta_{Pitch} - \theta_{Offset\_Pitch})$ is a positive value and may command downward movement if $(\theta_{Pitch} - \theta_{Offset\_Pitch})$ is a negative value. In another embodiment, the movement may be commanded using the equation:

$$M_{Pitch} = k_1(\theta_{Pitch} - \theta_{Offset\_Pitch}) + k_2$$

where, $k_1$ and $k_2$ are gains that may be preset based on the type of movement desired. The movement $M_{Pitch}$ may be set to correspond to a variety of possible movements of the prosthetic device 7012, shown in FIGS. 31A and 31B. For example, $M_{Pitch}$ may be a distance of deflection in a direct direction or a speed of travel in a direction.

Figure 38:
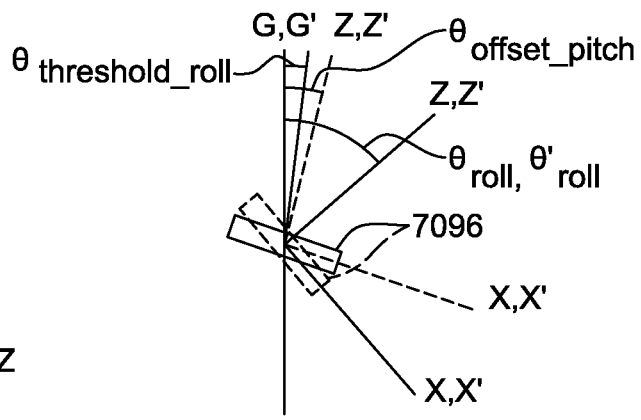
FIG. 38 is a front view of the inertial measurement unit of FIG. 36.

Referring to FIG. 38, the roll $\theta_{Roll}$ detected by the IMU 7096 may also be configured to command the prosthetic device 7012, shown in FIGS. 31A and 31B, in a manner similar to that discussed above for the pitch $\theta_{Pitch}$. For example, the device module 7017, shown in FIGS. 31A and 31B, may command the prosthetic device when:

$$|\theta_{Roll} - \theta_{Offset\_Roll}| \geq \theta_{Threshold\_Roll}$$

where, $\theta_{Roll}$ is the roll detected by the IMU 7096 relative to the gravitational direction G;

$\theta_{Offset\_Roll}$ is the preset value calibrating the IMU 7096 discussed above; and $\theta_{Threshold\_Roll}$ is a present minimum roll angle that must be exceeded to ensure that the detected roll $\theta_{Roll}$ is a desired command and not due to unintentional movement of the user's foot 7021, shown in FIG. 32.

In one embodiment, the command generated by the device module 7017, shown in FIGS. 31A and 31B, from the roll $\theta_{Roll}$ may be a switch that alternates between an "on state" and an "off state" each time $|\theta_{Roll} - \theta_{Offset\_Roll}| \geq \theta_{Threshold\_Roll}$. In another embodiment, roll $\theta_{Roll}$ may command the device module 7017, shown in FIGS. 31A and 31B, to toggle through a list of operational modes, which will be discussed in greater detail below. For example, each instance that $\theta_{Threshold\_Roll}$ is exceeded, the device module 7017, shown in FIGS. 31A and 31B, may toggle forward through the list if $(\theta_{Roll} - \theta_{Offset\_Roll})$ is a positive value and may toggle backward, i.e. in reverse, through the list if $(\theta_{Roll} - \theta_{Offset\_Roll})$ is a negative value.

In one embodiment, the command generated by the device module 7017, shown in FIGS. 31A and 31B, may correspond to a movement, $M_{Roll}$, of the prosthetic device 7012, shown in FIGS. 31A and 31B, if $|\theta_{Roll} - \theta_{Offset\_Roll}| \geq \theta_{Threshold\_Roll}$. For example, when $|\theta_{Roll} - \theta_{Offset\_Roll}| \geq \theta_{Threshold\_Roll}$ the device module 7017, shown in FIGS. 31A and 31B, may command movement at a preset velocity in a preset direction, e.g. the device module 7017 may command movement to the right at the preset velocity if $(\theta_{Roll} - \theta_{Offset\_Roll})$ is a positive value and may command movement to the left if $(\theta_{Roll} - \theta_{Offset\_Roll})$ is a negative value. In another embodiment, the movement may be commanded using the equation:

$$M_{Roll} = k_3(\theta_{Roll} - \theta_{Offset\_Roll}) + k_4$$

where, $k_3$ and $k_4$ are gains that may be preset based on the type of movement desired. The movement $M_{Roll}$ may be set to correspond to a variety of possible movements of the prosthetic device 7012, shown in FIGS. 31A and 31B. For example, $M_{Roll}$ may be a distance of deflection in a direct direction or a speed of travel in a direction.

Figure 39:
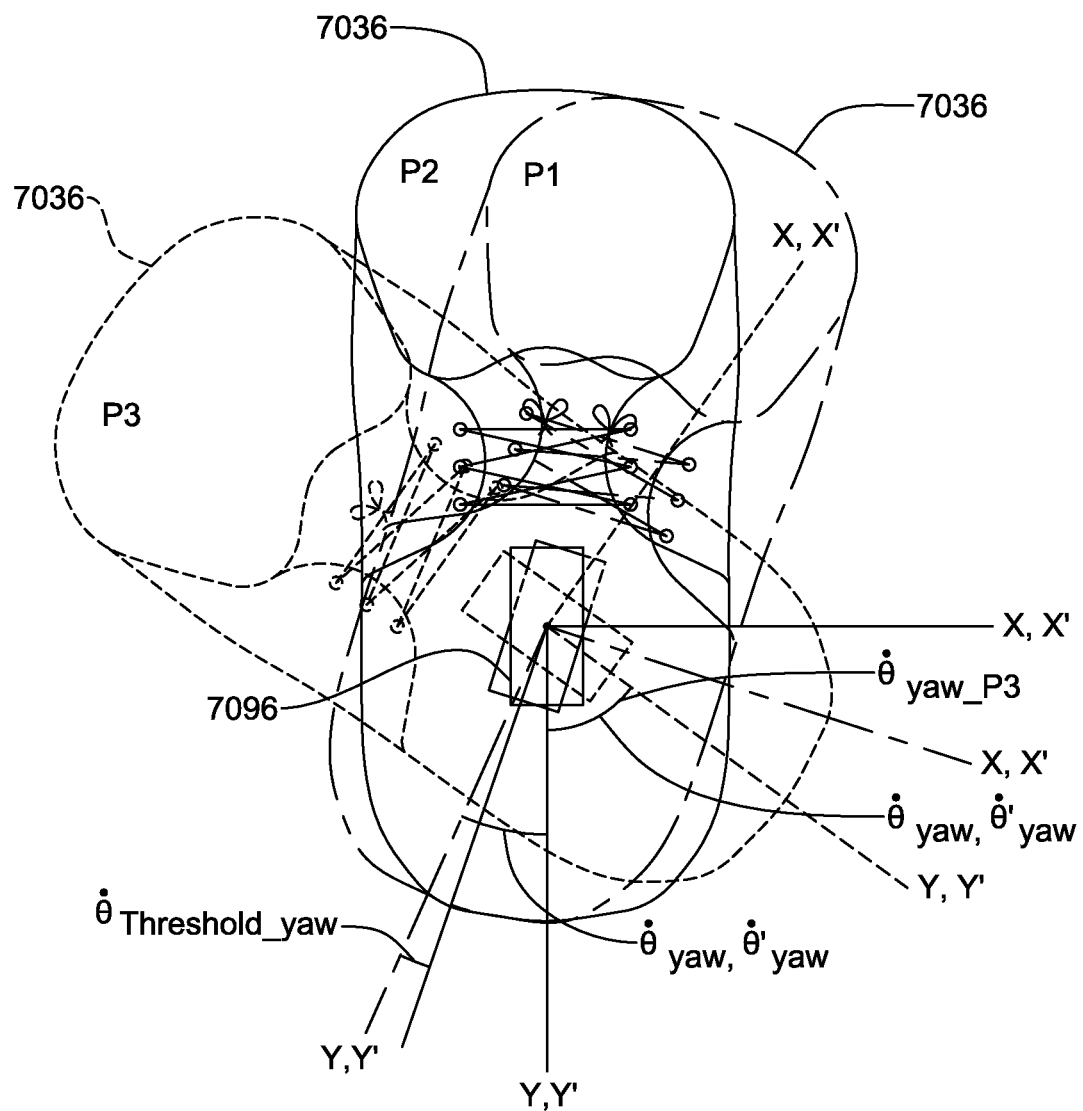
FIG. 39 is a top view of an inertial measurement unit of FIG. 32.

Referring to FIG. 39, each gyroscope 7116 is able to detect yaw $\dot{\theta}_{Yaw}$ as the rate of angular rotation relative to the Z axis. Thus, yaw $\dot{\theta}_{Yaw}$ about the Z axis is detectable by the IMU 7096 when the user's foot 7021 moves about the Z axis. Unlike the pitch $\theta_{Pitch}$ and roll $\theta_{Roll}$, which are each detected relative to a fixed reference, i.e. the gravitational direction G, the yaw $\dot{\theta}_{Yaw}$ is detected by the gyroscope 7116 with respect to the reference frame of the gyroscope 7116. Thus, the gyroscope 7116 effectively resets its frame of reference after each angular deflection of the IMU 7096. For example, if after moving from the first position $P_1$ to the second position $P_2$, the user then moves the IMU 7096 to a third position $P_3$, the yaw $\dot{\theta}_{Yaw}$ detected by the IMU 7096 as the IMU 7096 moves from the second position $P_2$ to the third position $P_3$ would be relative to the second position $P_2$. This yaw $\dot{\theta}_{Yaw}$ detected by the IMU 7096 may be configured to command the prosthetic device 7012, shown in FIGS. 31A and 31B.

For example, the device module 7017, shown in FIGS. 31A and 31B, may command the prosthetic device 7012 when:

$$|\dot{\theta}_{Yaw}| \geq \dot{\theta}_{Threshold\_Yaw}$$

where, $\dot{\theta}_{Yaw}$ is the yaw detected by the IMU 7096; and $\dot{\theta}_{Threshold\_Yaw}$ is a present minimum yaw angular rotation that must be exceeded to ensure that the detected yaw $\dot{\theta}_{Yaw}$ is a desired command and not due to unintentional movement of the user's foot 7021, shown in FIG. 32, or drifting of the gyroscope 7116.

Advantageously, since the yaw $\dot{\theta}_{Yaw}$ detected by the gyroscope 7116 about the Z axis is relative to the previous position of the IMU 7096, rather than a fixed reference frame like the gravitational direction G, shown in FIG. 32, a yaw offset is not necessary, as was the case with detection of the pitch and roll.

In one embodiment, the command generated by the device module 7017, shown in FIGS. 31A and 31B, from the yaw $\dot{\theta}_{Yaw}$ may be a switch that alternates between an "on state" and an "off state" each time $|\dot{\theta}_{Yaw}| \geq \dot{\theta}_{Threshold\_Yaw}$. In another embodiment, yaw $\dot{\theta}_{Yaw}$ may command the device module 7017, shown in FIGS. 31A and 31B, to toggle through a list of operational modes, which will be discussed in greater detail below. For example, each instance that $\dot{\theta}_{Threshold\_Yaw}$ is exceeded, the device module 7017, shown in FIGS. 31A and 31B, may toggle forward through the list if $\dot{\theta}_{Yaw}$ is a positive value and may toggle backward, i.e. in reverse, through the list if $\dot{\theta}_{Yaw}$ is a negative value.

In one embodiment, the command generated by the device module 7017, shown in FIGS. 31A and 31B, may correspond to a movement, $M_{Yaw}$, of the prosthetic device 7012, shown in FIGS. 31A and 31B, if $|\dot{\theta}_{Yaw}| \geq \dot{\theta}_{Threshold\_Yaw}$. For example, when $|\dot{\theta}_{Yaw}| \geq \dot{\theta}_{Threshold\_Yaw}$ the device module 7017, shown in FIGS. 31A and 31B, may command movement $M_{Yaw}$ at a preset velocity in a preset direction, e.g. the device module 7017 may command movement to the right at the preset velocity if $\dot{\theta}_{Yaw}$ is a positive value and may command movement to the left if $\dot{\theta}_{Yaw}$ is a negative value. In this exemplary embodiment for commanding right and left movement, it may also be desirable to halt right and left movement using the detected yaw $\dot{\theta}_{Yaw}$. For example, if the device module 7017 has commanded movement $M_{Yaw}$ to the right, based on a positive $\dot{\theta}_{Yaw}$ a subsequently detected negative $\dot{\theta}_{Yaw}$ that satisfies the relationship $|\dot{\theta}_{Yaw}| \geq \dot{\theta}_{Threshold\_Yaw}$ may generate a command to stop moving to the right, rather than a command to move to the left. From the stopped position, another negative $\dot{\theta}_{Yaw}$ that satisfies the relationship $|\dot{\theta}_{Yaw}| \geq \dot{\theta}_{Threshold\_Yaw}$ would then command leftward movement or, alternatively, a positive $\dot{\theta}_{Yaw}$ that satisfies the relationship $|\dot{\theta}_{Yaw}| \geq \dot{\theta}_{Threshold\_Yaw}$ would then command rightward movement. Similarly, if the device module 7017 has commanded movement $M_{Yaw}$ to the left, based on a negative $\dot{\theta}_{Yaw}$, a subsequently detected positive $\dot{\theta}_{Yaw}$ that satisfies the relationship $|\dot{\theta}_{Yaw}| \geq \dot{\theta}_{Threshold\_Yaw}$ may generate a command to stop moving to the left, rather than a command to move to the right. From the stopped position, a negative $\dot{\theta}_{Yaw}$ that satisfies the relationship $|\dot{\theta}_{Yaw}| \geq \dot{\theta}_{Threshold\_Yaw}$ would then command leftward movement or, alternatively, a positive $\dot{\theta}_{Yaw}$ that satisfies the relationship $|\dot{\theta}_{Yaw}| \geq \dot{\theta}_{Threshold\_Yaw}$ would then command rightward movement.

For exemplary purposes, the pitch $\theta_{Pitch}$, roll $\theta_{Roll}$ and yaw $\dot{\theta}_{Yaw}$ have been described as commanding specific movements in connection with FIGS. 35-39. However, it should be understood that the pitch $\theta_{Pitch}$, roll $\theta_{Roll}$ and yaw $\dot{\theta}_{Yaw}$ may be programmed within the device module 7017, shown in FIGS. 31A and 31B, to command a variety of different movements, and in some embodiments, in response to the user's preferences and customization, as will be discussed in greater detail below.

It should be understood that although the use of at least one IMU 7096 for control of a prosthetic device 7012, shown in FIGS. 31A and 31B, is described herein, the at least one IMU 7096 may be used in conjunction with any one or more various devices and/sensors 7018 to control the prosthetic device 7012. Thus, in some embodiments, the IMU 7096 may be used in conjunction with the sensors 7018, top sensors 60 and sensor grid 6084 discussed above, as well as with an EMG system and with a pull switch or other inputs. For example, in various embodiments of present invention, one or more prosthetic shoulder movements may be controlled by the shoulder sensor 5028, shown in FIG. 22, while side to side movements of the prosthetic device 7012 may be controlled by sensors 7018, sensor grids 6084 or IMUs 7096.

Additionally, although an exemplary embodiment of the IMU 7096 is described herein which may be used in the exemplary embodiment of the system, apparatus and method for control of a prosthetic device 7012, shown in FIGS. 31A and 31B, in other embodiments, any device capable of determining orientation may be used for the IMU 7096, as should be understood by those skilled in the art. For instance, another type of sensor 18 may be used in the IMU 7096, such as a 3-axis accelerometer, a 3-axis magnetometer and tilt bulb(s).

In some embodiments, it may be beneficial to include three accelerometers 7114 or a three-axis accelerometer, in the IMU 7096 along with at least one gyroscope 7116 for detecting orientation changes about at least three axes and for enabling walk detection. In an embodiment with IMU 7096 having three accelerometers 7114, the IMU 7096 generates output relating to pitch $\theta_{Pitch}$, roll $\theta_{Roll}$ and yaw $\dot{\theta}_{Yaw}$ in substantially the same manner discussed above in connection with the IMU 7096 having two accelerometers 7114. However, with the third accelerometer 7114, the IMU 7096 may provide the control apparatus 7010, shown in FIGS. 31A and 31B, with walk detection capability.

Figure 40:
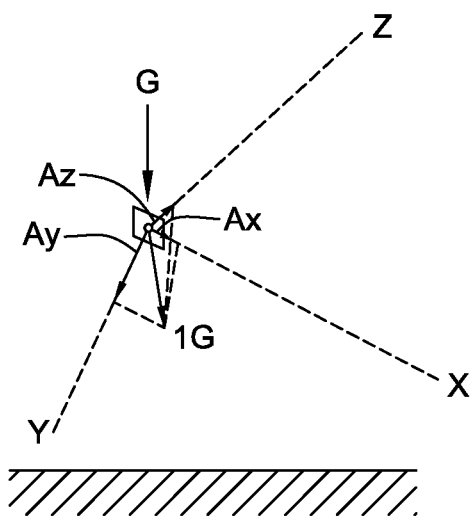
FIG. 40 is a side perspective view of an inertial measurement unit according to an embodiment of the present invention.

Referring back to FIGS. 31A and 31B, when using the IMU 7096 for control of the prosthetic device 7012, walking may be problematic, since walking movement of the user's foot 7021, shown in FIG. 32, will cause the IMU 7096 to sense orientation changes, which the device module 7017 will use to command movement of the prosthetic device 7012. However, walking may be detected by providing an IMU 7096 having a third accelerometer 7114. Referring to FIG. 32, each of the accelerometers 7114 may be arranged to measure the acceleration in one of the X, Y or Z directions. Thus, when the user is substantially stationary, the vector sum of the accelerations detected by each of the three accelerometers 7114 should be substantially equal to 1G. When the Z axis is coincident with the direction of gravity G, the accelerometer 7114 detecting acceleration in the Z direction will detect the entire 1G acceleration due to gravity, since the accelerations in the X and Y directions will be substantially equal to zero. Now, referring to FIG. 40, when the user is stationary, but the direction of gravity G is not coincident with the Z axis, i.e. the user has moved their foot 7021 to command a pitch $\theta_{Pitch}$ and/or roll $\theta_{Roll}$, the vector sum of the accelerations Ax, Ay and Az in the X, Y and Z directions, respectively, will still equal 1G.

Figure 41:
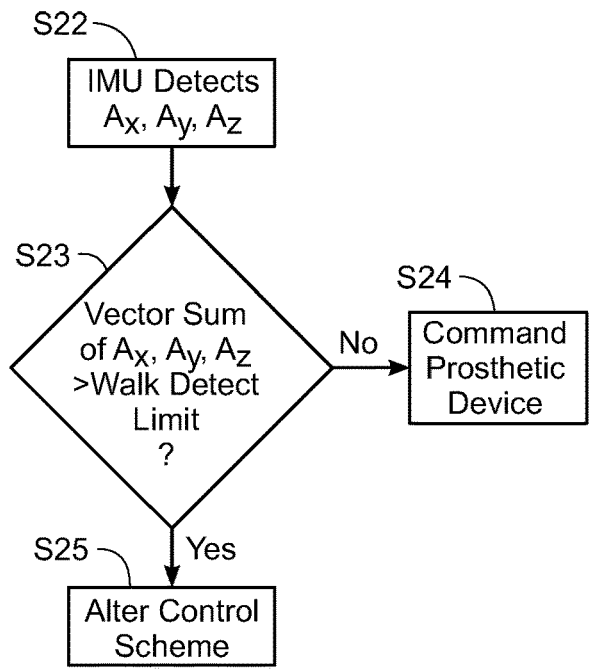
FIG. 41 is a process diagram of an embodiment for walk detection according to the present invention.

If the user begins to walk, the vector sum of the accelerations Ax Ay and Az detected by each of the three accelerometers 7114 will be substantially greater than 1G, since the act of walking will cause additional acceleration, other than gravity, to be detected by the IMU 7096. Therefore, referring to FIG. 41, once the IMU 7096 detects the accelerations Ax, Ay and Az in S22, the vector sum of the accelerations may be compared to a walk detect limit in S23. In some embodiments, the walk detect limit may be set at approximately 1.2 G. If the vector sum of the accelerations is lower than the walk detect limit, in S24, the device module 7017, shown in FIGS. 31A and 31B, will command the prosthetic device 7012, shown in FIGS. 31A and 31B, in accordance with the pitch $\theta_{Pitch}$, roll $\theta_{Roll}$ and/or yaw $\dot{\theta}_{Yaw}$ detected by the IMU 7096. However, if the walk detect limit is exceeded by the vector sum of the accelerations, the device module 7017, shown in FIGS. 31A and 31B, will assume the user is walking and may alter the control scheme for the prosthetic device 7012 in S25.

For example, in one embodiment of an altered control scheme when walking is detected, the device module, shown in FIGS. 31A and 31B, filters out high accelerations from the pitch $\theta_{Pitch}$, roll $\theta_{Roll}$ and/or yaw $\dot\theta_{Yaw}$ signals generated by the IMU 7096, shown in FIG. 32, when the vector sum of the accelerations Ax, Ay and Az is greater than the walk detect limit. Thus, when the user begins to walk, measurements having a value larger than the walk detect limit will not command movement of the prosthetic device 7012, shown in FIGS. 31A and 31B. This walk detection embodiment is beneficial, as discussed above, because once the user is walking, the accelerations detected by the IMU(s) 7096 are large enough that the resulting signal may not be correctly indicative of the user's intent. In some embodiments, this embodiment of walk detection may be implemented where one or more IMUs 7096 is worn on another area of the user, including, but not limited to, the residuum.

In another embodiment for a walk detection control scheme, when the control apparatus 7010, shown in FIGS. 31A and 31B, senses a user is walking, the device module 7017, shown in FIGS. 31A and 31B, may stop using the signals generated by the IMU 7096, shown in FIG. 32, entirely, and instead switch to another sensor or signal input, e.g., EMG, to determine user input intent. Additionally, in some embodiments, where the control apparatus 7010, shown in FIGS. 31A and 31B, detects that the user is walking, the device module 7017, shown in FIGS. 31A and 31B, may enter a standby mode, in which no commands are sent to the prosthetic device 7012, shown in FIGS. 31A and 31B, as will be discussed in greater detail below. Entering standby mode both saves power and, also, prevents the prosthetic device 7012, shown in FIGS. 31A and 31B, from executing potentially erratic and unintended movement.

In some embodiments, the walk detect limit may need to be exceeded for a predetermined duration e.g., at least 6 seconds, before the control apparatus 7010, shown in FIGS. 31A and 31B, implements a different command after a predetermined amount of time the user is walking. In this embodiment, the device module 7017, shown in FIGS. 31A and 31B, may then send a command signal to the prosthetic device 7012, shown in FIGS. 31A and 31B, after the predetermined period has elapsed to place most of the controlled electronics (i.e., the electronics in the prosthetic device 7012) into a sleep mode. When in sleep mode, if the control apparatus 7010, shown in FIGS. 31A and 31B, determines that the user is no longer walking, which may be detected from the orientation signals generated by the IMU 7096 indicating that the vector sum of the accelerations Ax, Ay and Az is below the walk detect limit for the predetermined period, the device module 7017, shown in FIGS. 31A and 31B, may then turn the controlled electronics on again to allow normal operation of the prosthetic device 7012, shown in FIGS. 31A and 31B.

In some embodiments, after the device module 7017 determines that the user is no longer walking, the control system may enter standby mode where it can be determined if the user has repositioned the IMU 7096 and, if so, the IMU may be zeroed. Additionally, in some embodiments, when walk detection mode is entered, the device module 7017 may stay in its current mode of operation but ignore body input signals from the IMU 7096 for a predefined walking time. Then, if the predefined walking time is exceeded and the device module 7017 still detects that the user is walking, the device module 7017 may enter standby mode to conserve power.

In another embodiment of a control scheme for when user walking has been detected, the device module 7017, shown in FIGS. 31A and 31B, may ignore only the yaw signal $\dot\theta_{Yaw}$ when the walk detect limit is exceeded by the vector sum of the accelerations Ax, Ay and Az. Then, when the control apparatus 7010, shown in FIGS. 31A and 31B, determines the user has stopped walking, the device module 7017, shown in FIGS. 31A and 31B, may begin using the yaw signal $\dot\theta_{Yaw}$ again. In some embodiments, the device module 7017, shown in FIGS. 31A and 31B, re-zeros the yaw measurement when the large accelerations cease (i.e., when the accelerations are below the walk detect limit).

In some embodiments, the control system of the present invention may include a power free swing mode that may be activated automatically when the device module 7017, shown in FIGS. 31A and 31B, determines that the user is walking. In power free swing mode, the device module 7017, shown in FIGS. 31A and 31B, may allow the joints of the prosthetic device 7012, shown in FIGS. 31A and 31B, to freely move, so that the prosthetic device 7012 may swing as a result of the user's walking movement. Power free swing mode provides the user with a more natural look while walking without significantly increasing power consumption to do so.

In another embodiment, the control system may include a power swing mode, which also controls the prosthetic device 7012, shown in FIGS. 31A and 31B, to swing as the user is walking. In various embodiments, the user may pre-select or pre-program into the device module 7017, shown in FIGS. 31A and 31B, a default swing speed and then may increase or decrease the speed during use. The user may select this mode and/or vary the speed by any of the various sensors 7018 and IMUs 7096 described herein for user input. In some embodiments, the control apparatus 7010, shown in FIGS. 31A and 31B, in the power swing mode may additionally determine the stride length and rhythm of the user and regulate the powered swing in response, to match the user's cadence.

Referring back to FIGS. 31A and 31B, as discussed above, the control apparatus 7010 may control the prosthetic device 7012 in a variety of control modes to achieve different functionality from the prosthetic device 7012. The use may enter and exit the different control modes with signals from the various sensors 7018 and IMUs 7096 discussed above. Additionally, some control modes may be entered automatically if a preset condition is achieved, for example, entering power free swing mode or standby mode if the walk detect limit is exceeded, as discussed above.

One control mode of the present invention may be a calibration mode that the user may enter once the user places the IMU(s) 7096, shown in FIG. 32, on their foot or feet 7021, shown in FIG. 32. This calibration mode may negate any misalignments of the IMU 7096 on the user's foot 7021, for example, by setting the pitch and yaw offset angles discussed above. In some embodiments, the user may place the IMU(s) 7096 on their foot or feet 7021 and then power the IMU(s) 7096 "on" to automatically enter the calibration mode. Once in the calibration mode, the user may perform one or more calibration movements with their foot or feet 7021, i.e., "toe up", "heel up", "tilt side to side", etc., to establish a baseline for the range of motion of the user's foot or feet 7021, which may be used, for example, to set motion control gains such as gains $k_1$, $k_2$, $k_3$ and $k_4$ discussed above. These calibration movements and their order of performance are for exemplary purposes only. In other embodiments, different calibration movements and/or a different order of performance of calibration movements may be used, as should be understood by those skilled in the art. In various embodiments, the user may be required to complete a "range of motion" to establish a baseline and for the system to establish the X, Y and Z axes. Other embodiments of the present invention may implement calibration modes as well. For instance, in the embodiment having the sensor grid 6084, shown in FIG. 8A, the calibration mode may detect a current pressure profile of the user's foot so that changes in the pressure profile can then be detected to control the prosthetic device 7012.

Figure 42:
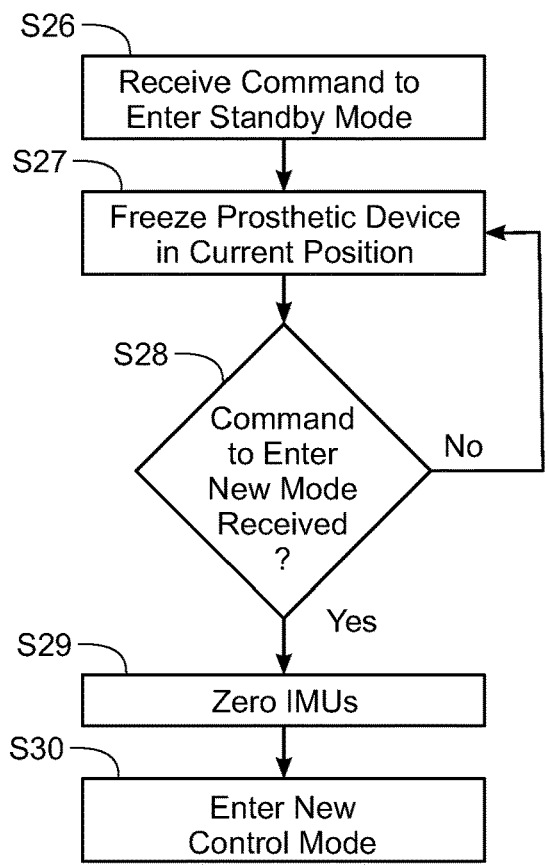
FIG. 42 is a process diagram of an embodiment for mode changing according to the present invention.

Referring to FIG. 42, as discussed above, one control mode of the present invention may be standby mode. The device module 7017, shown in FIGS. 31A and 31B, initiates standby mode upon receipt of a particular body input signal from the sensor module 7015, shown in FIGS. 31A and 31B, in S26. For instance, the body input signal may be generated by engaging a particular sensor 7018, by a specific orientation of one or more IMUs 7096 or the like. Additionally, as discussed above, the signal may be generated automatically, for example, if the control apparatus 7010, shown in FIGS. 31A and 31B, detects that the user is walking. Upon entering standby mode, the prosthetic device 7012, shown in FIGS. 31A and 31B, becomes frozen or locked in its current position in S27. In some embodiments, this may include turning off actuators and turning brakes and/or clutches on within the prosthetic device 7012. In some embodiments, while in standby mode, the device module 7017, shown in FIGS. 31A and 31B, does not send commands to the prosthetic device 7012, and therefore, does not command unintended movement of the prosthetic device 7012. Standby mode is advantageous since it may allow the user to maintain the prosthetic device 7012 in a desired position without significantly draining battery power.

The device module 7017, shown in FIGS. 31A and 31B, is maintained in standby mode until the device module 7017 receives an input signal in S28 indicating that a new control mode is to be entered. In some embodiments of the present invention, when standby mode is exited and a new control mode is entered, for example, bulk mode, finesse mode or the like, the device module 7017 will send a zero command to the sensor module 7015, which the sensor module 7015 may use to redefine its zero position or orientation to be the current position or orientation. For example, the device module 7017, shown in FIGS. 31A and 31B, may send a zero command to the IMU 7096 of the sensor module 7015 by setting a pitch offset, $\theta_{Offset\_Pitch}$, and a roll offset, $\theta_{Offset\_Roll}$. Thus, any orientation changes of the foot/feet 7021, shown in FIG. 32, occurring between the time the device module 7017, shown in FIGS. 31A and 31B, entered standby mode in S26 and the time that the device module 7017, shown in FIGS. 31A and 31B, exited standby mode in S28 are compensated for by the device module 7017. Once the control system has been zeroed in S29, the device module 7017, shown in FIGS. 31A and 31B, enters the new control mode in S30 and begins continuously receiving data from the IMU(s) 7096 of the sensor module 7015, shown in FIGS. 31A and 31B, for controlling the prosthetic device 7012, shown in FIGS. 31A and 31B, in accordance with the new control mode. When in the new control mode, the prosthetic device 7012 will not move while the user's foot 7021 is in the zero position since the signals generated by the IMU 7096 for the zero position will be interpreted as zero by the device module 7017. When the user's foot 7021 leaves the zero position, the device module 7017 uses the data signals from the IMU 7096 to command movement of the prosthetic device 7012, shown in FIGS. 31A and 31B, based on the selected control mode.

The active zeroing process may be used in other embodiments and thus is not limited to use with the IMU. Further, the zeroing process may be beneficial for many reasons, including, but not limited to, where the user moves from flat ground to a sloped ground, the controls may interpret this as a command. Thus, active zeroing eliminates this issue which may otherwise give rise to unintended commands.

Figure 43:
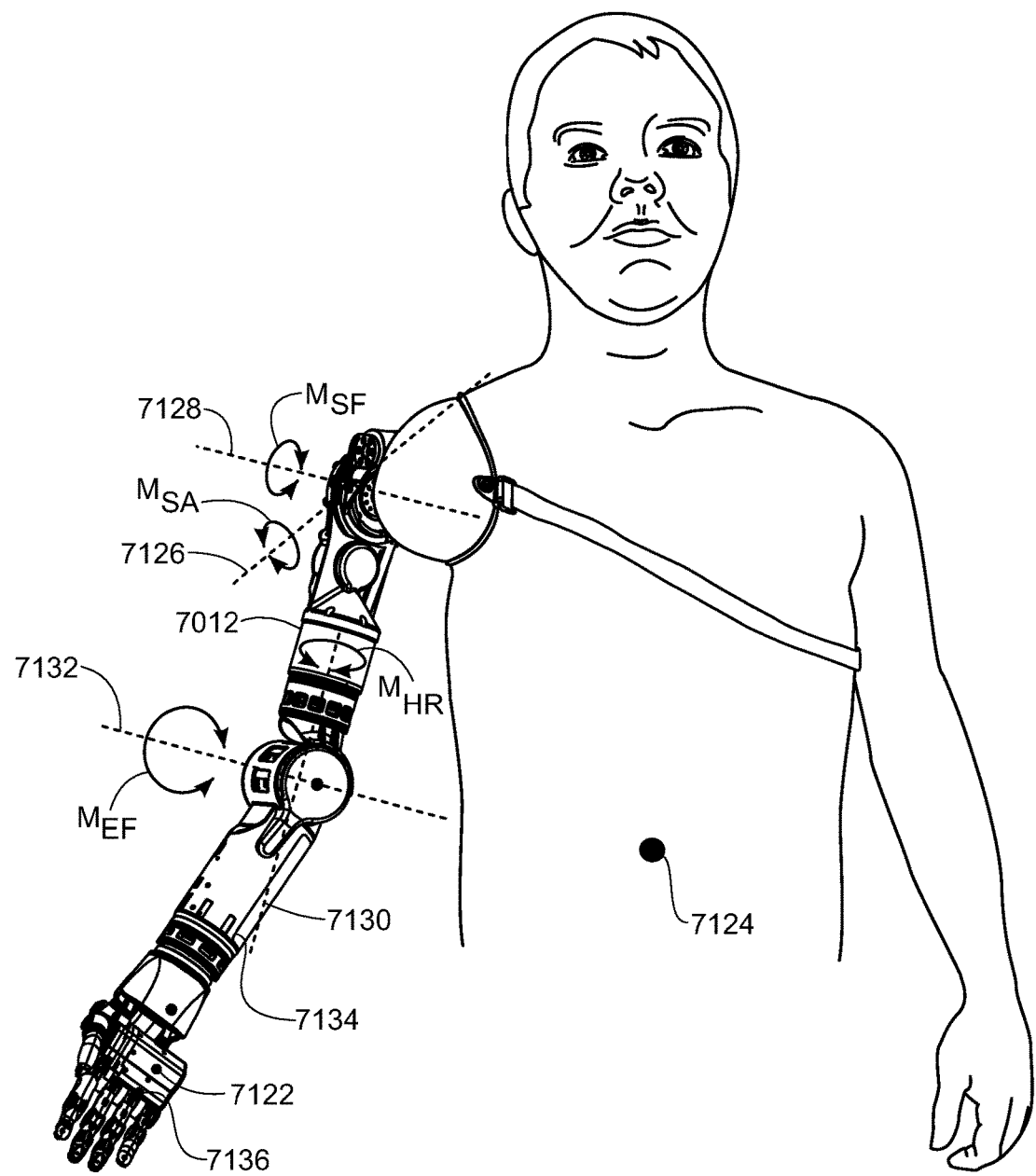
FIG. 43 is a side perspective view of an embodiment of bulk control according to the present invention.

Referring to FIG. 43, bulk mode includes movement of the prosthetic device 7012 into the general vicinity desired by the user. When in bulk mode, the signals from sensors 7018 and/or IMUs 7096 are used by the device module 7017, shown in FIGS. 31A and 31B, to move a prosthetic end point 7122 to a desired location 7124, i.e. a specific point in a three-dimensional space (x, y, and z components). For instance, in bulk mode, the signals from the IMUs 7096 and/or sensors 7014 may be used by the device module 7017, shown in FIGS. 31A and 31B, to command shoulder abduction, $M_{SA}$, about an abduction axis 7126, shoulder flexion, $M_{SF}$, about a shoulder flexion axis 7128, humeral rotation, $M_{HR}$, about a humeral rotation axis 7130 and elbow flexion, $M_{EF}$, about an elbow flexion axis 7132. In this way, the user is able to move the prosthetic end point 7122 to the desired location 7124, without actuating a prosthetic wrist 7134 and hand 7136. Then, once the prosthetic end point 7122 has reached the desired location 7124, the user may engage finesse mode to control the wrist 7134 and hand 7136, as will be discussed in greater detail below.

In one embodiment, the pitch $\theta_{Pitch}$, roll $\theta_{Roll}$ and yaw $\theta_{Yaw}$ detected by each IMU 7096, shown in FIG. 32, may correspond to movement of a specific joint of the prosthetic device 7012. For example, $M_{Pitch}$ and $M_{Roll}$, discussed above, may correspond to $M_{SF}$ and $M_{SA}$, respectively. Similarly, $M_{Pitch}'$ and $M_{Roll}'$ may correspond to $M_{EF}$ and $M_{HR}$, respectively. Thus, the user may move the prosthetic end point 7122 to the desired location 7124 by pitching and rolling each foot 7021, shown in FIG. 32, to move the appropriate prosthetic joints until the desired location 7124 is reached. Although described as corresponding to specific joint movements for exemplary purposes, it should be understood that $M_{Pitch}$, $M_{Roll}$, $M_{Yaw}$, $M_{Pitch}'$, $M_{Roll}'$ and $M_{Yaw}'$ may each be programmed in the device module 7017, shown in FIGS. 31A and 31B, to correspond to any of the joint movements, depending upon user preference. In the exemplary embodiment discussed above, $M_{Yaw}$, $M_{Yaw}'$ and/or other sensors 7018, shown in FIGS. 31A and 31B, may be programmed to perform other prosthetic functions such as mode switching or, alternatively, may not be programmed to perform any function while the control system is in bulk mode.

Figure 44A:
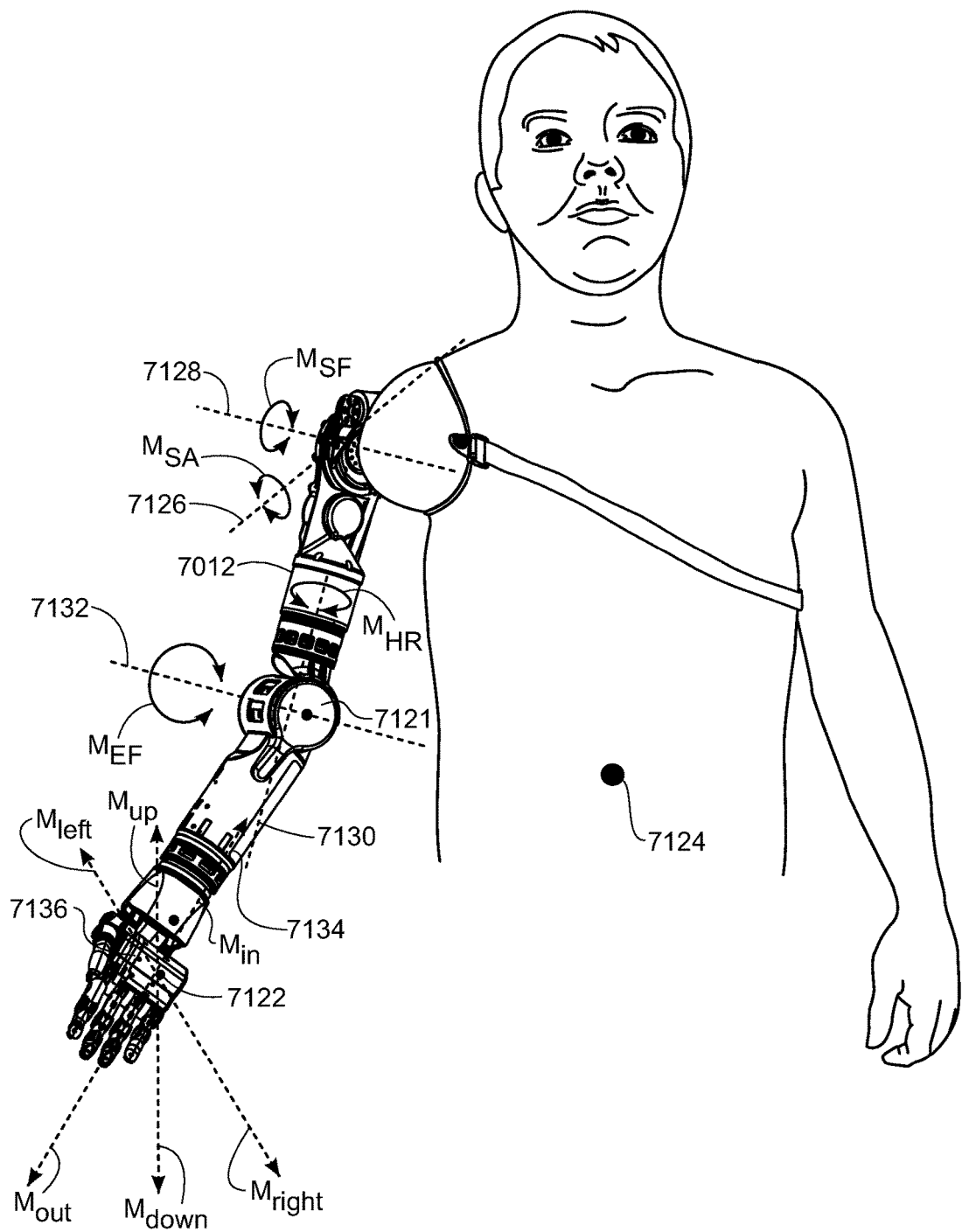
FIG. 44A is a side perspective view of another embodiment of bulk control according to the present invention.

Referring to FIG. 44A, in another embodiment for end point control in bulk mode, the pitch $\theta_{Pitch}$, roll $\theta_{Yaw}$ and yaw $\theta_{Yaw}$ signals generated by the IMUs 7096 may correspond directly to movement of the prosthetic end point 7122. For example, $M_{Pitch}$ may be programmed in the device module 7017, shown in FIGS. 31A and 31B, to command end point movement $M_{Up}$ and $M_{Down}$, $M_{Roll}$ may be programmed in the device module 7017, shown in FIGS. 31A and 31B, to command end point movement $M_{Right}$ and $M_{Left}$, and $M_{Pitch}'$ may be programmed in the device module 7017, shown in FIGS. 31A and 31B, to command $M_{In}$ and $M_{Out}$. Although described as corresponding to specific directional movements of the prosthetic end point 7122 for exemplary purposes, it should be understood that $M_{Pitch}$, $M_{Roll}$, $M_{Yaw}$, $M_{Pitch}'$, $M_{Roll}'$ and $M_{Yaw}'$ may each be programmed within the device module 7017, shown in FIGS. 31A and 31B, to correspond to any of the directional movements, depending upon user preference.

In this embodiment, the device module 7017, shown in FIGS. 31A and 31B, commands shoulder abduction $M_{SA}$ about the abduction axis 7126, shoulder flexion $M_{SF}$ about the shoulder flexion axis 7128, humeral rotation $M_{HR}$ about the humeral rotation axis 7130 and elbow flexion $M_{EF}$ about the elbow flexion axis 7132 in accordance with a movement function to achieve the commended movement of the prosthetic end point 7122, e.g. $M_{Up}$ or $M_{Down}$. This embodiment for control of the prosthetic end point 7122 may, in some embodiments, be preferable, since the user must only be concerned with directional movement of the end point 7122, rather than movement of individual joints to achieve the desired end point movement.

In some embodiments, end point control in bulk mode may include movement of the prosthetic device 7012 in four degrees of freedom to move the prosthetic end point 7122 to the desired location 7124, i.e. a specific point in a three-dimensional space (x, y, and z components). For example, the four degrees of freedom may include movement of the prosthetic end point 7122 in the three Cartesian directions in space having an origin set at the user's shoulder as well as rotation of an angle of rotation, phi, about an end point vector extending from the origin of the Cartesian system to the prosthetic end point 7122. The angle of rotation, phi, may be controlled by the user through the pitch $\theta_{Pitch}$, roll $\theta_{Yaw}$ or yaw $\dot{\theta}_{Yaw}$ signals generated by the IMUs 7096, shown in FIG. 32, in the same manner discussed above, thereby allowing the user to command the prosthetic elbow 7121 in or away from the body. However, the angle of rotation, phi, is also preferably compliant when the prosthetic end point 7122 is moved in the three Cartesian directions, as will be discussed in greater detail below.

Figure 44B:
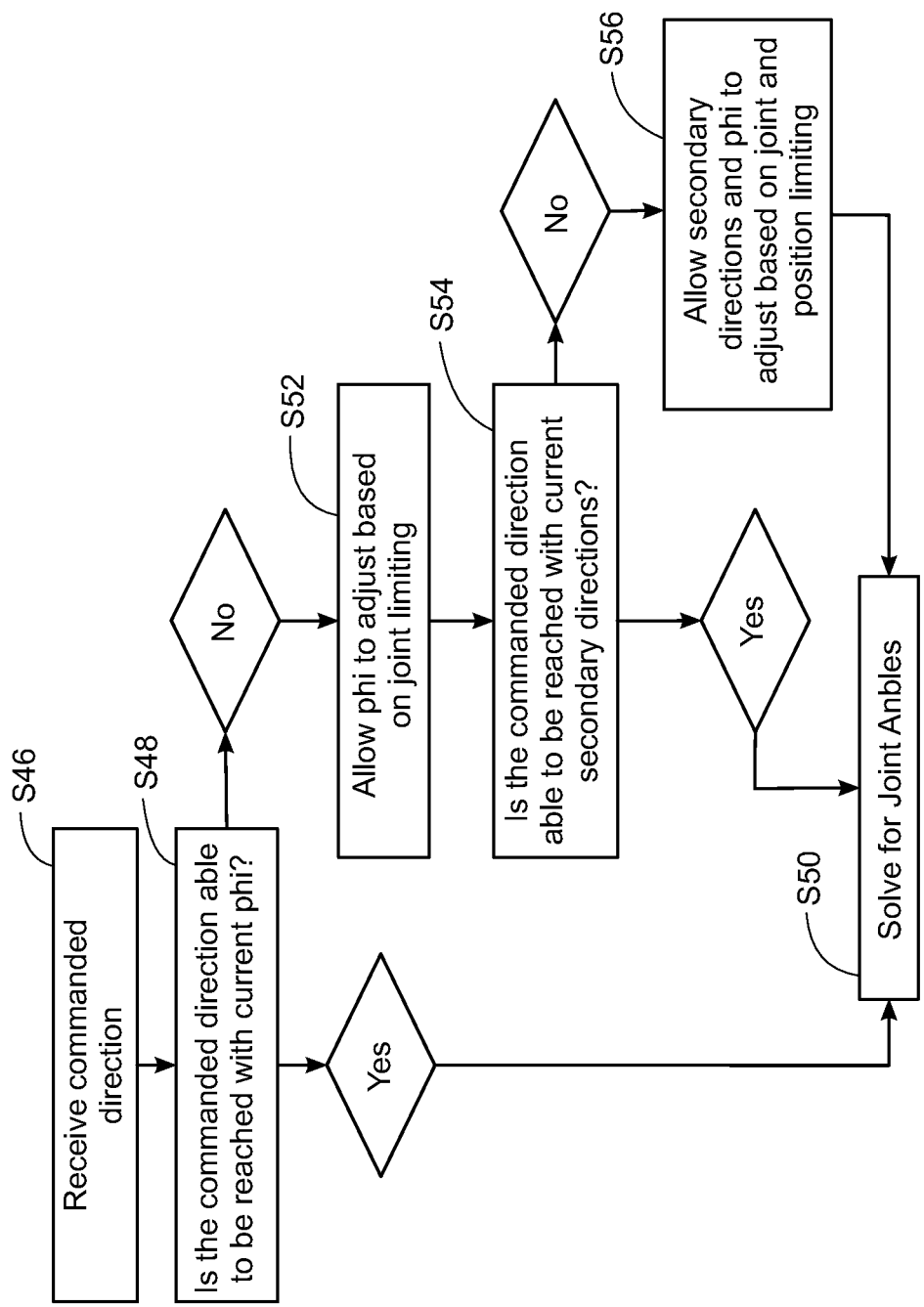
FIG. 44B is a process diagram of an embodiment of bulk control according to the present invention.

Referring to FIG. 44B, in end point control with four degrees of freedom of movement of the prosthetic device 7012, shown in FIG. 44A, a commanded direction of movement of the prosthetic end point 7122, shown in FIG. 44A, is received by the device module 7017, shown in FIGS. 31A and 31B, in S46. For example, as discussed above, the pitch $\theta_{Pitch}$, roll $\theta_{Yaw}$ and yaw $\dot{\theta}_{Yaw}$ signals generated by the IMUs 7096, shown in FIG. 32, may correspond to movement of the prosthetic end point 7122, shown in FIG. 44A. The device module 7017, shown in FIGS. 31A and 31B, then determines whether the commanded direction is able to be reached with the current angle of rotation, phi, in S48. The angle of rotation, phi, may have been preset by the user, as discussed above, or may simply be the previous angle of rotation. The determination also factors in lengths between the prosthetic joints of the prosthetic device 7012, shown in FIG. 44A, as well as any joint angle limits about the abduction axis 7126, the shoulder flexion axis 7128, the humeral rotation axis 7130 and the elbow flexion axis 7132. If it is determined that the direction may be reached with the current phi at S48, the joint angles necessary to achieve the desired direction may be solved for by the device module 7017, shown in FIGS. 31A and 31B, in S50 and the device module 7017, shown in FIGS. 31A and 31B, may command movement. For example, the device module 7017, shown in FIGS. 31A and 31B, may command shoulder abduction $M_{SA}$ about the abduction axis 7126, shoulder flexion $M_{SF}$ about the shoulder flexion axis 7128, humeral rotation $M_{HR}$ about the humeral rotation axis 7130 and elbow flexion $M_{EF}$ about the elbow flexion axis 7132 to achieve the desired direction of movement of the prosthetic end point 7122, e.g. $M_{UP}$ or $M_{Down}$. Alternatively, if it is determined that the direction cannot be reached with the current angle of rotation, phi, at S48, the device module 7017, shown in FIGS. 31A and 31B, adjusts the angle of rotation, phi, based on joint limiting using predefined joint angle limits about the abduction axis 7126, the shoulder flexion axis 7128, the humeral rotation axis 7130 and the elbow flexion axis 7132 at S52. This adjustment of the angle of rotation, phi, effectively changes the location of the elbow 7121, which changes the relation of the abduction axis 7126, the shoulder flexion axis 7128, the humeral rotation axis 7130 and the elbow flexion axis 7132 with the prosthetic end point 7122, thereby defining new secondary directions of movement. The device module 7017, shown in FIGS. 31A and 31B, then determines whether the commanded direction is able to be reached with the new angle of rotation, phi, and the secondary directions in S54. If it is determined that the commanded direction may be reached at S54, the joint angles necessary to achieve the desired direction may be solved for by the device module 7017, shown in FIGS. 31A and 31B, in S50, as discussed above, and the device module 7017, shown in FIGS. 31A and 31B, may command movement. Alternatively, if it is determined that the commanded direction cannot be reached at S54, in S56, the secondary directions and the angle of rotation, phi, are adjusted by the device module 7017, shown in FIGS. 31A and 31B, based on joint limiting, as discussed above, as well as based on position limiting, which is discussed in greater detail below. The device module 7017, shown in FIGS. 31A and 31B, then solves for the joint angles based on the desired direction and position limiting in S50 and commands movement.

Thus, the angle of rotation, phi, may advantageously be defined by the user to command the elbow 7121 in or away from the body, which provides the user with finer control for a variety of activities, such as picking up or placing objects, eating, moving objects from one level to another or the like. Additionally, while providing the user with improved control, the angle of rotation, phi, also remains compliant such that it may be adjusted, based on joint limiting, by the device module 7017, shown in FIGS. 31A and 31B, so that the prosthetic end point 7122 may achieve movement in the commanded direction.

Although the angle of rotation, phi, has been described as being a user controllable input, in some embodiments, the user may not have control over the angle of rotation, phi, for example if the user decides that the cognitive burden of an additional control input is too great. In this embodiment, the device module 7017, shown in FIGS. 31A and 31B, may instead minimize the angle of rotation, phi, when adjusting the angle of rotation, phi, based on joint limiting and position limiting as discussed above. However, as with the previous embodiment, the device module 7017, shown in FIGS. 31A and 31B, may attempt to maintain the previously defined angle of rotation, phi, whenever possible while commanding movement of the prosthetic end point 7122.

As discussed above, the pitch $\theta_{Pitch}$, roll $\theta_{Roll}$ and yaw $\dot{\theta}_{Yaw}$ signals generated by the IMUs 7096, shown in FIG. 32, may be mapped either to the position or the velocity of the prosthetic end point 7122. In some embodiments, a faster or larger orientation change or rate of change of an IMU 7096 may translate to a higher speed of movement of the prosthetic device 7012. Thus, in these embodiments, the faster an orientation changes, the faster the prosthetic device 7012 moves. However, in other embodiments, the control system may not include a speed variant, but rather the device module 7017, shown in FIGS. 31A and 31B, may only command directional movement at preset speeds. In some embodiments, the larger movements by the prosthetic device 7012 may be quicker in speed for the first 80% of the desired movement, but may gradually slow for the last 20% of the desired movement to allow for more fine point control as the prosthetic end point 7122 reaches the desired location 7124. For example, in some embodiments, when moving toward the user's face, the prosthetic device 7012 may slow down when approaching or getting close to the face. This area of reduced speed may be programmed directly into the end point control by defining a portion of the movement envelope near the user's face as a slow speed area. This functionality may beneficially make use of the prosthetic device 7012 more comfortable and/or safe for the user. In some embodiments, the speed of particular prosthetic joints of the prosthetic device 7012 may also be varied over the range of motion of the prosthetic joint, for example, an elbow joint may slow down as it becomes more flexed.

Thus, in some embodiments, independent of user input, the control system may slow or quicken automatically based on preprogrammed speed controls. Thus, this may expand/improve the control resolution in one or more areas of the envelope.

As discussed above, in some embodiments, the speed of the various movements of the prosthetic device 7012 may be controlled using the IMUs 7096, and in some embodiments, it may be desirable to allow limits to the speed of one or more types of movement of the prosthetic device 7012 to be customized into the control system. Since some joints of the prosthetic device 7012 may need to actuate to a greater degree than other joints to reach the desired location 7124, depending upon the location of the desired location 7124 relative to the prosthetic end point 7122, the velocity limit may be unique for that x, y, z location of the desired location 7124. In some embodiments, the following method may be used by the device module 7017 to calculate the maximum speed. The steps include calculating the angles to reach the desired position; if any one of the angles exceeds the maximum difference allowed from the current position, then the device module 7017 assumes the ratio of the angle is the same. Thus, if the difference required at X degree angle change and the maximum allowed angle change is Xmax, the maximum vector length that is reachable is Xmax/X where X is the desired vector length. The new vector length may then be used as the desired input.

Figure 45:
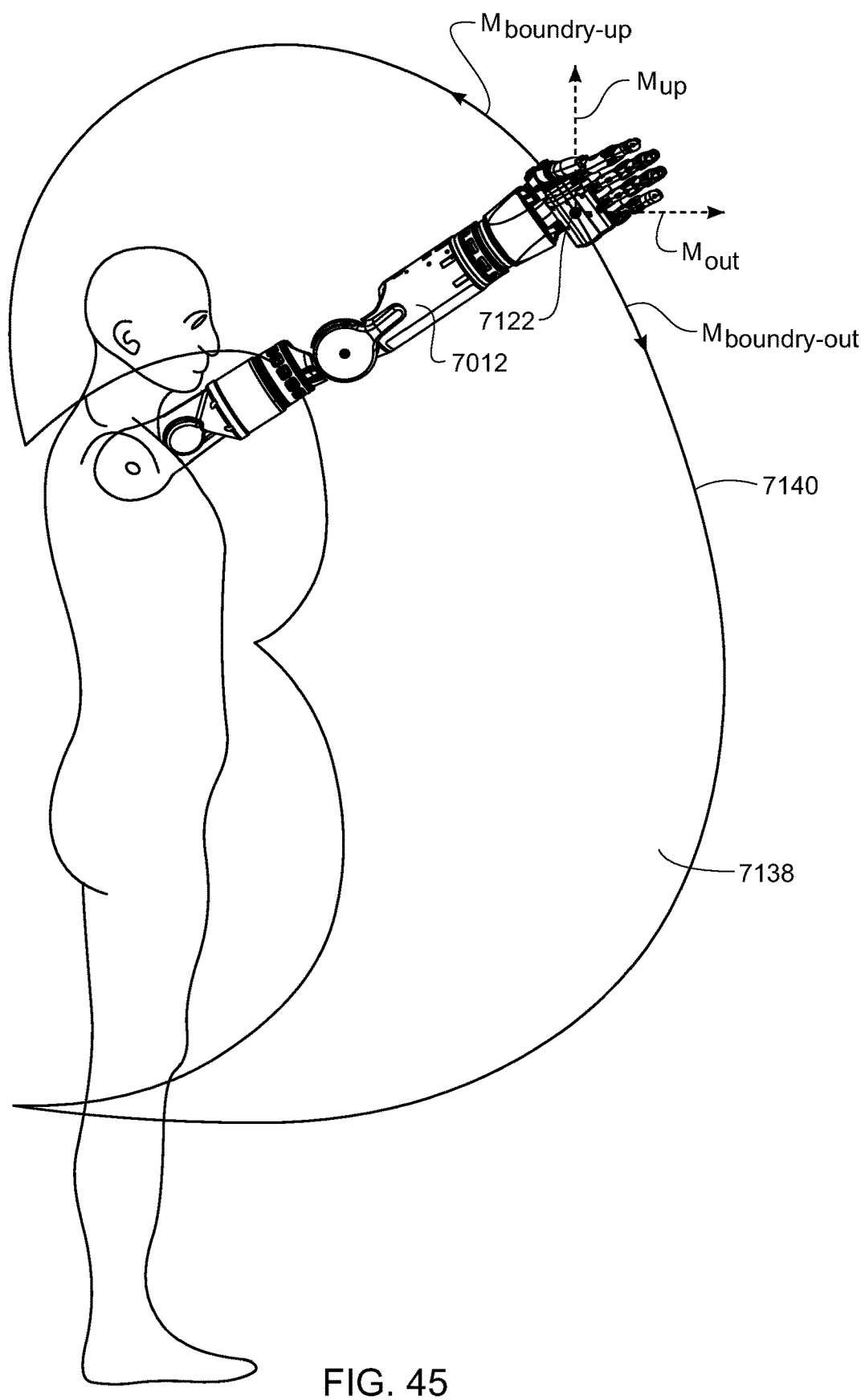
FIG. 45 is side view of the bulk control of FIG. 44A.

Referring to FIG. 45, the prosthetic device 7012 has a movement envelope 7138 for position limiting that includes a boundary 7140 that limits where the prosthetic end point 7122 of the prosthetic device 7012 is able to move relative to the user. The movement envelope 7138 is dependent upon the length of the prosthetic device 7012, the length of the various segments of the prosthetic device 7012 and movement limitations of the joints of the prosthetic device 7012. The prosthetic end point 7122 may reach only desired locations 7124, shown in FIG. 40, that are on or within the movement envelope 7138. For example, with the prosthetic device 7012 in the position shown, upward movement $M_{Up}$ of the prosthetic end point 7122 would require the prosthetic end point 7122 to move outside of the movement envelope 7138 and, therefore, cannot be executed. However, rather than simply preventing movement outside of the movement envelope 7138 by stopping the prosthetic device 7012, the device module 7017, shown in FIGS. 31A and 31B, may instead follow the closest possible movement path by commanding movement along the boundary 7140 of the movement envelope 7138 that includes a component of the commanded movement.

For example, as discussed above, with the prosthetic device 7012 in the position shown, if the user commands upward movement $M_{Up}$ of the prosthetic end point 7122, the end point 7122 would need to move outside of the movement envelope 7138, which is not possible. Therefore, upon receipt of a signal corresponding to upward movement $M_{Up}$, the device module 7017, shown in FIGS. 31A and 31B, may instead command movement $M_{Boundary\_Up}$ along the boundary 7140, which includes an upward component, but also an inward component. Similarly, if the user commands outward movement $M_{Out}$ of the prosthetic end point 7122, the end point 7122 would again need to move outside of the movement envelope 7138, which is not possible. Therefore, upon receipt of a signal corresponding to outward movement $M_{Out}$, the device module 7017, shown in FIGS. 31A and 31B may instead command movement $M_{Boundary\_Out}$ along the boundary 7140, which includes an outward component, but also a downward component.

Thus, this embodiment of the present invention is beneficial since it prevents the prosthetic device 7012 from becoming stuck in a position along the boundary 7140 of the movement envelope 7138 simply because the boundary 7140 has been reached. Although shown in two dimensions for simplicity, it should be understood by those skilled in the art that the movement envelope 7138 will actually limit movement of the prosthetic device 7012 in three dimensional space for a prosthetic device 7012 that is able to move in three dimensions.

Figure 46:
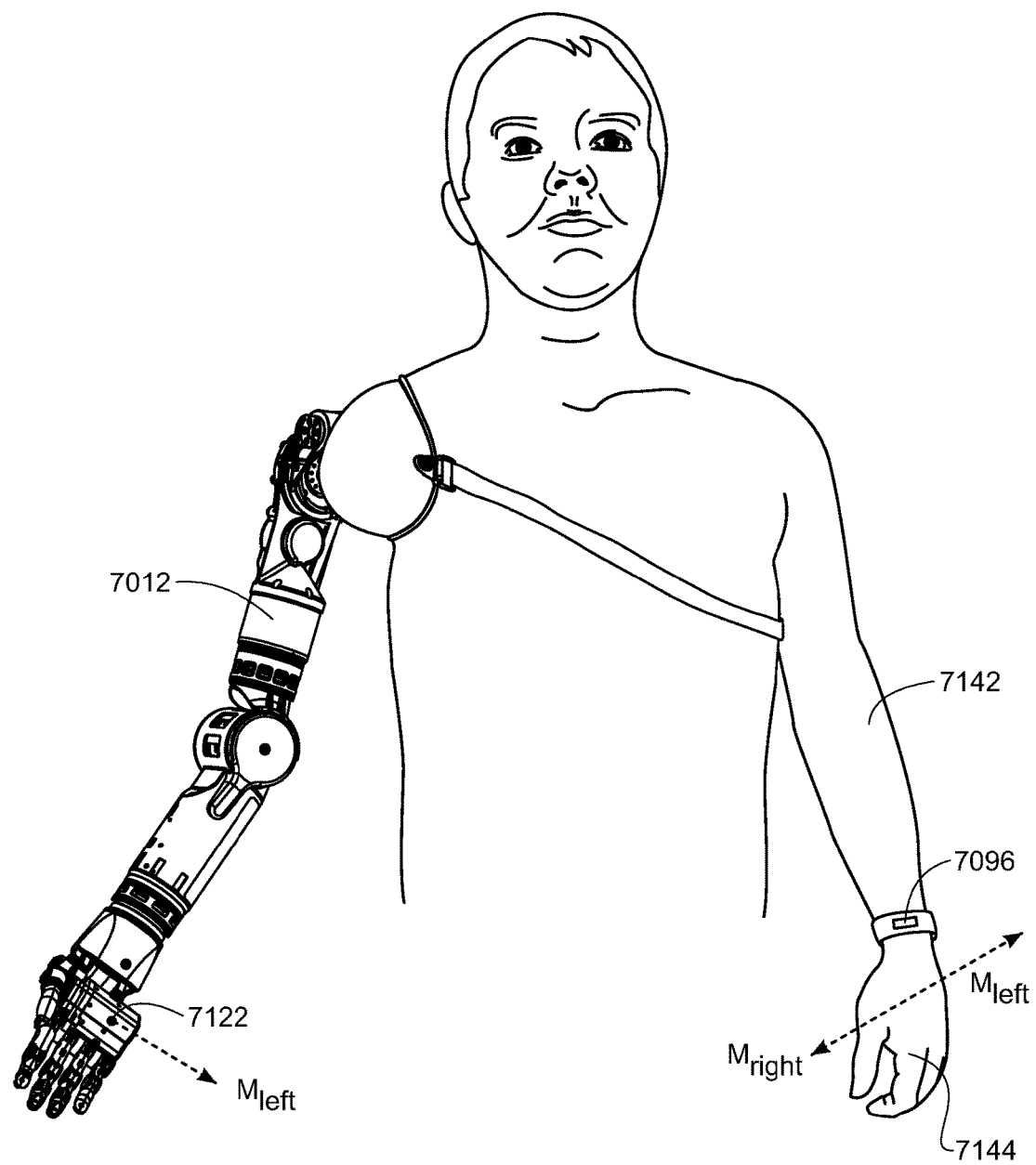
FIG. 46 is a side perspective view of a control mode according to an embodiment of the present invention.

Referring to FIG. 46, in some embodiments, another IMU 7096 may be used to measure the orientation of another part of the user's body, such as the user's arm 7142 or hand 7144. In this embodiment, the device module 7017, shown in FIGS. 31A and 31B, may enter a mimic mode to control bulk movement of the prosthetic device 7012, in such a manner that the device module 7017, shown in FIGS. 31A and 31B, will command the prosthetic device 7012 to move the prosthetic end point 7122 to substantially mimic the movement of the IMU 7096 on the user's arm 7142 or hand 7144. Thus, for example, if the user moves the IMU 7096 to the left, the device module 7017 will move the prosthetic end point 7122 to the left. In another embodiment, using the IMU 7096 on the user's arm 7142 or hand 7144, the device module 7017, shown in FIGS. 31A and 31B, may command the prosthetic device 7012 to move the prosthetic end point 7122 to substantially mirror the movement of the IMU 7096. Thus, for example, if the user moves the IMU 7096 to the right, the device module 7017 will move the prosthetic end point 7122 to the left. Accordingly, although some of the exemplary embodiments described herein referring to the use of a user's foot or feet to control a prosthetic device 7012, in other embodiments, other body parts of the user may be used to provide orientation information.

Figure 47:
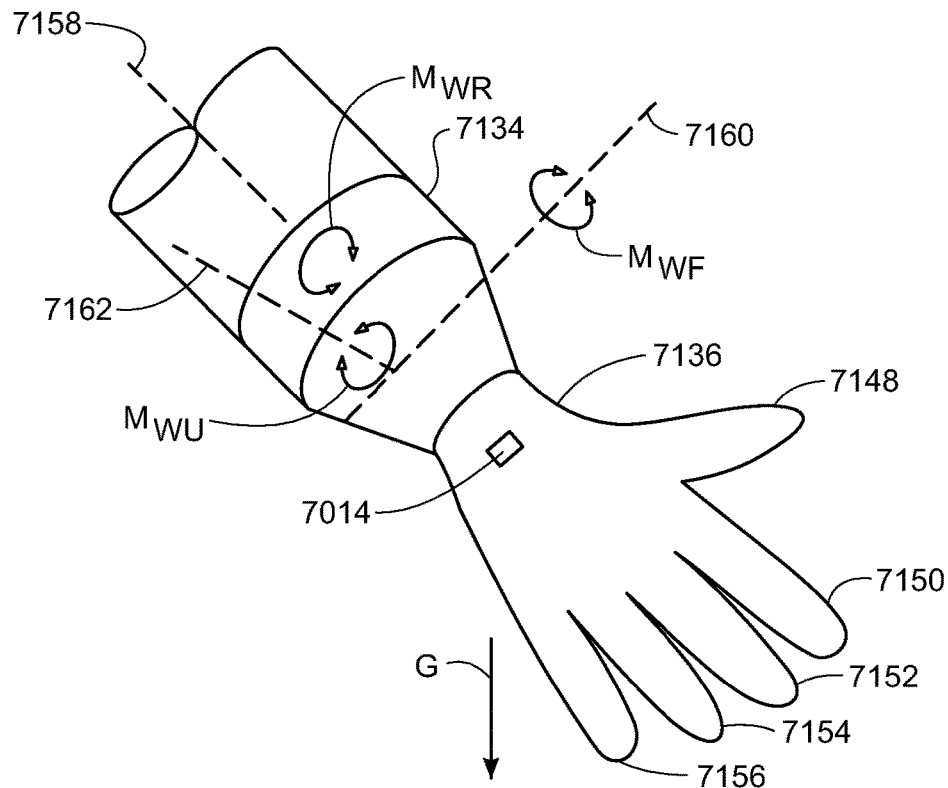
FIG. 47 is an enlarged perspective view of a finesse control mode according to an embodiment of the present invention.

Referring to FIG. 47, as discussed above, finesse movement relates to manipulating an object and specifically relates to operating the prosthetic hand 7136 and the prosthetic wrist 7134. Operation of the prosthetic hand 7136 may include grip selection and/or actuation and includes movement of a thumb structure 7148, an index structure 7150, a middle structure 7152, a ring structure 7154 and a pinky structure 7156, as will be discussed in greater detail below. Wrist operation may include wrist rotation $M_{WR}$ about a wrist rotation axis 7158, wrist flexion $M_{WF}$ about a wrist flexion axis 7160 and wrist deviation $M_{WD}$ about a wrist deviation axis 7162. When in finesse mode, the signals from sensors 7018 and/or IMUs 7096, shown in FIGS. 31A and 31B, are used by the device module 7017, shown in FIGS. 31A and 31B, to command the various wrist movements discussed above. For example, $M_{Roll}$ may be used to command $M_{WR}$, $M_{Pitch}$ may be used to command $M_{WF}$ and $M_{Yaw}$ may be used to command $M_{WD}$. Additionally, in some embodiments wrist flexion and wrist deviation may be couple together such that the prosthetic wrist 7134 follows a fixed path that includes some degree of wrist flexion $M_{WF}$ and some degree of wrist deviation $M_{WD}$. This embodiment is advantageous because it allows a single input, for example $M_{Pitch}$, to move the prosthetic wrist 7134 along the fixed path, thereby controlling both wrist flexion $M_{WF}$ and wrist deviation $M_{WD}$ with the single input.

In some embodiments, where the prosthetic wrist 7134 is provided with three degrees of freedom, i.e. wrist rotation $M_{WR}$, wrist flexion $M_{WF}$ and wrist deviation $M_{WD}$, particular control schemes may be used with respect to the wrist flexion and deviation. For example, a gravity based control scheme may be provided where signals from the IMUs 7096, shown in FIGS. 31A and 31B, may control up/down and left/right movement of the wrist independent of the wrist rotation position, rather than individually controlling the wrist flexion $M_{WF}$ and wrist deviation $M_{WD}$. Additionally, the gravity based control scheme may maintain an object held by the prosthetic hand 7136 at a specific orientation relative to gravity if the control mode is switched from finesse mode to bulk mode. This may be accomplished, for example, by providing a sensor 7018 on/or within the prosthetic hand 7136 for measuring the direction of the gravity vector G. The gravity based control scheme may be activated or deactivated in a manner similar to mode switching, for example by activating a switch or sensor. This gravity based control scheme may be particularly beneficial if the user is holding am object that could spill if inverted, such as a glass of water or the like.

In another control scheme, a single input may again be used by the device module 7017, shown in FIGS. 31A and 31B, to control both wrist flexion $M_{WF}$ and wrist deviation $M_{WD}$, which may be of particular use where only two degrees of freedom for control input are available. In such an embodiment, the controlled movement may be made orientation dependant. For example, the control signal may control wrist flexion $M_{WF}$ when the prosthetic hand 7136 is facing palm down but may control wrist deviation $M_{WD}$ when the prosthetic hand 7136 is facing palm sideways.

Figure 48:
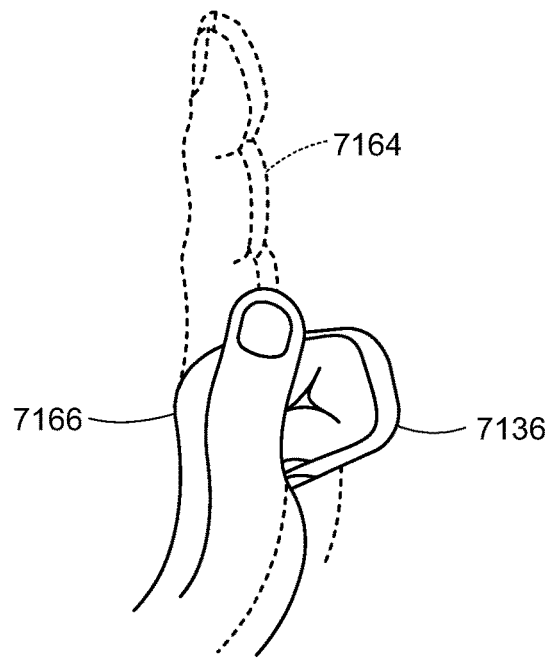
FIG. 48 is a side view of another embodiment of a finesse mode.
Figure 49A:
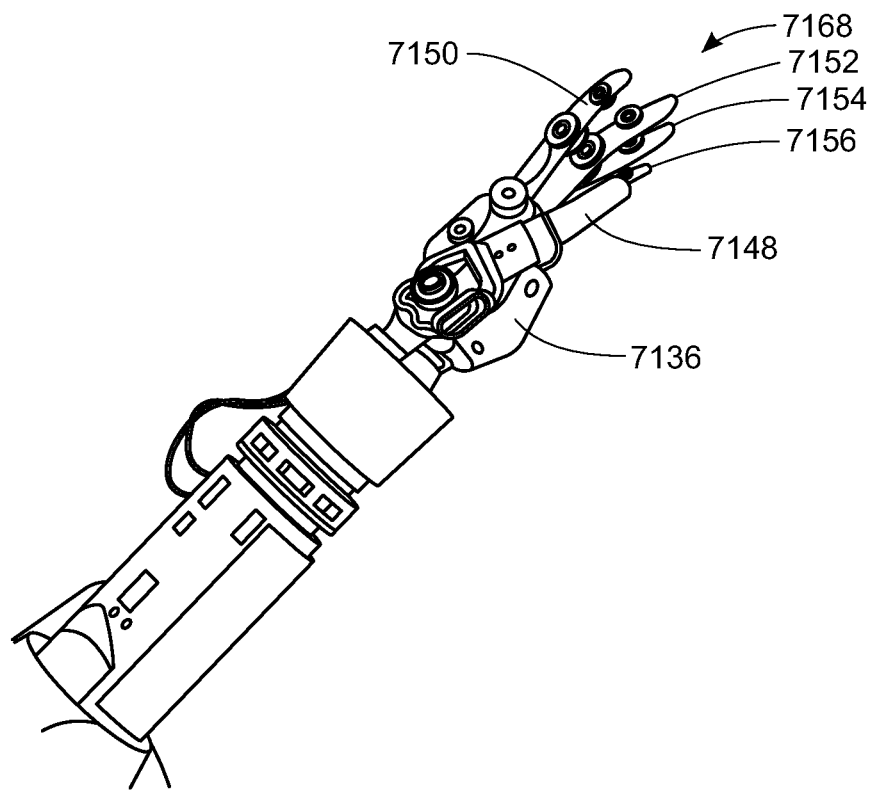
FIGS. 49A-49D are an embodiment of a finesse mode grip according to the present invention.
Figure 49B:
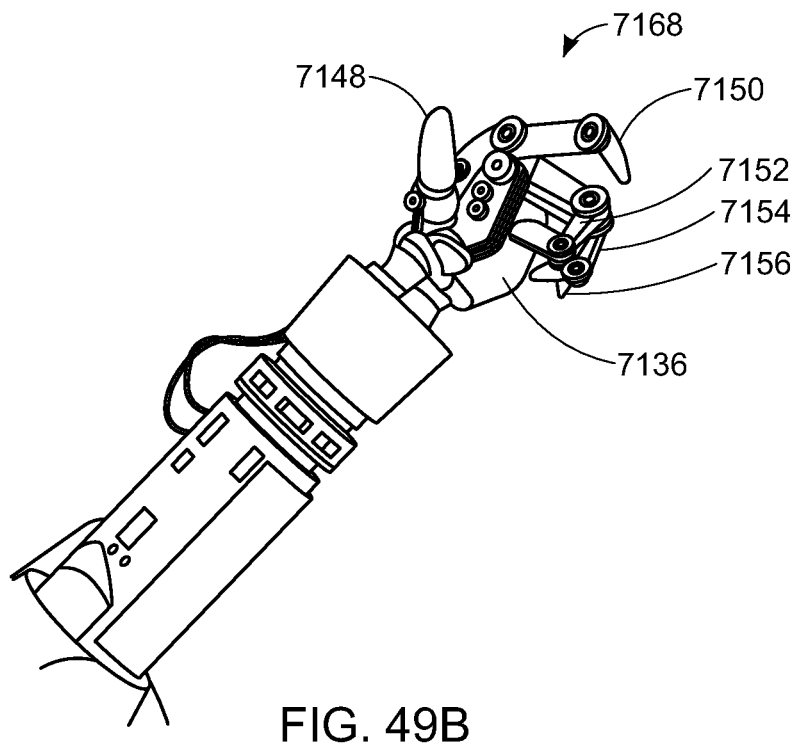
Figure 49C:
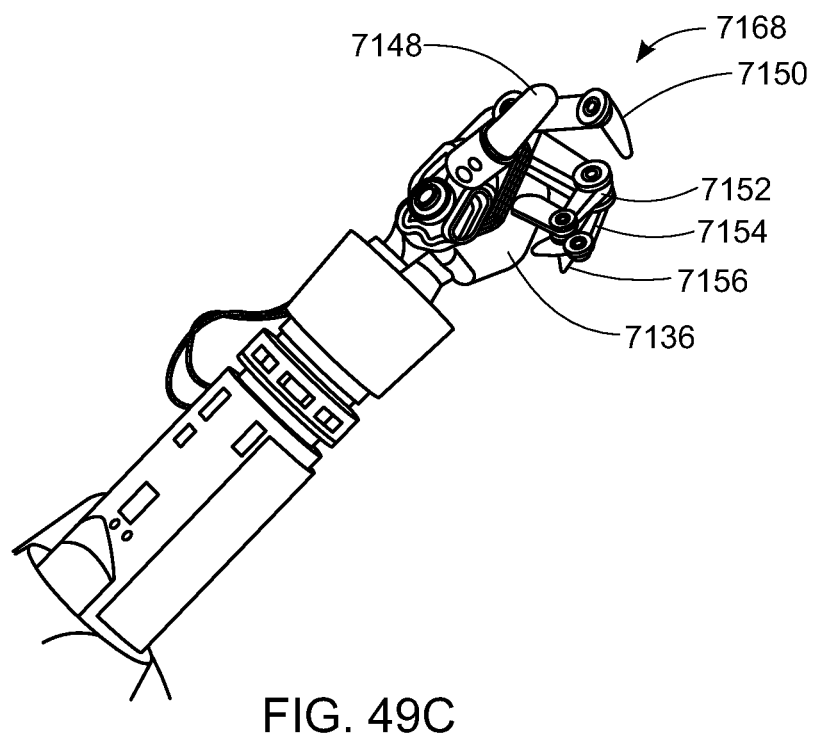
Figure 49D:
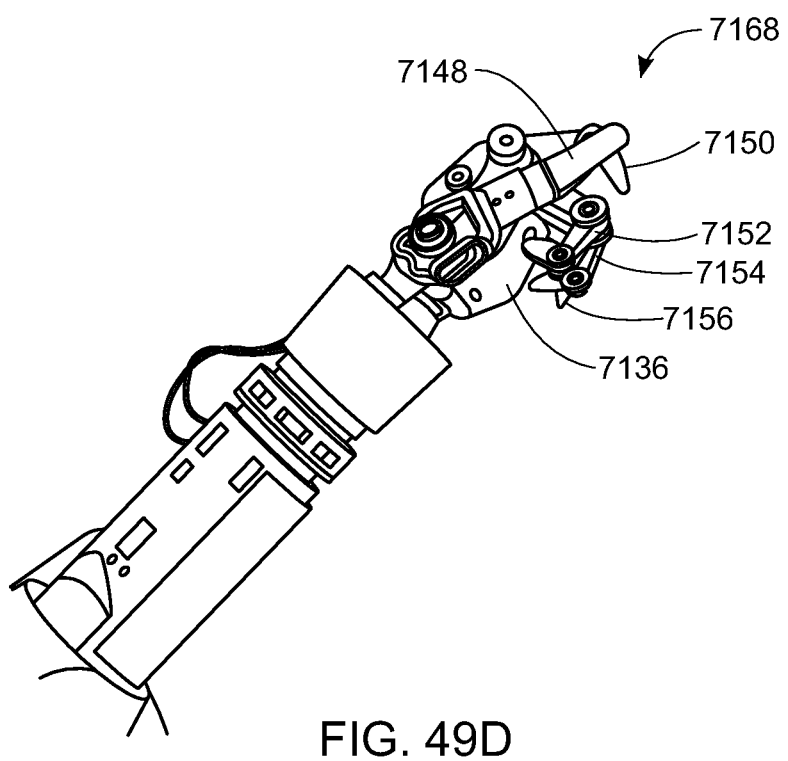

In addition to control of the prosthetic wrist 7134, finesse mode also provides for control of the prosthetic hand 7136. In particular, finesse mode provides control for grip selection and actuation. Referring to FIG. 48, as used herein, a grip refers to the range of motion through which the prosthetic hand 7136 passes from a fully open position 7164 to a fully closed position 7166. In some embodiments, the signals from the IMU 7096 and/or sensors 7018, shown in FIGS. 31A and 31B, allow the user to both fully or partially actuate each grip. For example, the user may make the grip begin to close by pitching the IMU 7096 to generate the pitch signal $\theta_{Pitch}$. However, if the user returns the IMU 7096 to the zero position, the grip maintains its altered position. Then the user may continue to close the grip by pitching the IMU 7096 again or, alternatively, may open the grip by pitching the IMU 7096 in the opposite direction.

In some embodiments, the device module 7017, shown in FIGS. 31A and 31B, includes a plurality of different preprogrammed grips that are selectable by the user. For example, the user may program specific input signals from the IMUs 7096 and/or sensors 7018, shown in FIGS. 31A and 31B, to correspond to the specific grips. In one embodiment, the user may set fore and aft pitch $\theta_{Pitch}$ and left and right roll $\theta_{Roll}$ detected by the IMU 7096 to correspond to four different hand grips. In another embodiment, as discussed above, one or more signals from the IMUs 7096 may be programmed to cycle forward or backward through a list of grips, thereby allowing the user to cycle through all of the preprogrammed grips using a single IMU orientation signal. For example, left and right roll $\theta_{Roll}$ detected by the IMU 7096 may allow the user to cycle through the list of grips and fore and aft pitch $\theta_{Pitch}$ may then allow the user to actuate, i.e. open and close, the selected grip.

In one embodiment, the device module 7017, shown in FIGS. 31A and 31B, includes six different preprogrammed grips that each close the thumb structure 7148, index structure 7150, middle structure 7152, ring structure 7154 and pinky structure 7156 in varying manners and with varying trajectories. For example, referring to FIGS. 49A-49D, a "key grip" 7168, which may also be referred to as a "lateral pinch grip", may first close the index structure 7150, middle structure 7152, ring structure 7154 and pinky structure 7156, while moving the thumb outward to a "thumbs up" position. Then, the thumb structure 7148 may be lower to contact the index structure 7150. This key grip allows the user to hold an object (not shown) within the palm of the prosthetic hand 7136 or to pinch an object (not shown) between the thumb structure 7148 and the index structure 7150. Additionally, the user may halt actuation midway through the key grip 7168, for example, to signal a "thumbs up." The key grip 7168 also includes a dressing position within its trajectory that may assist the user in putting the prosthetic hand through a shirt or coat sleeve. The key grip 7168 also includes a handle position within its trajectory in which the index structure 7150, middle structure 7152, ring structure 7154 and pinky structure 7156 begin to close to facilitate the grasping of a handle, such as the handle of a briefcase.

Figure 50A:
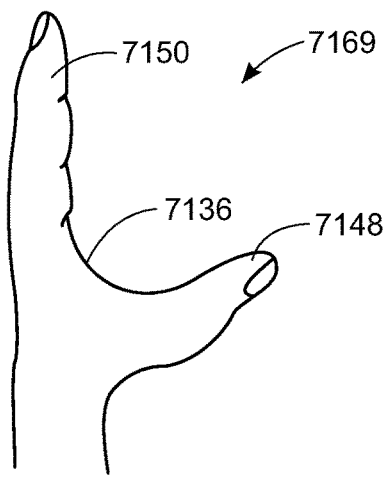
FIGS. 50A and 50B are another embodiment of a finesse mode grip according to the present invention.
Figure 50B:
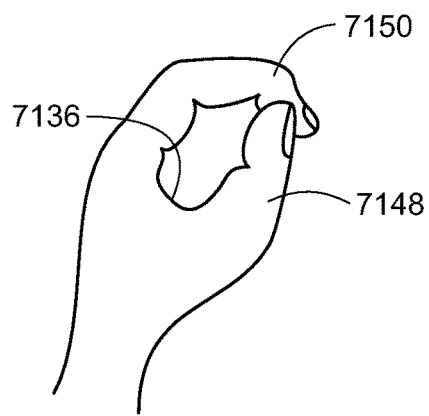

Referring to FIGS. 50A-50B, the control system may also be preprogrammed with a power grip 7169. The power grip 7169 is similar to the key grip 7168, shown in FIGS. 49A-49D, in that the index structure 7150, middle structure 7152, ring structure 7154 and pinky structure 7156 are closed first, while the thumb structure 7148 is moved to be perpendicular to the palm of the prosthetic hand 7136. Then, the thumb structure 7148 is closed laterally along the index structure 7150 into a fist.

Figure 51:
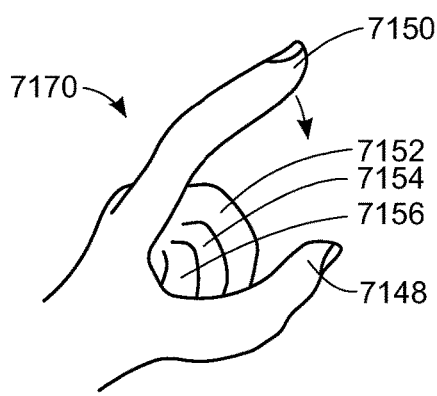
FIG. 51 is another embodiment of a finesse mode grip according to the present invention.

Referring to FIG. 51, the control system may also be preprogrammed with a tool grip 7170. The tool grip 7170 first closes the thumb structure 7148, middle structure 7152, ring structure 7154 and pinky structure 7156. Once closed, the index structure 7150 is then closed as well. This grip is advantageous because it allows the user to grip a hand tool (not shown), such as a drill, or another similar object and then activate the control for the hand tool, such as a drill trigger. Additionally, the user may halt actuation midway through the grip to provide a hand configuration useful for pointing at objects.

Figure 52:
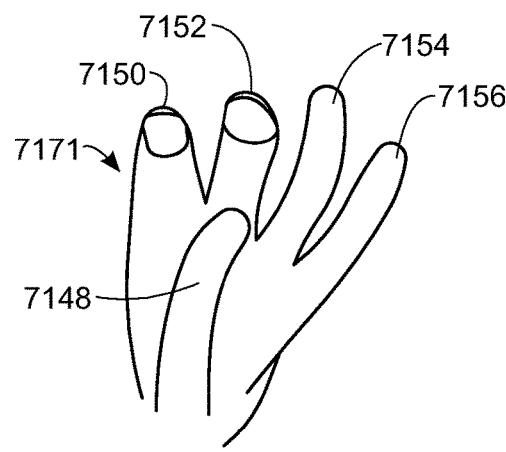
FIG. 52 is another embodiment of a finesse mode grip according to the present invention.

Referring to FIG. 52, the control system may also be preprogrammed with a chuck grip 7171 in which the orientation of the thumb structure 7148, index structure 7150 and middle structure 7152 is critical. The chuck grip 7171 closes the thumb structure 7148 toward the base of the middle structure 7152, while simultaneously closing the index structure 7150, middle structure 7152, ring structure 7154 and pinky structure 7156 to bring the thumb structure 7148 to the index structure 7150 and middle structure 7152.

Figure 53:
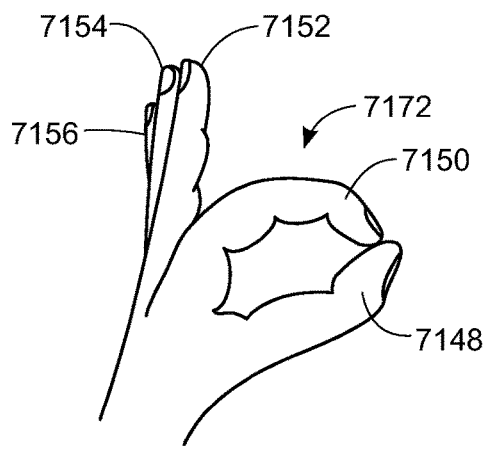
FIG. 53 is another embodiment of a finesse mode grip according to the present invention.

Referring to FIG. 53, the control system may also include a preprogrammed pinch open grip 7172. The pinch open grip 7172 leaves the middle structure 7152, the ring structure 7154 and the pinky structure 7156 open and brings the tip of the thumb structure 7148 and the tip of the index structure 7150 together to allow the user to pick up small objects (not shown).

Figure 54:
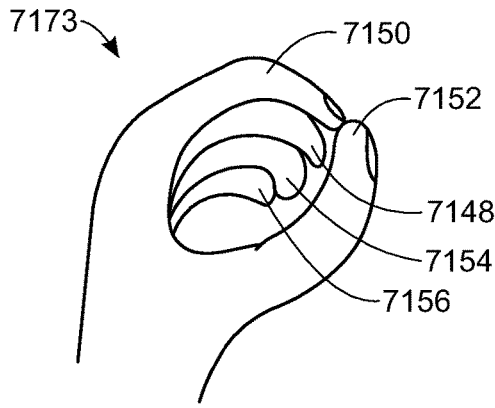
FIG. 54 is another embodiment of a finesse mode grip according to the present invention.

Referring to FIG. 54, the control system may also include a preprogrammed pinch closed grip 7173. The pinch closed grip 7173 first closes the middle structure 7152, the ring structure 7154 and the pinky structure 7156 and then brings the tip of the thumb structure 7148 and the tip of the index structure 7150 together to allow the user to pick up small objects (not shown), while moving the unused finger structures out of the way. Additionally, in some embodiments, once the middle structure 7152, the ring structure 7154 and the pinky structure 7156 are closed, this intermediate state of the pinch closed grip 7173 may advantageously be used as a pointer.

The position of the fingers/thumbs one to another in the various grips may be preprogrammed to maximize the effectiveness of the grips. For example, in the chuck grip and the power grip, the angle of orientation of the thumb with respect to the fingers may be changed in the control system to optimize the grips. In some embodiments, the thumb positioning and various grip trajectories may be determined through one or more user studies and/or user input to optimize one or more grips.

Although described as having six grips, it should be understood by those skilled in the art that the device module 7017 may be preprogrammed with essentially an infinite number of varying grips. In some embodiments, the infinite number of grips may be those mid-grips or grips formed while the hand is closing to one of the six grips described above. Additionally, although the signals from the IMU 7096 and the sensors 7018 have been described as corresponding to specific joint movements and grips for exemplary purposes, it should be understood that $M_{Pitch}$, $M_{Roll}$, $M_{Yaw}$, $M_{Pitch}'$, $M_{Roll}'$, $M_{Yaw}'$ and the signals from sensors 7018 may each be programmed in the device module 7017 to correspond to any of the joint movements or grips, depending upon user preference.

In some embodiments, it may be beneficial to provide tactile feedback to the user, which may be a vibration, buzz or other, signaling to the user that the hand is grasping. The tactile feedback may be generated by one or more feedback sensors 14, shown in FIG. 1A, within the prosthetic hand 7136 such as pressure sensors or force sensing resistors. In some embodiments, the tactile feedback may signal to the user the strength of the grip. In some embodiments, where the user is maintaining a steady grip, i.e., no change in grip strength, the vibration or buzz may stop to signal to the user that the grip is maintaining a desired force rather than changing the exerted force. In some embodiments, a/the change in force/grip is indicated rather than a constant feedback where there is no change.

In some embodiments, the system may include user control of compliance for appropriate circumstances. For example, but not limited to, where the user commands the thumb and index finger to close and the user continues to command the system to close even after the fingers are already closed, in some embodiments, this may signal the system to back out compliance. This may provide a more forceful grip and the system may continue to increase the stiffness as user continues to command increased closing. Thus, in some circumstances, the system may lock out compliance. This may be beneficial in making the fingers stiffer by measuring force and controlling the force (i.e., force control). This control system may be additionally beneficial for it includes improved interpretation of user commands.

In some embodiments, for example, in lateral pinch grip, force feedback may be used. For example, but not limited to, where the index finger and thumb close on each other. At a predetermined point, the index finger compliance bottoms out and the index finger position is maintained. The thumb may continue to exert force onto the index finger until maximum torque is being exerted onto the index finger.

Figure 55:
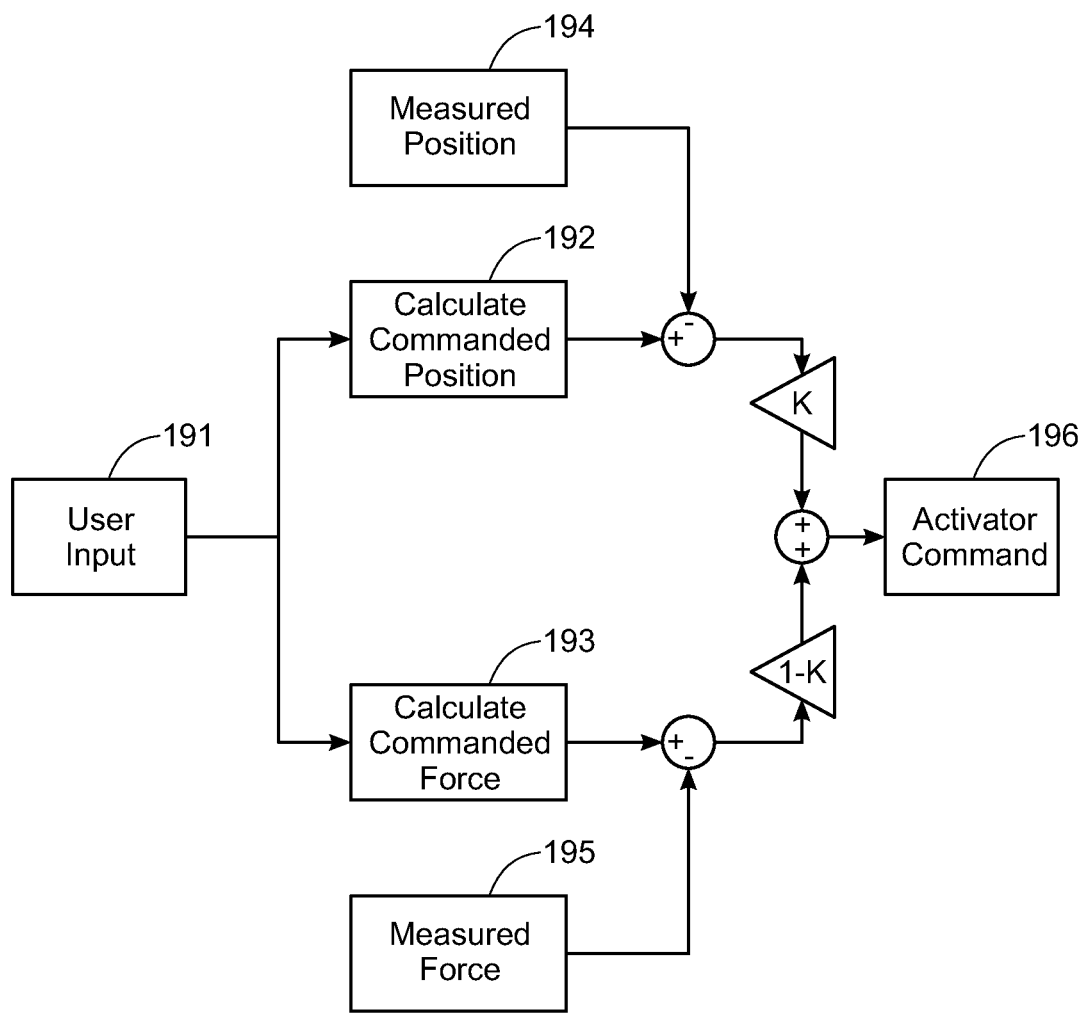
FIG. 55 is a control diagram of an embodiment of finesse control according to the present invention.

Referring to FIG. 55, in some embodiments, the device module 7017, shown in FIGS. 31A and 31B, may control grip movement based on both position and force using compliance sensor, e.g. the one or more feedback sensors 14, shown in FIG. 1A, within the prosthetic hand 7136, shown in FIGS. 49A-49D. For example, the device module 7017, shown in FIGS. 31A and 31B, receives a user input command 191 for grip movement, e.g. grip closure, from the IMU 7096, shown in FIG. 32. The device module 7017, shown in FIGS. 31A and 31B, interprets this user input command 191 as a commanded position 192. For example, in some embodiments, the device module 7017, shown in FIGS. 31A and 31B, may simply multiply the user input command 191 by a gain factor to calculate the commanded position 192, while in other embodiments, a more complex calculation may be implemented to calculate the commanded position 192 by the device module 7017, shown in FIGS. 31A and 31B. The device module 7017, shown in FIGS. 31A and 31B, also interprets this user input command 191 as a commanded force 193. For example, in some embodiments, the device module 7017, shown in FIGS. 31A and 31B, may simply multiply the user input command 191 by a gain factor to calculate the commanded force 193, while in other embodiments, a more complex calculation may be implemented to calculate the commanded force 193 by the device module 7017, shown in FIGS. 31A and 31B. The device module 7017, shown in FIGS. 31A and 31B, calculates the difference between the commanded position 192 and a measured position 194 detected by one or more position feedback sensors 14, shown in FIG. 1A, within the prosthetic hand 7136, shown in FIGS. 49A-49D. Similarly, the device module 7017, shown in FIGS. 31A and 31B, calculates the difference between the commanded force 193 and a measured force 195 detected by one or more compliance sensors 14, shown in FIG. 1A, within the prosthetic hand 7136, shown in FIGS. 49A-49D. The device module 7017, shown in FIGS. 31A and 31B, then adds the difference in the commanded position 192 and the measured position 194, multiplied by a gain factor k, to the difference in the commanded force 193 and the measured force 195, multiplied by a gain factor of 1−k, to determine a actuator command 196 for commanding movement of one or more of the thumb structure 7148, index structure 7150, middle structure 7152, ring structure 7154 and pinky structure 7156, all shown in FIGS. 49A-49D.

The gain factor k is a measured impedance between zero and one that is proportional to a displacement per applied force and is calculated using both the measured position 194 and the measured force 195. In some embodiments, the measured impedance may follow a linear scale, while in other embodiments, the measured impedance may represent a more complex relationship between displacement and force. Using the gain factor k for position and the gain factor 1−k for force advantageously provides a sliding scale between control based solely on position and control based solely on force. For example, when the measured force 196 is small, e.g. when the finger structures are not in contact with a surface, the gain factor k will approach one and positional control will dominate the actuator command 196. Conversely, when the measured force 196 is large and the displacement determined from the measured position 194 is small, e.g. when the finger structures are in contact with a surface, the gain factor k will approach zero and force control will dominate the actuator command 196. Thus, the device module 7017, shown in FIGS. 31A and 31B, advantageously controls grip movement based on positional control when movement of the thumb structure 7148, index structure 7150, middle structure 7152, ring structure 7154 and/or pinky structure 7156, all shown in FIGS. 49A-49D, is not impeded and automatically transitions to force control, based on the sliding scale set by the measured impedance, when movement is impeded.

When controlling grip movement, the device module 7017, shown in FIGS. 31A and 31B, preferable monitors the compliance sensors in both the thumb structure 7148 and index structure 7150, shown in FIGS. 49A-49D and sends actuator commands 196 to the motors of the thumb structure 7148 and index structure 7150, shown in FIGS. 49A-49D, that maintain forces that are approximately equal in amplitude to prevent one structure from pushing the other out of the way when gripping an object. In some embodiments, the device module 7017, shown in FIGS. 31A and 31B may match the forces by matching gain coefficients on the force control loops and ensuring that one finger structure does not exceed the force applied by the opposing finger structure.

While controlling grip movement, the device module 7017, shown in FIGS. 31A and 31B, advantageously monitors one or more positional feedback sensors and one or more compliance sensors within the prosthetic hand 7136, shown in FIGS. 49A-49D, and controls grip movement based on positional control, force control or some combination thereof based on the condition of the prosthetic hand 7136, shown in FIGS. 49A-49D. This control advantageously allows the user to command velocity along a specific trajectory and/or force of the finger structures in the direction of the trajectory with a single input. Switching between positional and force control, as discussed above, advantageously eliminates wind-up error that may occur when using only positional control to grip an object. For example, when gripping an object using only positional control, the device module 7017, shown in FIGS. 31A and 31B, attempts to alter the position of one or more of the thumb structure 7148, index structure 7150, middle structure 7152, ring structure 7154 and/or pinky structure 7156, all shown in FIGS. 49A-49D, relative to one another to increase force on the object, even though the object physically prevents the one or more finger structures from moving relative to one another. This attempted movement generates wind-up error that must then be unwound when backing off the movement and releasing the grip, which results in an undesirable delayed movement. Controlling grip movement through the sliding scale between positional control and force control based on the measured impedance eliminates this wind-up error and allows positional control to begin immediately upon a command from the IMU 7096, shown in FIG. 32, to back off movement and release the grip.

Figure 56:
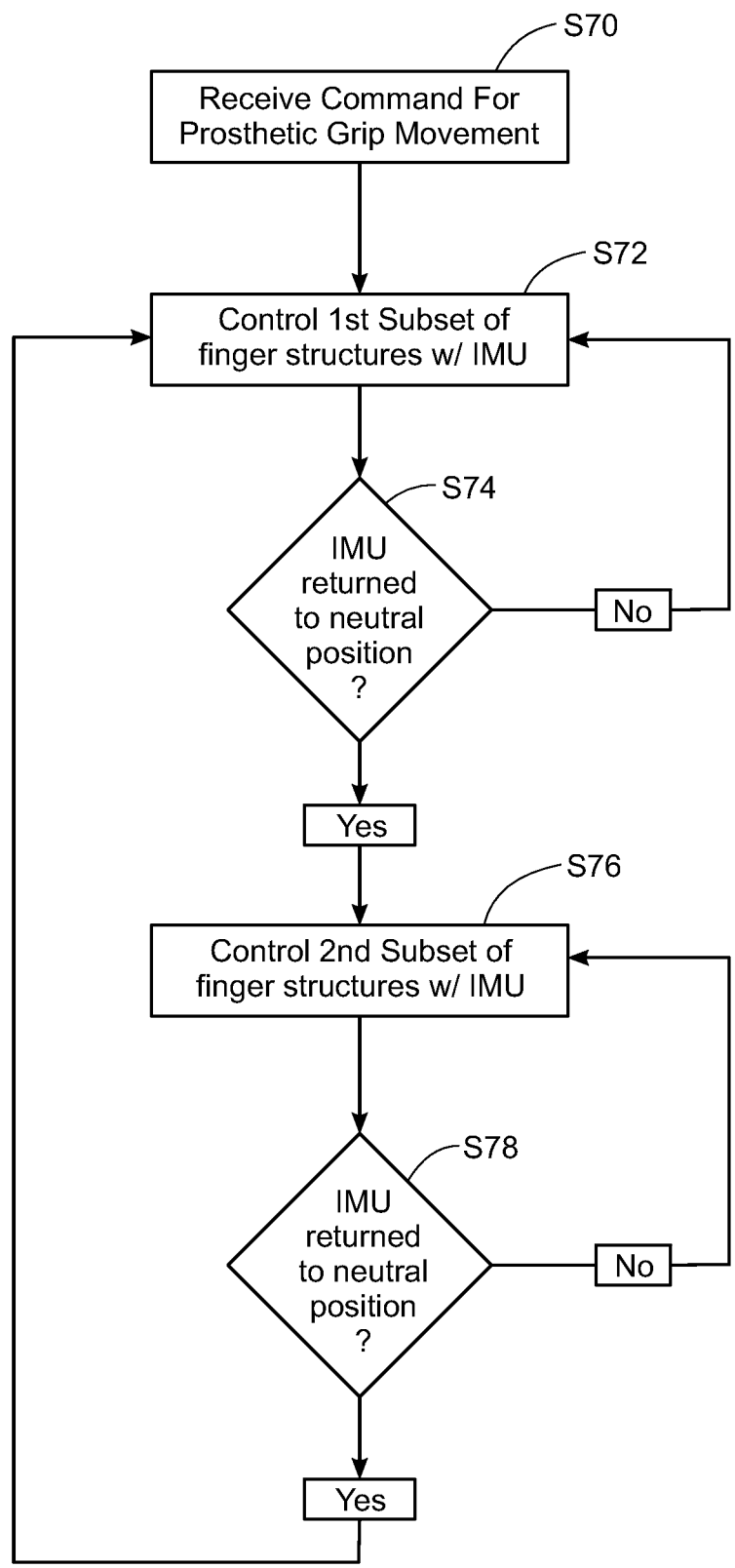
FIG. 56 is a process diagram of an embodiment of finesse control according to the present invention.

Referring to FIG. 56, an embodiment for controlling grip movement using subsets of joints upon receipt of a command for grip movement in S70 is shown. The device module 7017, shown in FIGS. 31A and 31B, initially controls a first subset of finger structures using signals from the IMU 7096, shown in FIG. 32, in S72. The first subset of finger structures may include one or more of the thumb structure 7148, index structure 7150, middle structure 7152, ring structure 7154 and pinky structure 7156, all shown in FIGS. 49A-49D. For example, in some embodiments, the first subset includes the middle structure 7152, ring structure 7154 and pinky structure 7156, all shown in FIGS. 49A-49D, such that the thumb structure 7148 and index structure 7150, shown in FIGS. 49A-49D, remain stationary while the device module controls the first subset of finger structures. In S74, the device module 7016, shown in FIGS. 31A and 31B, monitors the position of the IMU 7096, shown in FIG. 32, to determine if the IMU 7096, shown in FIG. 32, has returned to a neutral position where grip movement is not commanded, e.g. a position where the user is neither commanding the grip to open nor close. If the IMU 7096, shown in FIG. 32, is not returned to the neutral position, the device module 7017, shown in FIGS. 31A and 31B, continues to control the first subset of finger structures using signals from the IMU 7096, shown in FIG. 32, in S72.

Alternatively, if the IMU 7096, shown in FIG. 32, is returned to the neutral position in S74, the device module 7017, shown in FIGS. 31A and 31B, begins to control a second subset of finger structures using signals from the IMU 7096, shown in FIG. 32, in S76. The second subset of finger structures may include one or more of the thumb structure 7148, index structure 7150, middle structure 7152, ring structure 7154 and/or pinky structure 7156, all shown in FIGS. 49A-49D. For example, in the exemplary embodiment discussed above, the second subset may include the thumb structure 7148 and index structure 7150, shown in FIGS. 49A-49D, such that the middle structure 7152, ring structure 7154 and pinky structure 7156, all shown in FIGS. 49A-49D, remain stationary while the device module controls the second subset of finger structures. In S78, the device module 7016, shown in FIGS. 31A and 31B, monitors the position of the IMU 7096, shown in FIG. 32, to determine if the IMU 7096, shown in FIG. 32, has returned to the neutral position where grip movement is not commanded, e.g. the position where the user is neither commanding the grip to open nor close. If the IMU 7096, shown in FIG. 32, is not returned to the neutral position, the device module 7017, shown in FIGS. 31A and 31B, continues to control the second subset of finger structures using signals from the IMU 7096, shown in FIG. 32, in S76. Alternatively, if the IMU 7096, shown in FIG. 32, is returned to the neutral position in S78, the device module 7017, shown in FIGS. 31A and 31B, switches to control the first subset of finger structures using signals from the IMU 7096, shown in FIG. 32, in S72. The device module 7017, shown in FIGS. 31A and 31B, may continue to switch between controlling the first subset and second subset of finger structures until the user exits the grip control mode.

This embodiment for controlling first and second subsets of finger structures during grip movement provides various advantages when implemented in conjunction with the various grips discussed above. For example, referring back to FIGS. 49A-49D, in the key grip 7168 the first subset may include the index structure 7150, middle structure 7152, ring structure 7154 and pinky structure 7156 while the second subset includes the thumb structure 7148. Thus, the user may be able to close the index structure 7150, middle structure 7152, ring structure 7154 and pinky structure 7156 and then move the thumb structure 7148 into and out of contact with the index structure 7150 multiple times to pinch and release objects. As should be understood by those skilled in the art, a similar benefit may be achieved in other grips such as the pinch closed grip 7173, shown in FIG. 54, discussed above by including the middle structure 7152, the ring structure 7154 and the pinky structure 7156 in the first subset and including the thumb structure 7148 and the index structure 7150 in the second subset. Referring back to FIG. 51, the tool grip 7170 may advantageously include the thumb structure 7148, middle structure 7152, ring structure 7154 and pinky structure 7156 in the first subset and the index structure 7150 in the second subset. This advantageously allows the user to first control the thumb structure 7148, middle structure 7152, ring structure 7154 and pinky structure 7156 to be closed using the first subset, for example to grip a drill handle. Once closed, the user may then control the second subset to open and closed the index structure 7150 multiple times to activate the tool controls, such as the drill trigger, without the risk of releasing and dropping the tool handle. Although these grips have been described for exemplary purposes, it should be understood by those skilled in the art that a variety of benefits and advantages may be achieved by controlling various other grips using the first and second subsets of finger structures during grip movement.

Referring back to FIG. 32, in some embodiments, where the control system includes 2 IMUs 7096, one on each of the user's feet 7021, the control system may include moving platform detection. For example, the device module 7017, shown in FIGS. 31A and 31B, may disregard signals generated by the IMUs 7096 when the signals indicative of pitch $\theta_{Pitch}$, roll $\theta_{Roll}$ and/or yaw $\dot{\theta}_{Yaw}$ generated by both IMUs 7096 are substantially identical. The device module 7017 will assume that the substantially identical signals generated by the two IMUs 7096 are due to accelerations from the user's environment, for example if the user is riding in a vehicle such as car, a train, a plane or the like, rather than intended commands. It should be appreciated that in some embodiments of moving platform detection, a delta or differential between the two IMUs 7096 may be used to command the prosthetic device 7012. In some embodiments, this may be a selectable mode that the user may elect during customization of the control apparatus 7010 so that the user may activate the mode upon entering the vehicle or the like.

Referring back to FIGS. 31A and 31B, in some embodiments, the control apparatus 7010 also includes a fail safe mode that the device module 7017 will enter if a fail condition or error condition is detected from feedback sensors 7014. For example, the device module 7017 may enter the fail safe mode if power to the system goes out unexpectedly or if communication with the IMUs 7096 is lost. In fail safe mode, the prosthetic device 7012 will remain in its current position and the prosthetic hand 7136 will open. The device module 7017 may turn the prosthetic actuators 7013 off and may engage brakes and/or clutches of the prosthetic device 7012. Other system failures or errors that will trigger a failsafe may include, but are not limited to, sensor faults, motor or actuator faults (e.g., over current or over temperature conditions), feedback position sensor signals out of a normal or expected range, or a communication loss or communication errors between the device module 7017 and the prosthetic device 7012.

In another embodiment of the present invention, the control apparatus 7010 may include a computer mode that may be switched on and/or off using any of the various IMUs 7096 and/or sensors 7014 described herein. When in the computer mode, body input signals from the IMUs 7096 and/or sensors 7014 may be used to control an associated external device, such as movement of a mouse on a computer screen, movement of a car, or movement of other similar remote-controlled devices.

In some embodiments, the control apparatus 7010 may be preprogrammed with specific macros that may be executed in response to a particular body input signal from one or more of the IMUs 7096 and/or sensors 7014. For instance, the specific macro may be a preprogrammed motion of the prosthetic device 7012 that is executed in response to a specific gesture, e.g., a double tap or a short tap of the foot 7021. In some embodiments, a macro may be programmed in real-time by the user, for example, to "record" a motion and an associated instigator of that motion. Thus, in some embodiments, the user may "record" a performed motion, and then, instigating the recording, the control apparatus 7010 may repeat the motion. For example, when eating and/or drinking, the user may find it helpful to record the specific motion and easily repeat the motion by creating a macro.

As discussed above, the device module 7017 includes a prosthetic controller 7027 that is in wireless or wired communication with the prosthetic device 7012. In the exemplary embodiment, the prosthetic device 7012 may regularly communicate actuator status information, e.g. position information, to the device module 7017 and listens for, and expects to receive, commands at regular intervals from the device module 7017. In some embodiments, if the prosthetic device 7012 does not receive commands from the device module 7017 within a pre-set amount of time, the prosthetic device 7012 may shut down its actuators 7013 and turn on brakes.

As discussed above, in certain embodiments of the present invention, there are a number of modes in the control system. Thus, in these embodiments, the pitch $\theta_{Pitch}$, roll $\theta_{Roll}$ and yaw $\dot{\theta}_{Yaw}$ signals from the IMU(s) 7096 may be translated to control different functions for each of the different modes. For example, the pitch signal $\theta_{Pitch}$ from one IMU 7096 may control left/right movement of the prosthetic end point 7122, shown in FIG. 40, in bulk mode and may control grip opening/closing movement in finesse mode. Additionally, if the control system includes other control modes, the pitch signal $\theta_{Pitch}$ from the IMU 7096 may also control other functions within each of those control modes.

In some embodiments, mode switching between the various control modes may be accomplished through an electrical switch or with one or more sensors 7018. Additionally, mode switching may be provided by moving the user's foot 7021 in a specific gesture that has been preprogrammed to be recognized by the device module 7017, e.g., a double tap or a short tap of the foot 7021. In other embodiments, mode switching may be accomplished using any other type of switch or signal, including, but not limited to, a myoelectric switch, such as those known in the art (e.g., in some embodiments of control of a prosthetic arm, for trans humeral users, the tricep and/or bicep and/or pectoral muscles may be used, or, for transradial users, forearm muscles may be used).

In the exemplary embodiment, the switch used to switch between the control modes may also be used to switch the prosthetic device 7012 and control apparatus 7010 from an "on" state to an "off" state. Additionally, in some embodiments, a short tap of the foot 7021 may switch the mode (i.e., from bulk mode to finesse mode and visa versa) and a double tap of the foot 7021 may switch the system from the "on" stated to the "off" state. It should be understood that the double tap could be done elsewhere on the user's body, i.e. in locations other than the foot, with another IMU 7096. In some embodiments, switching the control apparatus 7010 to the "off" state maintains the current position of the prosthetic device 7012, including the prosthetic hand 7136.

Still referring to FIGS. 31A and 31B, as discussed above, the control apparatus 7010 is in some embodiments, customized to the user. For instance, the correspondence between each of the signals generated by the IMUs 7096 and the control commands sent by the device module 7017 to the prosthetic device 7012 may be customized. In one embodiment, customized correspondence may be mapped in a matrix that is uploaded to device module 7017 of the control apparatus 7010. Then, when the device module 7017 receives orientation signals from the IMUs 7096, the device module 7017 is able to map the signal to the correct control command to be sent to the prosthetic device 7012.

In embodiments where the user is using one IMU 7096 per foot 7021, movements of each foot 7021 may be linked to or mapped to corresponding movements or types of movements for each mode of the prosthetic, i.e. bulk mode and finesse mode. In the exemplary embodiment, the customization allows assignment for each orientation signal generated from each IMU 7096 to include specifically whether the user desires: 1) the particular position of the IMU 7096 to control the position of one of the prosthetic joints; 2) the particular position of the IMU 7096 to control the velocity of one of the prosthetic joints; or 3) the rate of change of the IMU 7096 to control the velocity of one of the prosthetic joints. It should be noted that in various embodiments, in addition to the IMUs 7096, other inputs, e.g., sensors 7018 or EMG, may also be mapped to corresponding controls of the prosthetic device 7012. For example, EMG signals, in some embodiments, may also be mapped to movements and types of movements of the prosthetic device 7012.

As discussed above, the IMU signals may be assigned to control movements in each of the different control modes. Additionally, as discussed above, some sensor signals or IMU signals may be assigned to control mode switching (i.e., various foot taps may turn the system "on" or "off" and may switch the mode between bulk mode and finesse mode). This mode and on/off switching is also customizable in the exemplary embodiment. Additionally, some sensor and IMU signals may be assigned to toggle forward or backward through a list, i.e., to toggling through various grips of the prosthetic hand 7136, shown in FIG. 43. Thus, the present invention allows for full customization between the various input devices of the sensor modules 7015 and the output that is to be commanded by the device module 7017.

For example, in the embodiment including IMUs 7096 on both feet 7021 of the user, the pitch $\theta_{Pitch}$ from the user's right foot 7021 may be assigned "elbow flex" in bulk mode and "wrist flex" in finesse mode. The roll $\theta_{Roll}$ from the user's right foot 7021 may be assigned "humeral rotate" in bulk mode and "wrist rotate" in finesse mode. The pitch $\theta_{Pitch}'$ from the user's left foot 7021 may be assigned to toggle forward and backward through the grip options in finesse mode. The roll $\theta_{Roll}'$ from the user's left foot may be assigned to open and close the prosthetic hand 7136 in finesse mode. Depending on the prosthetic device 7012, there may be various IMU signals translating by the device module 7017 to various control commands for both bulk mode and finesse mode. Additionally, in embodiments having a single IMU 7096, the orientation signals from the single IMU 7096 will be assigned the various control commands.

Figure 57A:
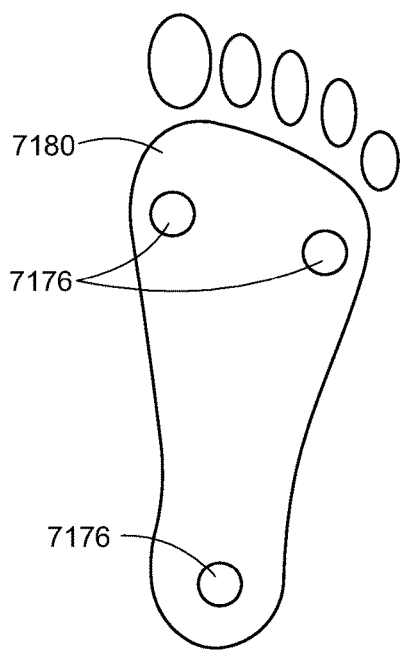
FIG. 57A is a top view of another embodiment of a sensor module according to the present invention.
Figure 57B:
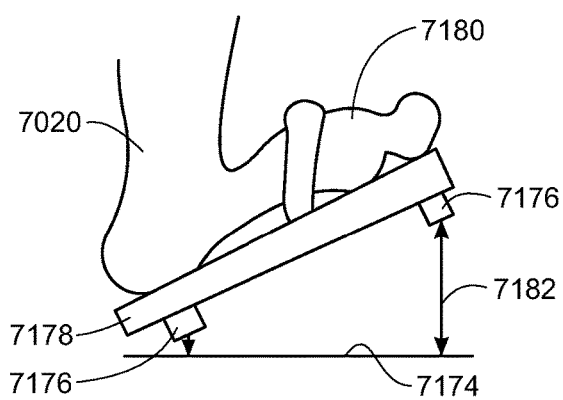
FIG. 57B is a side view of the sensor module of FIG. 57A.
Figure 57C:
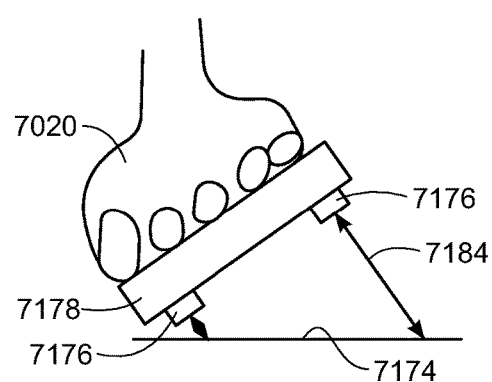
FIG. 57C is a front view of the sensor module of FIG. 57A.

As discussed above, the IMUs 7096 may be placed elsewhere on the user, for example, the shoulder, residuum, knee or lower leg. Referring to FIGS. 57A-57C, in some embodiments, rather than the IMU 7096, which determines the orientation of the user's foot 7021 relative to gravity, the orientation of the user's foot 7021 may instead be determined by measuring the distance from the bottom of the user's foot 7021 to the ground 7174. In some embodiments, this measurement may be determined using optical sensors 7176 located at a plurality of locations on the bottom of the user's foot 7021. For example, one optical sensor 7176 may be located at the heel 7178 of the foot and two optical sensors 7176 may be located along opposite edges of the foot in the in a toe region 7180. These optical sensors 7176 measure the distance between the user's foot and the surface 7174 the user is on. For example, when the user pitches their foot upwards, as seen in FIG. 57B, the sensor may determine the pitch distance 7182 and the sensor CPU 7019 may compute the angle $\theta_{Pitch}$ of the bottom of the user's foot 7021 to the surface 7174. Similarly, if the user rolls their foot sideways, as seen in FIG. 57C, the sensor may determine the roll distance 7184 and the sensor CPU 7019 may compute the angle $\theta_{Roll}$ of the bottom of the user's foot 7021 to the surface 7174.

Various control systems have been described herein including those to impart end-point control onto a prosthetic device 7012. Although the exemplary embodiments of the present invention discuss control systems for users that are shoulder disarticulation amputees, the current methods and systems may be broken down for use with prosthetic devices for trans-humerus and trans-radial amputees. For example, if the user's arm has humeral rotation, the bulk movement may be simplified to include only elbow flexion. Similarly, for trans-radial amputees, bulk movement may be provided entirely by the user's arm, with the control system providing only finesse movement. Thus, depending on the user's degree of amputation, the bulk mode provided by the control system may be changed or removed entirely, such that some embodiments of the present invention will provide both bulk and finesse modes, other embodiments will provide only the finesse mode and still other embodiments will provide partial bulk control along with the finesse mode.

Figure 58:
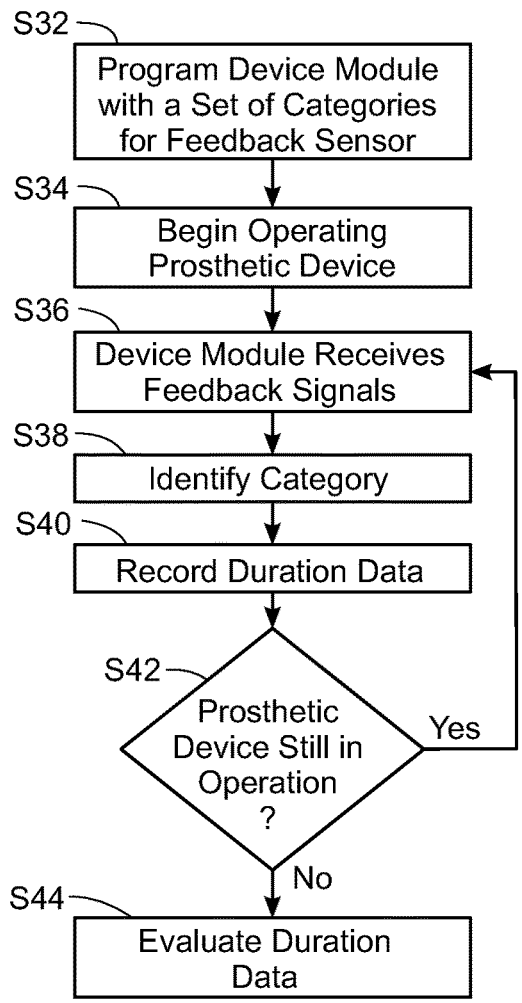
FIG. 58 is a process diagram of an embodiment of data collection according to the present invention.

As discussed above in connection with FIG. 1A, the feedback sensors 14 of the prosthetic device 12 send signals to the device module 17 that the device module may use to command the actuators 13 of the prosthetic device 12. Additionally, the device module 17 may also advantageously store data relating to the usage of the prosthetic device 12 to allow the control system 10 to be tailored to the particular user and/or to allow a technician to identify portions of the prosthetic device 12 that may be improved. Referring to FIG. 58, in some embodiments, the device module 17, shown in FIG. 1A, is programmed with a set of categories for each feedback sensor 14, shown in FIG. 1A, in S32, spanning the total range of possible signals received from the feedback sensor 14, shown in FIG. 1A. For example, if the feedback sensor 14, shown in FIG. 1A, is measuring rotational position of a prosthetic joint that is capable of rotating from a zero degree (0°) position to a ninety degree (90°) position, the set of categories may be, for instance, zero degrees to fifteen degrees (0°-15°), fifteen degrees to thirty degrees (15°-30°), thirty degrees to forty-five degrees (30°-45°), forty-five degrees to sixty degrees (45°-60°), sixty degrees to seventy-five degrees (60°-75°) and seventy-five degrees to ninety degrees (75°-90°). As should be understood by those skilled in the art, the number of categories in the set or categories and/or the size of each category within the set of categories may be varied for each feedback sensor 14, shown in FIG. 1A, depending upon the desired measurement precision.

The prosthetic device 12, shown in FIG. 1A, is then operated by the user in S34. While the prosthetic device 12, shown in FIG. 1A, is in operation, feedback signals from the feedback sensors 14, shown in FIG. 1A, are transmitted to, and received by, the device module 17, shown in FIG. 1A, in S36. The device module 17, shown in FIG. 1A, identifies which category of the set of categories that the feedback signal falls into in S38 and records the total duration of time that the at least one feedback signal is in the identified category in S40. This process may continue until it is evaluated in S42 that the prosthetic device 12, shown in FIG. 1A, is no longer in operation. Once the device is no longer in operation, the recorded duration data may be evaluated by the technician in S44.

Figure 61:
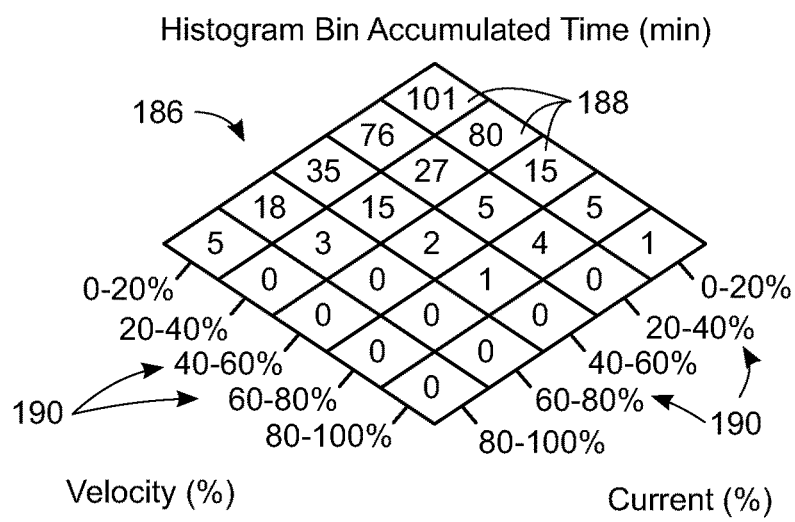
FIG. 61 is a histogram of data collected according to the data collection embodiment of FIG. 58.
Figure 59:
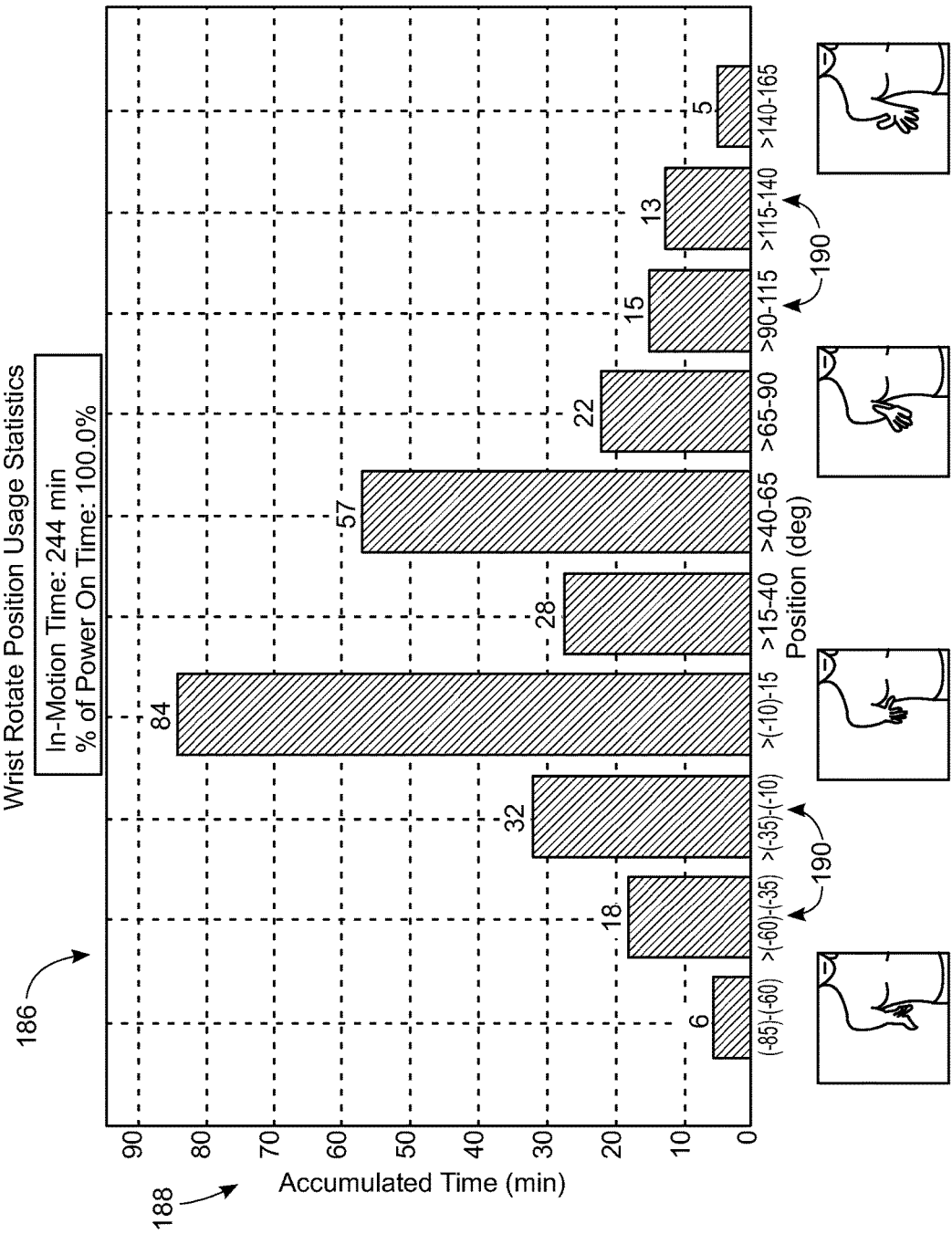
FIG. 59 is a histogram of data collected according to the data collection embodiment of FIG. 58.
Figure 60:
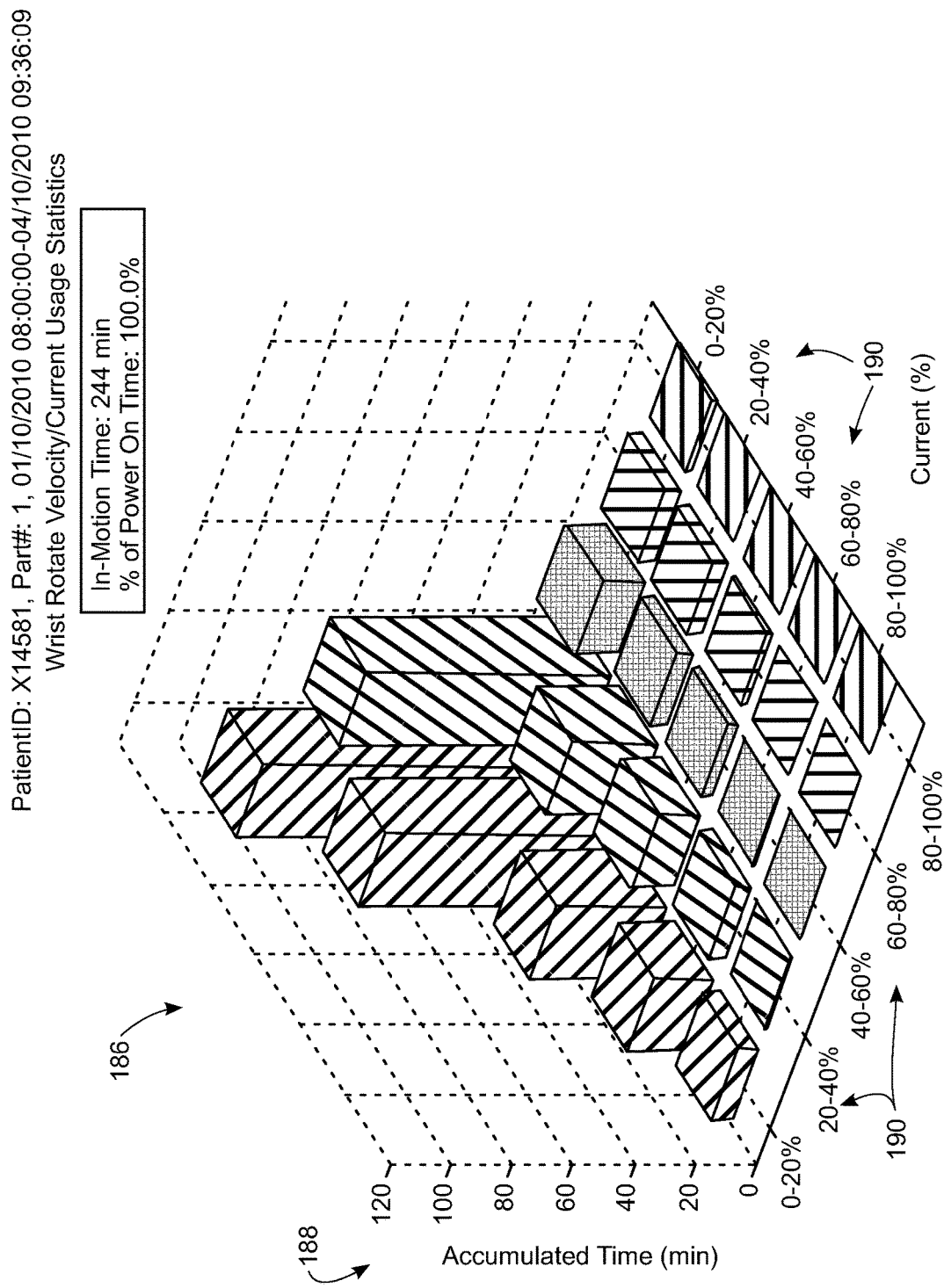
FIG. 60 is a histogram of data collected according to the data collection embodiment of FIG. 58.

In particular, the technician may generate various plots to evaluate the total time that the particular feedback signal was in each particular category. For instance, referring to FIG. 59, a wrist rotational position histogram 186 may be generated for a prosthetic wrist joint to evaluate an accumulated time 188 that the wrist joint was in each position category 190. Similarly, referring to FIGS. 60 and 61, the technician may form histograms 186 showing accumulated time 188 verse categories 190 for a variety of other feedback signals from a variety of other feedback sensors 14, including joint velocity, joint loading, actuator current, actuator torque, battery temperature, or the like. For instance, the prosthetic hand assembly may include position and/or force sensors on various fingers, allowing usage of the various grips discussed above to be evaluated.

Additionally, although described in terms of a feedback sensors, the device module 17, shown in FIG. 1A, may also collect durational data with regard to the time in which the prosthetic device 12, shown in FIG. 1A, is controlled in each of the various prosthetic control modes described herein.

This durational data collected by the device module 17, shown in FIG. 1A, allows the technician to configure the prosthetic device 12, shown in FIG. 1A, for each particular user. For example, the technician may program the most intuitive body input signals from the IMUs 7096 and sensor 7018, shown in FIG. 31A, to be used by the device module 7017, shown in FIG. 31A, to command the most used prosthetic motions. Similarly, the technician may program lesser used control modes to be commanded by less intuitive body input signals. In some cases, the control system 10 for particular users may even be customized to remove control modes that are not used by those particular users.

In addition to allowing for customization of the control system 10, shown in FIG. 1A, the durational data may also be used to identify areas for improvement of the prosthetic device itself. For instance, the durational data may indicate particular joints of the prosthetic device that are underpowered, allowing them to be redesigned to provide additional power, or overpowered, allowing them to be redesigned to reduce weight of the prosthetic device 12, shown in FIG. 1A. Similarly, for overpowered joints, the prosthetic device 12, shown in FIG. 1A, may be redesigned to reduce the battery power used by those joints to improve batter life. Additionally, the durational data based on battery current, temperature and/or capacity may aid in the selection of a better battery for the prosthetic device 12, shown in FIG. 1A. Thus, the collection of durational data by the device module 17, shown in FIG. 1A, advantageously allows for both customization and improvement of the prosthetic device 12, shown in FIG. 1A.

As is discussed herein, various embodiments of device modules and sensor modules as well as the control apparatus have been described. The control apparatus may be used to control a prosthetic device using one or more sensors. With respect to switch-based sensors, including but not limited to, foot sensors and/or joysticks, etc., these sensors include an application of force onto the switch-based sensor and a reaction force. Thus, for example, with respect to foot sensors, the application of force by the user to a specific area (e.g., location of the sensor) may be necessary for the sensor to receive the signal from the user. However, where there is no reaction force, e.g., when the user's shoe is not against a surface, the sensor may not receive the signal. Further, as sensors may require the application of force on a particular point to receive a signal, this may present additional difficulties. Also, the application of force to a sensor may contribute to soreness or other irritation imparted onto the user by the repetition of force application on a particular point of the user's foot and/or other body area.

Additionally, although switch-based sensors may be used, in some embodiments, it may be difficult for the sensors to receive signals related to multiple axes at the same time. In some embodiments, for multiple-axis movement, the sensors may require receipt of multiple inputs regarding various axes. In some embodiments, these multiple inputs may be coordinated by the user, and in some embodiments, multiple inputs may be received by the sensor and then coordinated by the control system for a determination of intended/desired multiple axis movement (i.e., user command). This may contribute to less control resolution and/or may contribute to difficulty in use.

Thus, it may be desirable to use at least one non switch-based sensor to receive user input regarding desired/intended motion of a prosthetic and/or other device. As discussed herein, an IMU may be used. However, other non-switch based sensors may be used in various embodiments. In some embodiments, the non-switch based sensor may include receiving input from the user regarding desired/intended motion of a prosthetic of other device. In some embodiments, the non-switch based sensor is not reliant on force application (and reaction force) and/or position of the sensor. These non-switch based sensors may be beneficial for many reasons, including but not limited to, one or more of the following. The sensor may sense motion without the application of force. The sensor may receive multiple axis input with a single motion (rather than multiple, coordinated motions). The sensor may be placed anywhere and receive indication of intended/desired movement through motion. Once placed in a position (e.g., anywhere, for example, but not limited to, connected directly or indirectly on the user) a position may be "zeroed" and thus, change in position, including but not limited to, rate of change of position and/or the derivative of the position (acceleration) and/or distance covered by the change in position, may be used as inputs to the control system. In some embodiments, a sensor that may indicate the desired and/or intended direction and/or speed and/or position of the prosthetic and/or other device may be the input. In some embodiments, the sensor may include, but is not limited to, one or more EEG or EMG signal(s) from the user and/or one or accelerometers and/or one or more gyroscopes. In various embodiments, the sensor may be any sensor that meets one or more of these stated functions and/or benefits.

Therefore, various embodiments of the control apparatus include directional and proportional control of a prosthetic device and/or other device without reliance on one or more switches and/or reaction force and without concern for position of the sensor (i.e., the sensor may be "zeroed" or "nulled out" and/or position is not indicative (e.g., EEG and/or EMG signal)). For example, in some exemplary embodiments, the system may re-zero when commanded based on the position of the foot, thereby advantageously allowing the user to account for different foot orientations by offsetting the control system based on the re-zeroed position of the foot. Additionally, in some embodiments that implement 3-axis IMUs, the control system itself may eliminate the need for the user to re-zero the system since the 3-axis IMU may generate a "virtual flat" IMU, e.g. if the user wears high heeled shoes, the system may advantageously be re-zeroed to interpret the commands as though they were "flat" footed commands. Further, in some embodiments, rate of change etc. may be used by the system/apparatus for proportional and/or directional control so that, in various embodiments, input from the sensor may be used to command a device, including but not limited to, a prosthetic device.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. An arm prosthetic device having a plurality of actuators each configured to control the prosthetic arm and a control module for commanding the plurality of actuators, the control module in communication with at least one sensor module housed separately from the prosthetic device and independently movable relative thereto, the at least one sensor module adapted to detect orientation changes of the at least one sensor module, the control module configured to perform operations comprising:
   receiving at least one orientation signal from the sensor module, the orientation signal being indicative of a commanded direction of movement of the prosthetic device;
   evaluating whether the prosthetic device may move in the commanded direction based on a current angle of rotation of the prosthetic device; and
   commanding at least one actuator of the plurality of actuators to move the prosthetic device in the commanded direction.

2. The prosthetic device according to claim 1, wherein the control module maintains the current angle of rotation of the prosthetic device when commanding the at least one actuator to move the prosthetic device in the commanded direction.

3. The prosthetic device according to claim 1, wherein the control module is further configured to perform operations comprising:
   adjusting the angle of rotation of the prosthetic device if the prosthetic device cannot move in the commanded direction based on the current angle of rotation.

4. The prosthetic device according to claim 3, wherein, each actuator of the plurality of actuators includes joint limits defining a movement range of the actuator, and wherein the control module adjusts the angle of rotation of the prosthetic device in accordance with the joint limits of the plurality of actuators.

5. The prosthetic device according to claim 4, wherein the control module adjusts the angle of rotation of the prosthetic device in accordance with at least one position limiting boundary of the prosthetic device.

6. An arm prosthetic device comprising a plurality of actuators each configured to control the prosthetic arm, each actuator of the plurality of actuators including actuation limits defining an actuation range for the actuator, and a control module for commanding the plurality of actuators, the control module in communication with at least one sensor module, the at least one sensor module housed separately from the prosthetic device and independently movable relative thereto, the at least one sensor module adapted to detect orientation changes of the at least one sensor module, the control module configured to perform operations comprising:
   receiving at least one orientation signal from the sensor module, the orientation signal being indicative of a commanded direction of movement of the prosthetic device;
   evaluating whether the prosthetic device may move in the commanded direction based on a current angle of rotation of the prosthetic device;
   commanding at least one actuator of the plurality of actuators to move the prosthetic device in the commanded direction; and
   adjusting the angle of rotation of the prosthetic device in accordance with the actuation limits of the plurality of actuators.

7. The prosthetic device according to claim 6, wherein the control module maintains the current angle of rotation of the prosthetic device when commanding the at least one actuator to move the prosthetic device in the commanded direction.

8. The prosthetic device according to claim 6, wherein the control module is further configured to perform operations comprising:
   adjusting the angle of rotation of the prosthetic device in accordance with the actuation limits of the plurality of actuators if it is evaluated that the prosthetic device cannot move in the commanded direction based on the current angle of rotation.

9. The prosthetic device according to claim 8, wherein the control module adjusts the angle of rotation of the prosthetic device in accordance with at least one position limiting boundary of the prosthetic device.

* * * * *